(12) United States Patent
Dehmlow et al.

(10) Patent No.: US 8,288,541 B2
(45) Date of Patent: Oct. 16, 2012

(54) PIPERAZINE AMIDE DERIVATIVES

(75) Inventors: Henrietta Dehmlow, Loerrach (DE); Bernd Kuhn, Reinach BL (CH); Ulrike Obst Sander, Reinach BL (CH); Stephan Roever, Inzlingen (DE); Tanja Schulz-Gasch, Liestal (CH); Matthew Wright, Basel (CH); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 686 days.

(21) Appl. No.: 12/186,555

(22) Filed: Aug. 6, 2008

(65) Prior Publication Data

US 2009/0048264 A1 Feb. 19, 2009

(30) Foreign Application Priority Data

Aug. 13, 2007 (EP) .................................... 07114219

(51) Int. Cl.
| | |
|---|---|
| *C07D 241/02* | (2006.01) |
| *C07D 401/06* | (2006.01) |
| *C07D 401/12* | (2006.01) |
| *C07D 403/12* | (2006.01) |
| *C07D 409/12* | (2006.01) |
| *C07D 413/12* | (2006.01) |
| *A61K 31/497* | (2006.01) |
| *A61P 1/16* | (2006.01) |
| *A61P 1/18* | (2006.01) |
| *A61P 3/06* | (2006.01) |
| *A61P 3/10* | (2006.01) |

(52) U.S. Cl. ... 544/357; 544/359; 544/364; 514/252.11; 514/253.13; 514/316

(58) Field of Classification Search ............. 514/252.11, 514/235.13, 316; 544/357, 359, 364
See application file for complete search history.

(56) References Cited

U.S. PATENT DOCUMENTS

| | | |
|---|---|---|
| 4,556,740 A | 12/1985 | Hansen et al. |
| 5,302,738 A | 4/1994 | Foricher et al. |
| 5,488,172 A | 1/1996 | Cereghetti et al. |
| 5,965,559 A | 10/1999 | Faull et al. |
| 2005/0288317 A1 | 12/2005 | Yao et al. |

FOREIGN PATENT DOCUMENTS

| | | |
|---|---|---|
| EP | 104 375 | 4/1984 |
| EP | 580 331 | 1/1994 |
| EP | 398 132 | 9/1995 |
| WO | WO 92/16535 | 10/1992 |
| WO | WO 03/099769 | 12/2003 |
| WO | WO 2004/076418 | 9/2004 |
| WO | WO 2005/121093 | 12/2005 |
| WO | 2006/012173 | 2/2006 |
| WO | WO 2008/119657 | 10/2008 |

OTHER PUBLICATIONS

Lund et al., Arterioscler. Thromb. Vasc. Biol., 23, pp. 1169-1177 (2003).
Mitro et al., Nature, 445, pp. 219-223 (2007).
Joseph et al., Curr. Opin. Pharmacol., 3, pp. 192-197 (2003).
Cao et al., J. Biol. Chem., 278, pp. 1131-1136 (2003).
Gubert et al., Synthesis, pp. 318-320 (1991).
Benincori et al., J. Org. Chem., 61, pp. 6244-6251 (1996).
Bennett et al, *Expert Opin on Therapeutic Patents, Informa Healthcare*, 14(7), 967-982 (2004) XP002342352.
Chilean Office Action dated Jun. 15, 2011 for Chilean Pat App. Corres. to U.S. Appl. No. 12/186,555.
First Office Action in copending Chinese patent application No. 200880103083 (Oct. 14, 2011).

*Primary Examiner* — Kortney L Klinkel
(74) *Attorney, Agent, or Firm* — George W. Johnston; Dennis P. Tramaloni; Brian C. Remy

(57) ABSTRACT

The invention is concerned with novel piperazine amide derivatives of formula (I)

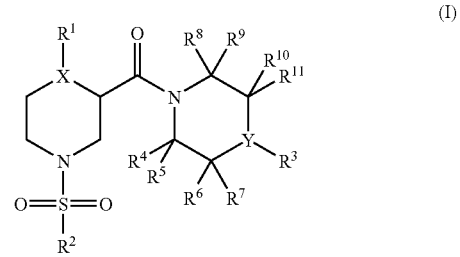

wherein $R^1$ to $R^{11}$, W, X and Y are as defined in the description and in the claims, as well as physiologically acceptable salts thereof. These compounds bind to LXR alpha and LXR beta and can be used as medicaments.

22 Claims, No Drawings

PIPERAZINE AMIDE DERIVATIVES

PRIORITY TO RELATED APPLICATION(S)

This application claims the benefit of European Patent Application No. 07114219.4, filed Aug. 13, 2007, which is hereby incorporated by reference in its entirety.

BACKGROUND OF THE INVENTION

Liver-X-Receptors (LXRs) are members of the nuclear hormone receptor superfamily. The LXRs are activated by endogenous oxysterols and glucose and regulate the transcription of genes controlling multiple metabolic pathways. Two subtypes, LXRalpha and LXRbeta, have been described (Willy, P. J. et al., Genes Dev. 1995, 9:1033-45; Song, C. et al., Proc Natl Acad Sci USA. 1994, 91:10809-13). LXRbeta is ubiquitously expressed, while LXRalpha is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs also appear to regulate genes involved in glucose metabolism, cholesterol metabolism in the brain, cellular differentiation and apoptosis, inflammation, and infectious diseases (Geyeregger, R. et al., Cell. Mol. Life. Sci. 2006, 63:524-539).

About half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller N E., Lipids 1978,13:914-9). The protective function of HDL derives from its role in a process termed reverse cholesterol transport (Forrester, J. S. and Shah, P. K., Am. J. Cardiol. 2006, 98:1542-49). HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon, T. et al., Am J Med. 1977, 62:707-14).

At present, the estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol >240 mg/dl is 37% in diabetic men and 44% in women. The rates for LDL-C>160 mg/dl are 31% and 44%, and for HDL-C<35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance. Recent studies provide evidence that modulators of LXRs would result in compounds with enhanced therapeutic potential, and as such, modulators of LXRs should improve the plasma lipid profile, and raise HDL-C levels (Lund, E. G. et al., Arterioscler. Thromb. Vasc. Biol. 2003, 23:1169-77; Mitro, N. et al., Nature 2007, 445: 219-23). LXRs are also known to control the efflux of cholesterol from the macrophage foam cell of the atherosclerotic lesion, and agonists of LXRs have been shown to be atheroprotective (Joseph, S. B. and Tontonoz, P., Curr. Opin. Pharmacol. 2003, 3:192-7). Thus, modulators of LXRs would be effective treatments for the atherosclerotic disease which underlies the cardiovascular morbidity and mortality of stroke and heart disease. Recent observations also suggest that there is an independent LXR mediated effect on insulin-sensitization in addition to its role in atheroprotection (Cao, G. et al., J Biol Chem. 2003, 278:1131-6). Thus LXR modulators can also show superior therapeutic efficacy on HDL-raising and atheroprotection, with additional effects on diabetes, compared to current therapies.

While compounds that bind to and activate LXR alpha and LXR beta have previously been suggested (e.g.: WO 03/099769), the present invention provides the novel compounds of formula (I) which bind to LXR alpha and/or LXR beta and unexpectedly exhibit improved pharmacological properties compared to the compounds known in the art, concerning e.g. metabolic stability, selectivity, bioavailability and activity.

SUMMARY OF THE INVENTION

The invention is concerned with novel piperazine amide derivatives of the formula (I)

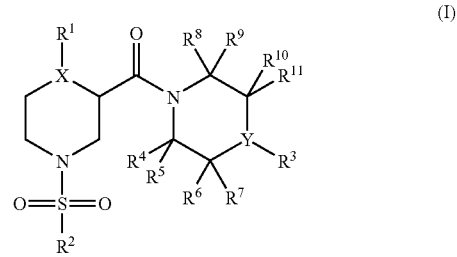

wherein
X is N or CH;
Y is N or CH;

R¹ is lower-alkyl, lower-alkoxy-lower-alkyl, halogen-lower-alkyl, lower-alkenyl, cycloalkyl, cycloalkyl-lower-alkyl, aryl, aryl-lower-alkyl, heterocyclyl, heterocyclyl-lower-alkyl, heteroaryl or heteroaryl-lower-alkyl, wherein a cycloalkyl, aryl, heterocyclyl or heteroaryl can optionally be substituted with 1 to 5 substituents independently selected from the group consisting of halogen, lower-alkyl, lower-alkoxy, fluoro-lower-alkyl and fluoro-lower-alkoxy;

R² is lower-alkyl, fluoro-lower-alkyl, lower-alkoxy-lower-alkyl, cycloalkyl, cycloalkyl-lower-alkyl, aryl, aryl-lower-alkyl, heterocyclyl, heterocyclyl-lower-alkyl, heteroaryl or heteroaryl-lower-alkyl, wherein a cycloalkyl, aryl, heterocyclyl or heteroaryl can optionally be substituted with 1 to 5 substituents independently selected from the group consisting of halogen, lower-alkyl, lower-alkoxy, fluoro-lower-alkyl, fluoro-lower-alkoxy, lower-alkoxy-carbonyl and phenyl;

R³ is aryl or heteroaryl, which aryl or heteroaryl can optionally be substituted with 1 to 5 substituents independently selected from the group consisting of halogen, CN, lower-alkyl, fluoro-lower-alkyl, lower-alkoxy and fluoro-lower-alkoxy;

$R^4$, $R^5$, $R^6$, $R^7$, $R^8$, $R^9$, $R^{10}$ and $R^{11}$ independently from each other are hydrogen or lower-alkyl, or $R^4$ and $R^5$ are bound together, or $R^6$ and $R^7$ are bound together, or $R^8$ and $R^9$ are bound together, or $R^{10}$ an $R^{11}$ are bound together, to form a ring together with the carbon atom to which they are attached, and —$R^4$-$R^5$—, —$R^6$-$R^7$—, —$R^8$-$R^9$— and/or —$R^{10}$-$R^{11}$— is —$(CH_2)_{2-6}$—;

and pharmaceutically acceptable salts thereof.

Further, the invention is concerned with a process for the manufacture of the above compounds, pharmaceutical preparations which contain such compounds as well as the use of these compounds for the production of pharmaceutical preparations.

DETAILED DESCRIPTION OF THE INVENTION

A. Definitions

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

Lower-alkyl groups can be substituted, e.g. by 1 to 5, preferably 1 to 3, halogen. Such groups are referred to as "halogen-lower-alkyl". Examples of halogen-lower-alkyl groups are e.g. chlororethyl or iodopropyl groups.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$.

The term "alkenyl", alone or in combination with other groups, stands for a straight-chain or branched hydrocarbon residue comprising an olefinic bond and up to 20, preferably up to 16 carbon atoms. The term "lower-alkenyl" refers to a straight-chain or branched hydrocarbon residue comprising an olefinic bond and up to 7, preferably up to 4 carbon atoms, such as e.g. 2-propenyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups.

The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl", alone or in combination, relates to the phenyl or naphthyl group, preferably the phenyl group, which can optionally be substituted by 1 to 5, preferably 1 to 3, substituents independently selected from the group consisting of lower-alkyl, lower-alkoxy, halogen, hydroxy, CN, $CF_3$, amino, aminocarbonyl, carboxy, $NO_2$, dioxo-lower-alkylene (forming e.g. a benzodioxyl group), lower-alkylsufonyl, aminosulfonyl, lower-alkylcarbonyl, lower-alkylcarbonyloxy, lower-alkylcarbonyl-NH, lower-alkoxycarbonyl, fluoro-lower-alkyl, fluoro-lower-alkoxy, lower-alkoxy-lower-alkyl, cycloalkyl and phenyloxy. Unless stated otherwise, preferred substituents are halogen, lower-alkyl, fluoro-lower-alkyl, CN and lower-alkoxycarbonyl. Furthermore, aryl groups can preferably be substituted as described below in the description and claims.

The term "heterocyclyl", alone or in combination, signifies a saturated or partially unsaturated 4- to 10-membered, mono- or bicyclic heterocycle which contains one or more hetero atoms, preferably one to three, selected from nitrogen, oxygen and sulphur. Examples of such heterocyclyl groups are piperidinyl, piperazinyl, pyrrolidinyl, imidazolidinyl, pyrazolidinyl, pyranyl, morpholinyl and oxetanyl. Preferred are piperidinyl and pyranyl. A heterocyclyl group may optionally have a substitution pattern as described earlier in connection with the term "aryl". Furthermore, heterocyclyl groups can preferably be substituted as described below in the description and claims.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, pyrimidinyl, pyrazinyl, thiophenyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl, 3-thieno[3,2-c]pyridin-4-yl and quinolinyl. Preferred heteroaryl groups are isoxazolyl, quinolinyl, thiophenyl, pyridinyl and pyrazinyl. A heteroaryl group may optionally have a substitution pattern as described earlier in connection with the term "aryl". Furthermore, heteroaryl groups can preferably be substituted as described below in the description and claims.

B. Detailed Description of the Invention

The novel compounds of the present invention bind to and selectively activate LXR alpha and LXR beta or coactivate LXR alpha and LXR beta. Consequently, cholesterol absorption is reduced, HDL cholesterol is increased, and inflammatory atherosclerosis is reduced. Since multiple facets of combined dyslipidemia and cholesterol homeostasis are addressed by LXR modulators, novel compounds of the present invention have an enhanced therapeutic potential compared to the compounds already known in the art.

In detail, the present invention relates to compounds of formula (I)

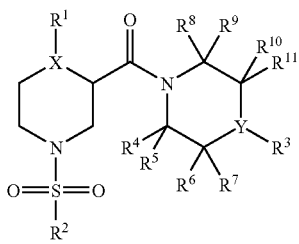

(I)

wherein
X is N or CH;
Y is N or CH;
$R^1$ is lower-alkyl, lower-alkoxy-lower-alkyl, halogen-lower-alkyl, lower-alkenyl, cycloalkyl, cycloalkyl-lower-alkyl, aryl, aryl-lower-alkyl, heterocyclyl, heterocyclyl-lower-alkyl, heteroaryl or heteroaryl-lower-alkyl, wherein a cycloalkyl, aryl, heterocyclyl or heteroaryl can optionally be substituted with 1 to 5 substituents independently selected from the group consisting of halogen, lower-alkyl, lower-alkoxy, fluoro-lower-alkyl and fluoro-lower-alkoxy;
$R^2$ is lower-alkyl, fluoro-lower-alkyl, lower-alkoxy-lower-alkyl, cycloalkyl, cycloalkyl-lower-alkyl, aryl, aryl-lower-alkyl, heterocyclyl, heterocyclyl-lower-alkyl, heteroaryl or heteroaryl-lower-alkyl, wherein a cycloalkyl, aryl, heterocyclyl or heteroaryl can optionally be substituted with 1 to 5 substituents independently selected from the group consisting of halogen, lower-alkyl, lower-alkoxy, fluoro-lower-alkyl, fluoro-lower-alkoxy, lower-alkoxy-carbonyl and phenyl;
$R^3$ is aryl or heteroaryl, which aryl or heteroaryl can optionally be substituted with 1 to 5 substituents independently selected from the group consisting of halogen, CN, lower-alkyl, fluoro-lower-alkyl, lower-alkoxy and fluoro-lower-alkoxy;

$R^4$, $R^5$, $R^6$, $R^7$, $R^8$, $R^9$, $R^{10}$, and $R^{11}$ independently from each other are hydrogen or lower-alkyl, or $R^4$ and $R^5$ are bound together, or $R^6$ and $R^7$ are bound together, or $R^8$ and $R^9$ are bound together, or $R^{10}$ an $R^{11}$ are bound together, to form a ring together with the carbon atom to which they are attached, and —$R^4$-$R^5$—, —$R^6$-$R^7$—, —$R^8$-$R^9$— and/or —$R^{10}$-$R^{11}$— is —$(CH_2)_{2-6}$—;
and pharmaceutically acceptable salts thereof.

Compounds of formula (I) are individually preferred and physiologically acceptable salts thereof are individually preferred, with the compounds of formula (I) being particularly preferred.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid The compounds of formula (I) have one or more asymmetric C atoms and can therefore exist as an enantiomeric mixture, mixture of stereoisomers or as optically pure compounds.

Preferred compounds of the present invention are those, wherein X is N. Other preferred compounds are those, wherein X is CH. Furthermore, it is preferred that Y is N.

Other preferred compounds of the present invention are those, wherein $R^1$ is lower-alkyl, aryl or aryl-lower-alkyl, wherein aryl is optionally substituted with 1 to 3 substituents independently selected from the group consisting of halogen and lower-alkyl. More preferably, $R^1$ is lower-alkyl or phenyl, which phenyl is optionally substituted with 1 to 2 substituents independently selected from the group consisting of halogen and lower-alkyl. Even more preferably, $R^1$ is n-butyl, phenyl, 4-fluoro-2-methyl-phenyl, 2-methyl-phenyl, 4-fluoro-phenyl, 2-fluoro-4-methyl-phenyl or 2,4-difluoro-phenyl.

Another preferred embodiment of the present invention relates to compounds of formula (I) as described above, wherein $R^2$ is lower-alkyl, aryl or heteroaryl selected from the group consisting of isoxazolyl, quinolinyl, thiophenyl and pyridinyl, which aryl or heteroaryl is optionally substituted with 1 to 3 substituents independently selected from the group consisting of halogen, lower-alkyl, lower-alkoxy, fluoro-lower-alkyl, lower-alkoxy-carbonyl and phenyl. Preferably, $R^2$ is lower-alkyl, phenyl or heteroaryl selected from the group consisting of quinolinyl and pyridinyl, which phenyl or heteroaryl is optionally substituted with 1 to 2 substituents independently selected from the group consisting of halogen, lower-alkoxy and fluoro-lower-alkyl. More preferably, $R^2$ is methyl, isopropyl, 3-methoxy-phenyl, 3-chloro-phenyl, 2-trifluoromethyl-phenyl, quinoline-8-yl or pyridin-3-yl.

Furthermore, it is preferred, that $R^3$ is aryl or a heteroaryl selected from the group consisting of pyridinyl and pyrazinyl, which aryl or heteroaryl is optionally substituted with 1 to 3 substituents independently selected from the group consisting of halogen, lower-alkyl and fluoro-lower-alkyl. More preferably, $R^3$ is phenyl or pyrazinyl, which phenyl or pyrazinyl is optionally substituted with 1 to 2 substituents independently selected from the group consisting of halogen and lower-alkyl. Even more preferably, $R^3$ is 2,5-dimethyl-phenyl, 2-methyl-5-chloro-phenyl, 2,5-dichloro-phenyl or 3,6-dimethyl-pyrazin-2-yl.

Furthermore, it is preferred that at least 4 of $R^4$, $R^5$, $R^6$, $R^7$, $R^8$, $R^9$, $R^{10}$ and $R^{11}$ are hydrogen. It is also preferred that not more than two of —R⁴-R⁵—, —R⁶-R⁷—, —R⁸-R⁹— and —R¹⁰-R¹¹— are bound together to form a ring. Particularly preferred compounds according to the present invention are those, wherein $R^4$, $R^5$, $R^6$, $R^7$, $R^8$, $R^9$, $R^{10}$ and $R^{11}$ are hydrogen.

In particular, preferred compounds are the compounds of formula (I) described in the examples as individual compounds as well as pharmaceutically acceptable salts thereof.

Preferred compounds of formula (I) are those selected from the group consisting of

[4-(2,5-Dimethyl-phenyl)-piperazin-1-yl]-[1-(4-fluoro-2-methyl-phenyl)-4-(3-methoxy-benzenesulfonyl)-piperazin-2-yl]-methanone,

[4-(3-Chloro-benzenesulfonyl)-1-(4-fluoro-2-methyl-phenyl)-piperazin-2-yl]-[4-(2,5-dimethyl-phenyl)-piperazin-1-yl]-methanone,

[4-(3-Chloro-benzenesulfonyl)-1-(4-fluoro-2-methyl-phenyl)-piperazin-2-yl]-[4-(5-chloro-2-methyl-phenyl)-piperazin-1-yl]-methanone,

[4-(3-Chloro-benzenesulfonyl)-1-(4-fluoro-2-methyl-phenyl)-piperazin-2-yl]-[4-(2,5-dichloro-phenyl)-piperazin-1-yl]-methanone, (−)-[4-(3-Chloro-benzenesulfonyl)-1-(4-fluoro-2-methyl-phenyl)-piperazin-2-yl]-[4-(2,5-dichloro-phenyl)-piperazin-1-yl]-methanone,

[4-(3-Chloro-benzenesulfonyl)-1-(4-fluoro-2-methyl-phenyl)-piperazin-2-yl]-(4-o-tolyl-piperazin-1-yl)-methanone,

[4-(2,5-Dichloro-phenyl)-piperazin-1-yl]-[4-(3-methoxy-benzenesulfonyl)-1-phenyl-piperazin-2-yl]-methanone,

[4-(2,5-Dimethyl-phenyl)-piperazin-1-yl]-[4-(3-methoxy-benzenesulfonyl)-1-phenyl-piperazin-2-yl]-methanone,

[4-(5-Chloro-2-methyl-phenyl)-piperazin-1-yl]-[4-(3-methoxy-benzenesulfonyl)-1-phenyl-piperazin-2-yl]-methanone,

[4-(3-Chloro-benzenesulfonyl)-1-o-tolyl-piperazin-2-yl]-[4-(2,5-dichloro-phenyl)-piperazin-1-yl]-methanone,

[4-(3-Chloro-benzenesulfonyl)-1-o-tolyl-piperazin-2-yl]-[4-(5-chloro-2-methyl-phenyl)-piperazin-1-yl]-methanone,

[4-(3-Chloro-benzenesulfonyl)-1-o-tolyl-piperazin-2-yl]-[4-(2,5-dimethyl-phenyl)-piperazin-1-yl]-methanone,

[1-Benzyl-4-(3-methoxy-benzenesulfonyl)-piperazin-2-yl]-[4-(2,5-dimethyl-phenyl)-piperazin-1-yl]-methanone, (−)-[1-Benzyl-4-(3-methoxy-benzenesulfonyl)-piperazin-2-yl]-[4-(2,5-dimethyl-phenyl)-piperazin-1-yl]-methanone,

[1-Benzyl-4-(3-chloro-benzenesulfonyl)-piperazin-2-yl]-[4-(2,5-dimethyl-phenyl)-piperazin-1-yl]-methanone,

[1-Benzyl-4-(3,5-dimethyl-isoxazole-4-sulfonyl)-piperazin-2-yl]-[4-(2,5-dimethyl-phenyl)-piperazin-1-yl]-methanone,

[4-(3-Chloro-benzenesulfonyl)-1-propyl-piperazin-2-yl]-[4-(2,5-dimethyl-phenyl)-piperazin-1-yl]-methanone,

[1-Butyl-4-(3-chloro-benzenesulfonyl)-piperazin-2-yl]-[4-(2,5-dimethyl-phenyl)-piperazin-1-yl]-methanone,

[4-(3-Chloro-benzenesulfonyl)-1-pentyl-piperazin-2-yl]-[4-(2,5-dimethyl-phenyl)-piperazin-1-yl]-methanone,

[4-(3-Chloro-benzenesulfonyl)-1-isobutyl-piperazin-2-yl]-[4-(2,5-dimethyl-phenyl)-piperazin-1-yl]-methanone,

[4-(3-Chloro-benzenesulfonyl)-1-phenethyl-piperazin-2-yl]-[4-(2,5-dimethyl-phenyl)-piperazin-1-yl]-methanone,

[4-(4-Chloro-benzenesulfonyl)-1-pentyl-piperazin-2-yl]-[4-(2,5-dimethyl-phenyl)-piperazin-1-yl]-methanone,

[1-Butyl-4-(4-chloro-benzenesulfonyl)-piperazin-2-yl]-[4-(2,5-dimethyl-phenyl)-piperazin-1-yl]-methanone, [4-(4-Chloro-benzenesulfonyl)-1-phenyl-piperazin-2-yl]-[4-(2,5-dimethyl-phenyl)-piperazin-1-yl]-methanone,

[4-(2-Chloro-benzenesulfonyl)-1-(4-fluoro-2-methyl-phenyl)-piperazin-2-yl]-[4-(2,5-dichloro-phenyl)-piperazin-1-yl]-methanone,

[4-(2-Chloro-benzenesulfonyl)-1-(4-fluoro-2-methyl-phenyl)-piperazin-2-yl]-[4-(5-chloro-2-methyl-phenyl)-piperazin-1-yl]-methanone,

[4-(2-Chloro-benzenesulfonyl)-1-(4-fluoro-2-methyl-phenyl)-piperazin-2-yl]-[4-(2,5-dimethyl-phenyl)-piperazin-1-yl]-methanone,

[4-(2,5-Dichloro-phenyl)-piperazin-1-yl]-[1-(4-fluoro-2-methyl-phenyl)-4-(naphthalene-1-sulfonyl)-piperazin-2-yl]-methanone,

[4-(5-Chloro-2-methyl-phenyl)-piperazin-1-yl]-[1-(4-fluoro-2-methyl-phenyl)-4-(naphthalene-1-sulfonyl)-piperazin-2-yl]-methanone,

[4-(2,5-Dimethyl-phenyl)-piperazin-1-yl]-[1-(4-fluoro-2-methyl-phenyl)-4-(naphthalene-1-sulfonyl)-piperazin-2-yl]-methanone,

[1-(4-Fluoro-2-methyl-phenyl)-4-(naphthalene-1-sulfonyl)-piperazin-2-yl]-[4-(3-trifluoromethyl-pyridin-2-yl)-piperazin-1-yl]-methanone,

[4-(2,5-Dichloro-phenyl)-piperazin-1-yl]-[1-(4-fluoro-2-methyl-phenyl)-4-(quinoline-8-sulfonyl)-piperazin-2-yl]-methanone,

[4-(5-Chloro-2-methyl-phenyl)-piperazin-1-yl]-[1-(4-fluoro-2-methyl-phenyl)-4-(quinoline-8-sulfonyl)-piperazin-2-yl]-methanone,

[4-(2,5-Dimethyl-phenyl)-piperazin-1-yl]-[1-(4-fluoro-2-methyl-phenyl)-4-(quinoline-8-sulfonyl)-piperazin-2-yl]-methanone,

[4-(2,5-Dichloro-phenyl)-piperazin-1-yl]-[4-(propane-2-sulfonyl)-1-o-tolyl-piperazin-2-yl]-methanone,

[4-(Biphenyl-4-sulfonyl)-1-o-tolyl-piperazin-2-yl]-[4-(2,5-dichloro-phenyl)-piperazin-1-yl]-methanone, 3-{3-[4-(2,5-Dichloro-phenyl)-piperazine-1-carbonyl]-4-o-tolyl-piperazine-1-sulfonyl}-thiophene-2-carboxylic acid methyl ester,

[4-(3-Chloro-benzenesulfonyl)-1-(4-fluoro-2-methyl-phenyl)-piperazin-2-yl]-(3',6'-dimethyl-2,3,5,6-tetrahydro-[1,2']bipyrazinyl-4-yl)-methanone,

[1-Benzyl-4-(3-chloro-benzenesulfonyl)-piperazin-2-yl]-(3',6'-dimethyl-2,3,5,6-tetrahydro-[1,2']bipyrazinyl-4-yl)-methanone,

[4-(3-Chloro-phenyl)-piperidin-1-yl]-[1-(4-fluoro-2-methyl-phenyl)-4-(propane-2-sulfonyl)-piperazin-2-yl]-methanone,

[4-(3-Chloro-benzenesulfonyl)-1-o-tolyl-piperazin-2-yl]-(3',6'-dimethyl-2,3,5,6-tetrahydro-[1,2']bipyrazinyl-4-yl)-methanone, Cis-[4-(2,5-Dimethyl-phenyl)-piperazin-1-yl]-[-1-(3-methoxy-benzenesulfonyl)-4-phenyl-piperidin-3-yl]-methanone,

[4-(2,5-Dimethyl-phenyl)-piperazin-1-yl]-[(3S,4S)-1-(3-methoxy-benzenesulfonyl)-4-phenyl-piperidin-3-yl]-methanone,

[Trans-1-(3-Chloro-benzenesulfonyl)-4-phenyl-piperidin-3-yl]-[4-(2,5-dimethyl-phenyl)-piperazin-1-yl]-methanone,

[Trans-1-(3,5-Dimethyl-isoxazole-4-sulfonyl)-4-phenyl-piperidin-3-yl]-[4-(2,5-dimethyl-phenyl)-piperazin-1-yl]-methanone,

[4-(2,5-Dimethyl-phenyl)-piperazin-1-yl]-[(3S,4S)-1-(3-methoxy-benzenesulfonyl-4-o-tolyl-piperidin-3-yl]-methanone,

[(3S,4S)-1-(3-Chloro-benzenesulfonyl)-4-o-tolyl-piperidin-3-yl]-[4-(2,5-dimethyl-phenyl)-piperazin-1-yl]-methanone,

[4-(2,5-Dimethyl-phenyl)-piperazin-1-yl]-((3S,4S)-1-methanesulfonyl-4-o-tolyl-piperidin-3-yl)-methanone,
[(3S,4S)-1-(3-Chloro-benzenesulfonyl)-4-phenyl-piperidin-3-yl]-[4-(2,5-dimethyl-phenyl)-piperazin-1-yl]-methanone,
[4-(2,5-Dimethyl-phenyl)-piperazin-1-yl]-((3S,4S)-1-methanesulfonyl-4-phenyl-piperidin-3-yl)-methanone,
[(3R,4R)-1-(3-Chloro-benzenesulfonyl)-4-phenyl-piperidin-3-yl]-[4-(2,5-dimethyl-phenyl)-piperazin-1-yl]-methanone,
[4-(2,5-Dimethyl-phenyl)-piperazin-1-yl]-[(3S,4R)-1-(3-methoxy-benzenesulfonyl)-4-o-tolyl-piperidin-3-yl]-methanone,
[(3S,4S)-1-(3-Chloro-benzenesulfonyl)-4-(4-fluoro-phenyl)-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4S)-4-(4-fluoro-phenyl)-1-(2-trifluoromethyl-benzenesulfonyl)-piperidin-3-yl]-methanone,
[(3S,4R)-1-(3-Chloro-benzenesulfonyl)-4-(4-fluoro-phenyl)-piperidin-3-yl]-[4-(5-chloro-2-methyl-phenyl)-piperazin-1-yl]-methanone,
[(3S,4R)-1-(2-Chloro-benzenesulfonyl)-4-(4-fluoro-phenyl)-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4R)-4-(4-fluoro-phenyl)-1-(pyridine-3-sulfonyl)-piperidin-3-yl]-methanone,
[(3S,4S) or (3R,4R)-1-(3-Chloro-benzenesulfonyl)-4-(2-fluoro-4-methyl-phenyl)-piperidin-3-yl]-[4-(5-chloro-2-methyl-phenyl)-piperazin-1-yl]-methanone,
[(3S,4S) or (3R,4R)-1-(2-Chloro-benzenesulfonyl)-4-(2-fluoro-4-methyl-phenyl)-piperidin-3-yl]-[4-(5-chloro-2-methyl-phenyl)-piperazin-1-yl]-methanone,
(3S,4S) or (3R,4R)-[4-(5-Chloro-2-methyl-phenyl)-piperazin-1-yl]-[4-(2-fluoro-4-methyl-phenyl)-1-(2-trifluoromethyl-benzenesulfonyl)-piperidin-3-yl]-methanone,
(3S,4S) or (3R,4R)-[4-(5-Chloro-2-methyl-phenyl)-piperazin-1-yl]-[4-(2-fluoro-4-methyl-phenyl)-1-(pyridine-3-sulfonyl)-piperidin-3-yl]-methanone,
(3S,4S) or (3R,4R)-[4-(5-Chloro-2-methyl-phenyl)-piperazin-1-yl]-[4-(2-fluoro-4-methyl-phenyl)-1-(propane-2-sulfonyl)-piperidin-3-yl]-methanone,
[(3S,4R)-1-(3-Chloro-benzenesulfonyl)-4-phenyl-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4R)-4-phenyl-1-(2-trifluoromethyl-benzenesulfonyl)-piperidin-3-yl]-methanone,
[4-(5-Chloro-2-methyl-phenyl)-piperazin-1-yl]-[(3S,4R)-4-phenyl-1-(pyridine-3-sulfonyl)-piperidin-3-yl]-methanone,
[(3S,4R)-1-(3-Chloro-benzenesulfonyl)-4-o-tolyl-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4R)-4-o-tolyl-1-(2-trifluoromethyl-benzenesulfonyl)-piperidin-3-yl]-methanone,
[4-(5-Chloro-2-methyl-phenyl)-piperazin-1-yl]-[(3S,4R)-1-(pyridine-3-sulfonyl)-4-o-tolyl-piperidin-3-yl]-methanone,
[(3S,4R) or (3R,4S)-1-(3-Chloro-benzenesulfonyl)-4-(2,4-difluoro-phenyl)-piperidin-3-yl]-[4-(5-chloro-2-methyl-phenyl)-piperazin-1-yl]-methanone,
(3S,4R) or (3R,4S)-[4-(5-Chloro-2-methyl-phenyl)-piperazin-1-yl]-[4-(2,4-difluoro-phenyl)-1-(pyridine-3-sulfonyl)-piperidin-3-yl]-methanone,
[(3S,4S)-1-(3-Chloro-benzenesulfonyl)-4-phenyl-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4S)-4-phenyl-1-(2-trifluoromethyl-benzenesulfonyl)-piperidin-3-yl]-methanone,
[4-(5-Chloro-2-methyl-phenyl)-piperazin-1-yl]-[(3S,4S)-4-phenyl-1-(pyridine-3-sulfonyl)-piperidin-3-yl]-methanone,
[4-(5-Chloro-2-methyl-phenyl)-piperazin-1-yl]-[(3S,4S)-4-phenyl-1-(propane-2-sulfonyl)-piperidin-3-yl]-methanone,
[4-(5-Chloro-2-methyl-phenyl)-piperazin-1-yl]-((3S,4S)-1-methanesulfonyl-4-phenyl-piperidin-3-yl)-methanone,
[(3S,4S)-1-(3-Chloro-benzenesulfonyl)-4-o-tolyl-piperidin-3-yl]-[4-(5-chloro-2-phenyl)-piperazin-1-yl]-methanone,
[4-(5-Chloro-2-methyl-phenyl)-piperazin-1-yl]-[(3S,4S)-4-o-tolyl-1-(2-trifluoromethyl-benzenesulfonyl)-piperidin-3-yl]-methanone,
[4-(5-Chloro-2-methyl-phenyl)-piperazin-1-yl]-[(3S,4S)-1-(pyridine-3-sulfonyl)-4-o-tolyl-piperidin-3-yl]-methanone,
[4-(5-Chloro-2-methyl-phenyl)-piperazin-1-yl]-((3S,4S)-1-methanesulfonyl-4-o-tolyl-piperidin-3-yl)-methanone,
[(3S,4S) or (3R,4R)-1-(3-Chloro-benzenesulfonyl)-4-(4-fluoro-2-methyl-phenyl)-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4S) or (3R,4R)-4-(4-fluoro-2-methyl-phenyl)-1-(2-trifluoromethyl-benzenesulfonyl)-piperidin-3-yl]-methanone,
[4-(5-Chloro-2-methyl-phenyl)-piperazin-1-yl]-[(3S,4S) or (3R,4R)-4-(4-fluoro-2-methyl-phenyl)-1-(pyridine-3-sulfonyl)-piperidin-3-yl]-methanone,
[4-(5-Chloro-2-methyl-phenyl)-piperazin-1-yl]-[(3S,4S) or (3R,4R)-4-(4-fluoro-2-methyl-phenyl)-1-methanesulfonyl-piperidin-3-yl]-methanone,
[(3S,4S) or (3R,4R)-1-(3-Chloro-benzenesulfonyl)-4-(2,4-difluoro-phenyl)-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4S) or (3R,4R)-4-(2,4-difluoro-phenyl)-1-(2-trifluoromethyl-benzenesulfonyl)-piperidin-3-yl]-methanone,
[4-(5-Chloro-2-methyl-phenyl)-piperazin-1-yl]-[(3S,4S) or (3R,4R)-4-(2,4-difluoro-phenyl)-1-(pyridine-3-sulfonyl)-piperidin-3-yl]-methanone,
[4-(5-Chloro-2-methyl-phenyl)-piperazin-1-yl]-[(3S,4S) or (3R,4R)-4-(2,4-difluoro-phenyl)-1-methanesulfonyl-piperidin-3-yl]-methanone, and
[4-(5-Chloro-2-methyl-phenyl)-piperazin-1-yl]-[(3S,4S) or (3R,4R)-4-(2,4-difluoro-phenyl)-1-(propane-2-sulfonyl)-piperidin-3-yl]-methanone,
and pharmaceutically acceptable salts thereof.

Particularly preferred compounds of formula (I) are those selected from the group consisting of
[4-(2,5-Dimethyl-phenyl)-piperazin-1-yl]-[1-(4-fluoro-2-methyl-phenyl)-4-(3-methoxy-benzenesulfonyl)-piperazin-2-yl]-methanone,
[4-(3-Chloro-benzenesulfonyl)-1-(4-fluoro-2-methyl-phenyl)-piperazin-2-yl]-[4-(2,5-dichloro-phenyl)-piperazin-1-yl]-methanone,
[4-(2,5-Dimethyl-phenyl)-piperazin-1-yl]-[4-(3-methoxy-benzenesulfonyl)-1-phenyl-piperazin-2-yl]-methanone,
[4-(3-Chloro-benzenesulfonyl)-1-o-tolyl-piperazin-2-yl]-[4-(2,5-dimethyl-phenyl)-piperazin-1-yl]-methanone,
[1-Butyl-4-(3-chloro-benzenesulfonyl)-piperazin-2-yl]-[4-(2,5-dimethyl-phenyl)-piperazin-1-yl]-methanone,

[4-(2,5-Dimethyl-phenyl)-piperazin-1-yl]-[1-(4-fluoro-2-methyl-phenyl)-4-(quinoline-8-sulfonyl)-piperazin-2-yl]-methanone,

[4-(2,5-Dichloro-phenyl)-piperazin-1-yl]-[4-(propane-2-sulfonyl)-1-o-tolyl-piperazin-2-yl]-methanone,

[4-(3-Chloro-benzenesulfonyl)-1-(4-fluoro-2-methyl-phenyl)-piperazin-2-yl]-(3',6'-dimethyl-2,3,5,6-tetrahydro-[1,2']bipyrazinyl-4-yl)-methanone,

[4-(3-Chloro-benzenesulfonyl)-1-o-tolyl-piperazin-2-yl]-(3',6'-dimethyl-2,3,5,6-tetrahydro-[1,2']bipyrazinyl-4-yl)-methanone,

[4-(2,5-Dimethyl-phenyl)-piperazin-1-yl]-[(3S,4R)-1-(3-methoxy-benzenesulfonyl)-4-o-tolyl-piperidin-3-yl]-methanone,

[4-(5-Chloro-2-methyl-phenyl)-piperazin-1-yl]-[(3S,4R)-4-(4-fluoro-phenyl)-1-(pyridine-3-sulfonyl)-piperidin-3-yl]-methanone, (3S,4S) or (3R,4R)-[4-(5-Chloro-2-methyl-phenyl)-piperazin-1-yl]-[4-(2-fluoro-4-methyl-phenyl)-1-(2-trifluoromethyl-benzenesulfonyl)-piperidin-3-yl]-methanone,

[(3S,4R)-1-(3-Chloro-benzenesulfonyl)-4-o-tolyl-piperidin-3-yl]-[4-(5-chloro-2-methyl-phenyl)-piperazin-1-yl]-methanone, (3S,4R) or (3R,4S)-[4-(5-Chloro-2-methyl-phenyl)-piperazin-1-yl]-[4-(2,4-difluoro-phenyl)-1-(pyridine-3-sulfonyl)-piperidin-3-yl]-methanone, and

[4-(5-Chloro-2-methyl-phenyl)-piperazin-1-yl]-[(3S,4S) or (3R,4R)-4-(2,4-difluoro-phenyl)-1-methanesulfonyl-piperidin-3-yl]-methanone, and pharmaceutically acceptable salts thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises a) reacting a compound of formula (II)

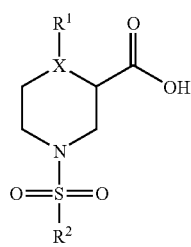

(II)

with a compound of formula (III)

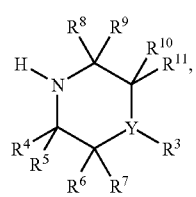

(III)

or b) reacting a compound of formula (IV)

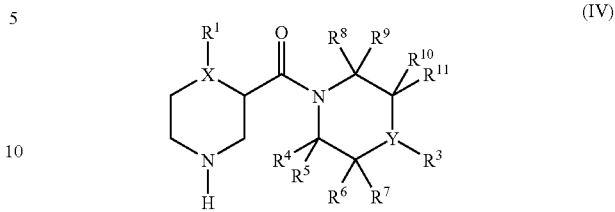

(IV)

with a compound $R^2SO_2Cl$, wherein $R^1, R^2, R^3, R^4, R^5, R^6, R^7, R^8, R^9, R^{10}, R^{11}$, X and Y are as defined above.

The reactions given above can be carried out under conditions well known to the person skilled in the art, e.g. as described below in context with schemes 2, 3 and 4.

The present invention also relates to compounds of formula (I) as defined above, when prepared by a process as described above.

The compounds of formula (I) can be prepared by methods known in the art or as described below in schemes 1 to 4, or in analogy to the methods described below. All starting materials are either commercially available, described in the literature or can be prepared by methods well known in the art or by methods in analogy to those described below. Unless otherwise indicated, $R^1, R^2, R^3, R^4, R^5, R^6, R^7, R^8, R^9, R^{10}, R^{11}$, X and Y are as defined above. As will be understood by those skilled in the art, for the preparation of enantiomerically pure products, enantiomerically pure starting materials should be used. In addition the compounds of formula (I) might be separated into the enantiomerically pure compounds by chromatography on a chiral HPLC column, chromatography with a chiral eluant or by crystallization via diastereomeric salts.

Scheme 1:
X = N

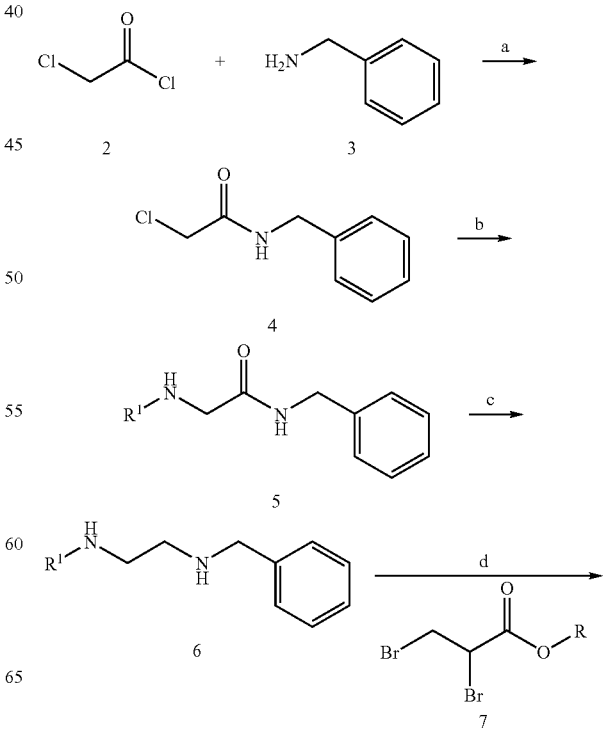

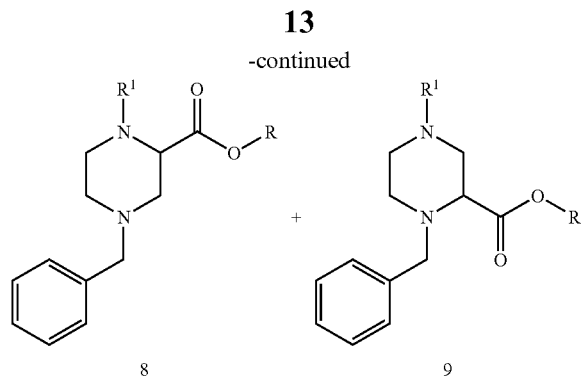

The preparation of the starting materials for piperazine derivatives of formula (I) in which X=N is depicted in scheme 1. The synthesis starts from chloro-acetyl chloride 2 and benzylamine 3 which are converted to N-benzyl-2-chloro-acetamide 4 in the presence of bases such as triethylamine, N,N-diisopropylethylamine or N-ethyl morpholine in solvents such as ether or tetrahydrofuran at room temperature (step a). Compound 4 can be converted to the amine 5 with an excess of the corresponding amine or amino derivative $NH_2R^1$ in a suitable solvent such as DMA, or DMF at RT to 100° C. in the presence of a base such as triethylamine or N,N-diisopropylethylamine (step b). Reduction of compound 5 with borane tetrahydrofuran complex yields amine 6 which is converted to the piperazine derivatives 8 and 9 on treatment with 2,3-dibromopropionic acid esters 7 in the presence of bases such as triethylamine or N,N-diisopropylethylamine in toluene at reflux (steps c, d).

Scheme 2:
X = N

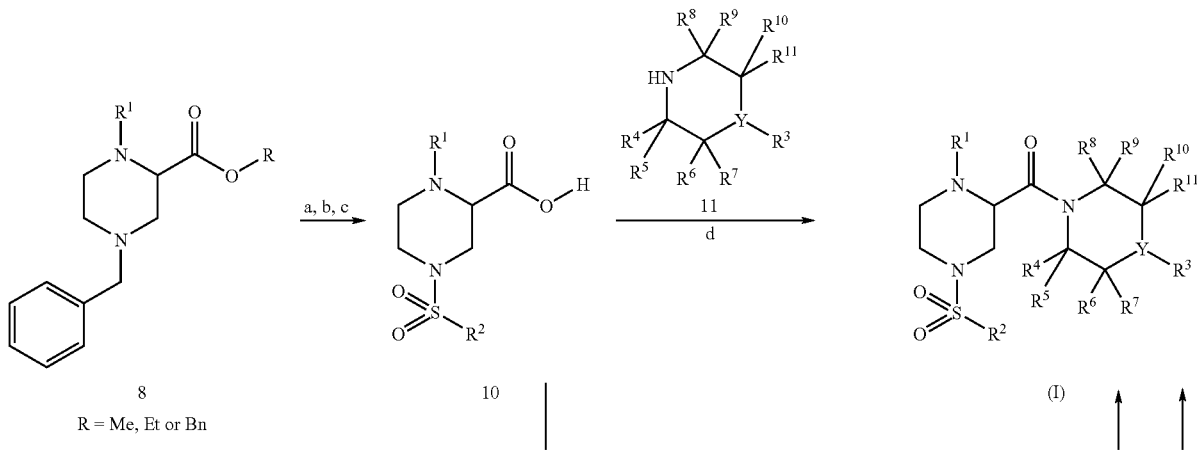

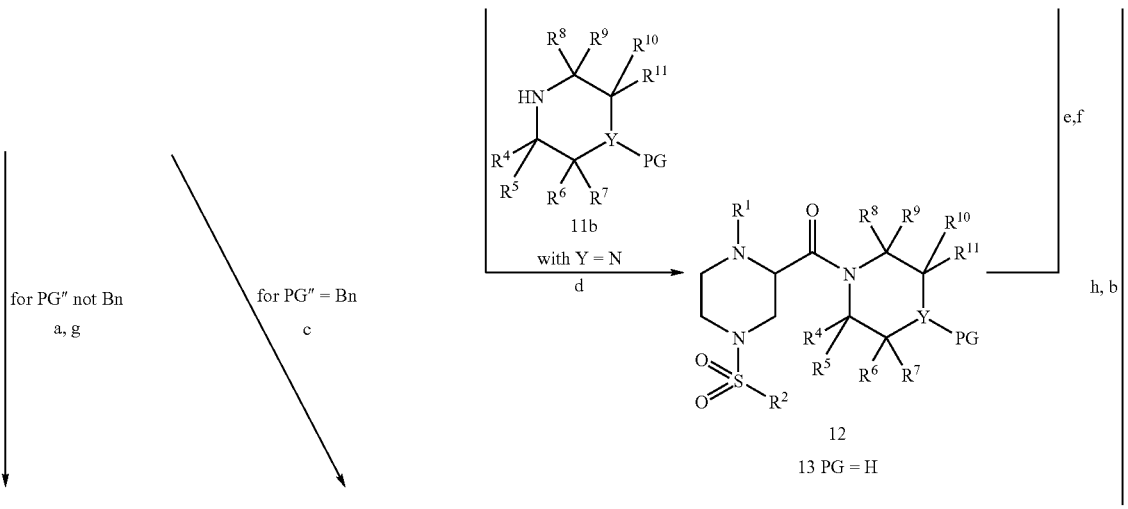

-continued

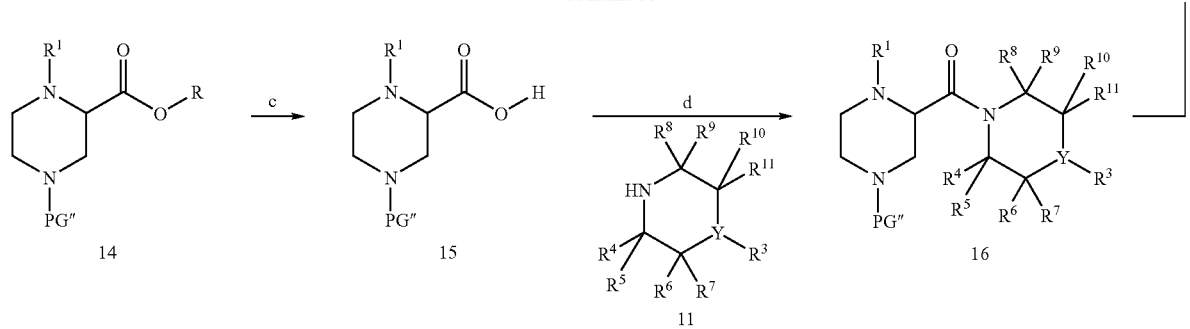

In scheme 2 the synthesis of compounds of the general formula (I) with X=N from intermediate 8 is described. Compound 8 may be transferred into the acid 10 in 3 steps: Cleavage of the benzyl residue by hydrogenation in solvents such as methanol, ethanol, ethyl acetate with Pd/C (step a), sulfonylation of the unprotected piperazine with sulfonyl chlorides in solvents such as dichloromethane, THF, DMF or dioxane with bases such as N-ethyl-diisopropylamine or triethylamine optionally in the presence of DMAP at 0° C. to room temperature (step b), followed by saponification of the ester by treatment with sodium hydroxide or lithium hydroxide in a solvent such as water, methanol, ethanol, tetrahydrofuran or mixtures thereof at temperatures between 0° C. and 60° C.

Condensation of 10 and 11 to compounds of the formula (I) can be achieved by well known procedures for amide formation, using coupling reagents such as N-(3-dimethylaminopropyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N,N-tetra-methyluronium-tetrafluorborate (TPTU), O-(7-azabenzotriazol-1-yl)-1,1,3,3-tetramethyluronium hexafluorophosphate (HATU) or benzotriazol-1-yloxytris(dimethylamino)phosphonium hexafluorophoshate (BOP) in the presence of a base such as ethyl-diisopropylamine, triethylamine, N-methylmorpholine optionally in the presence of 4-dimethylamino-pyridine or 1-hydroxybenzotriazole (HOBt) in solvents such as dichloromethane, dimethylformamide, dimethylacetamide or dioxane at temperatures between 0° C. and ambient temperature (step d). Alternatively, a two-step procedure might be used: treatment of the acid 10 with oxalyl chloride in $CH_2Cl_2$ in the presence of DMF or with thionyl chloride in toluene, followed by reaction with the amine 11. Alternatively acid 10 can be condensed with an amine 11b (for Y=N) to yield the protected compound 12. Cleavage of the protecting group (PG) can be achieved using acidic conditions such as TFA in $CH_2Cl_2$ or HCl in dioxane for BOC-groups (step e). Compound 13 can be converted to compounds of formula (I) by treatment with halo heteroaromatics in the presence of bases such as N,N-diisopropylamine or triethyl amine in solvents such as in DMF or acetonitrile for heteroaromatic moieties $R^3$. For compounds with $R^3$=aryl the Buchwald-Hartwig amination reaction may be used (e.g. aryl-LG (LG=Br, Cl, I, triflate), $Pd(OAc)_2$, 2-(dicyclohexylphosphino)biphenyl, NaOtBu in toluene or tris(dibenzylideneacetone)dipalladium, 2,8,9-triisobutyl-2,5,8,9-tetraaza-1-phosphabicyclo[3.3.3]undecane, sodium tert butylate in toluene).

In an alternative route piperazine derivative 8 is converted into the protected compound 14 by cleavage of the benzyl residue by hydrogenation in solvents such as methanol, ethanol, ethyl acetate with Pd/C (step a), followed by N-BOC-protection with di-tert-butyl dicarbonate in solvents such as ether, THF or $CH_2Cl_2$ optionally in the presence of DMAP at ambient temperature (step g). Alternatively a one pot procedure may be used. Hydrogenation in methanol or ethanol with Pd/C as catalyst in the presence of di-tert-butyl dicarbonate and an amine such as triethyl amine or diisopropylethyl amine yields compound 14 directly. Saponification of the ester 14 or 8 by treatment with sodium hydroxide or lithium hydroxide in a solvent such as water, methanol, ethanol, tetrahydrofuran or mixtures thereof at temperatures between 0° C. and 60° C. yields the acid 15 (step c). Condensation of 15 and 11 to amides 16 can be achieved as described for compound 10 by known procedures of amide formation, using coupling reagents such as N-(3-dimethylaminopropyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N,N-tetramethyluronium-tetrafluorborate (TPTU), O-(7-azabenzotriazol-1-yl)-1,1,3,3-tetramethyluronium hexafluorophosphate (HATU) or benzotriazol-1-yloxytris(dimethylamino)phosphonium hexafluorophoshate (BOP) in the presence of a base such as ethyl-diisopropyl-amine, triethylamine, N-methyl-morpholine optionally in the presence of 4-dimethylamino-pyridine or 1-hydroxybenzo-triazole (HOBt) in solvents such as dichloromethane, dimethylformamide, dimethylacetamide or dioxane at temperatures between 0° C. and ambient temperature (step d). Alternatively, a two-step procedure might be used: treatment of the acid 10 with oxalyl chloride in $CH_2Cl_2$ in the presence of DMF or with thionyl chloride in toluene, followed by reaction with the amine 11. Compounds 16 can be converted to compounds of the formula (I) in two steps: cleavage of the protecting group using acidic conditions such as TFA in $CH_2Cl_2$ or HCl in dioxane for BOC-groups or by hydrogenation in solvents such as methanol, ethanol, ethyl acetate with Pd/C for benzyl moieties (step h), followed by sulfonylation of the unprotected piperazine with sulfonyl chlorides in solvents such as dichloromethane, THF, DMF or dioxane with bases such as N-ethyl-diisopropylamine or triethylamine optionally in the presence of DMAP at 0° C. to room temperature (step b).

Scheme 3:
For X = N

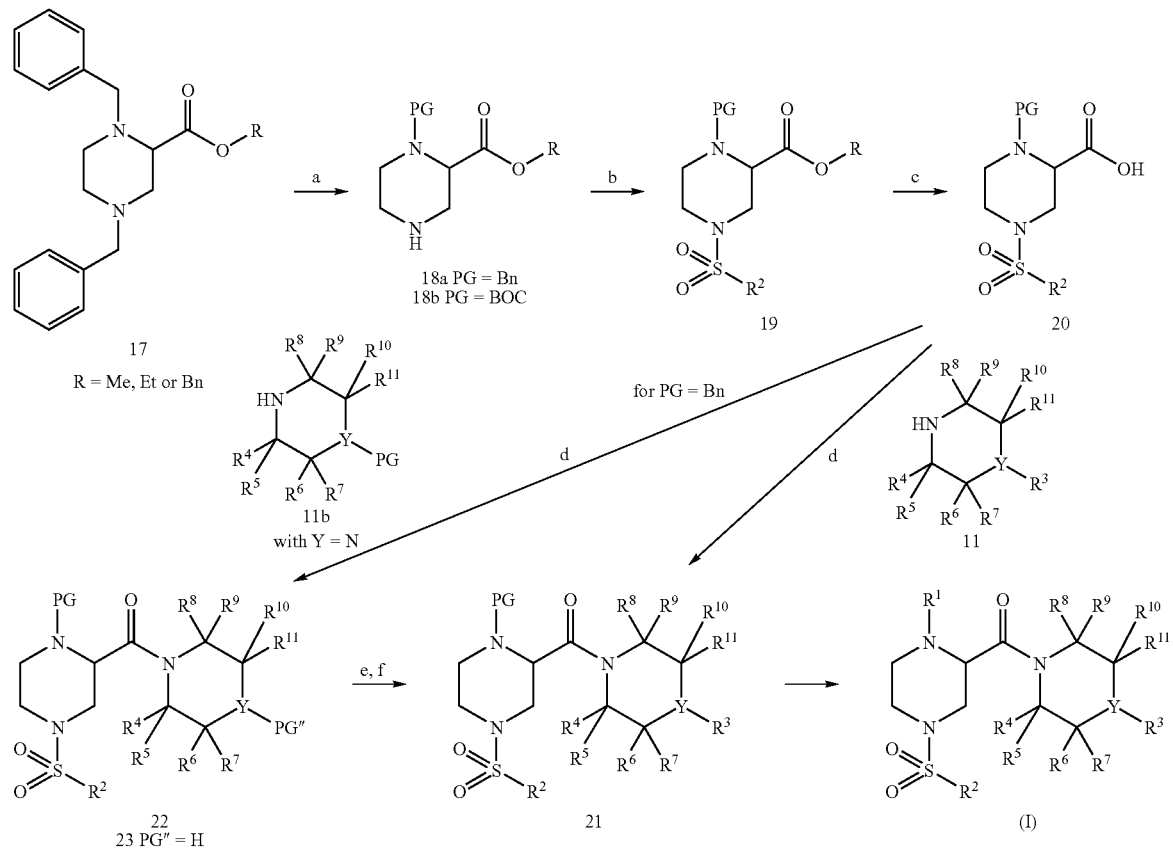

Scheme 3 describes yet another synthetic route to compounds of the formula (I). Monodebenzylation of compound 17 to compound 18a is achieved according to a method described by S. Gubert*, C. Braojos, A. Sacristan, J. A. Ortiz, *Synthesis* 1991, 318 (step a: 1) 1-chloroethyl chloroformate, dichloroethane, reflux; 2) MeOH, reflux). Sulfonylation of the unprotected piperazine 18a or 18b with sulfonyl chlorides in solvents such as dichloromethane, THF, DMF or dioxane with bases such as N-ethyl-diisopropylamine or triethylamine optionally in the presence of DMAP at 0° C. to room temperature (step b), followed by saponification of the ester by treatment with sodium hydroxide or lithium hydroxide in a solvent such as water, methanol, ethanol, tetrahydrofuran or mixtures thereof at temperatures between 0° C. and 60° C. provides acid 20 (step c). Preparation of the amide 21 or 22 can be achieved by condensation of the acid 20 with compound 11 or 11b, respectively, as described for compound 10 by using coupling reagents such as N-(3-dimethylaminopropyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N',N'-tetra-methyluronium-tetra-fluorborate (TPTU), O-(7-azabenzotriazol-1-yl)-1,1,3,3-tetramethyluronium hexafluoro-phosphate (HATU) or benzotriazol-1-yloxytris (dimethylamino)phosphonium hexafluoro-phoshate (BOP) in the presence of a base such as ethyl-diisopropyl-amine, triethylamine, N-methylmorpholine optionally in the presence of 4-dimethylamino-pyridine or 1-hydroxybenzo-triazole (HOBt) in solvents such as dichloromethane, dimethylformamide, dimethylacetamide or dioxane at temperatures between 0° C. and ambient temperature (step d). Cleavage of the protecting group (PG) can be achieved using acidic conditions such as TFA in $CH_2Cl_2$ or HCl in dioxane for BOC-groups (step e). Compound 23 can be converted to compound 21 (step f) by treatment with halo heteroaromatics in the presence of bases such as N,N-diisopropylamine or triethyl amine in solvents such as in DMF or acetonitrile for heteroaromatic moieties $R^3$. For compounds with $R^3$=aryl the Buchwald-Hartwig amination reaction may be used (e.g. $Pd(OAc)_2$, 2-(dicyclohexylphosphino)biphenyl, NaOtBu in toluene or tris(dibenzylideneacetone)dipalladium, 2,8,9-triisobutyl-2,5,8,9-tetraaza-1-phosphabicyclo[3.3.3]undecane, sodium tertbutylate in toluene). Cleavage of the benzyl residue by hydrogenation in solvents such as methanol, ethanol, ethyl acetate with Pd/C (step h), followed by alkylation with $R^1$-LG' (LG'=leaving group such as Cl, Br, I, mesylate, tosylate or triflate) in the presence of a base such as potassium carbonate or cesium carbonate in a solvent such as acetone, DMF or DMA yields compounds (I). For compounds with $R^1$=aryl the Buchwald-Hartwig amination reaction may be used (e.g. aryl-LG (LG=Br, Cl, I, triflate), $Pd(OAc)_2$, 2-(dicyclohexylphosphino)biphenyl, NaOtBu in toluene or tris (dibenzylideneacetone)dipalladium, 2,8,9-triisobutyl-2,5,8,9-tetraaza-1-phosphabicyclo[3.3.3]undecane, sodium tert butylate in toluene).

Scheme 4:
For X = C

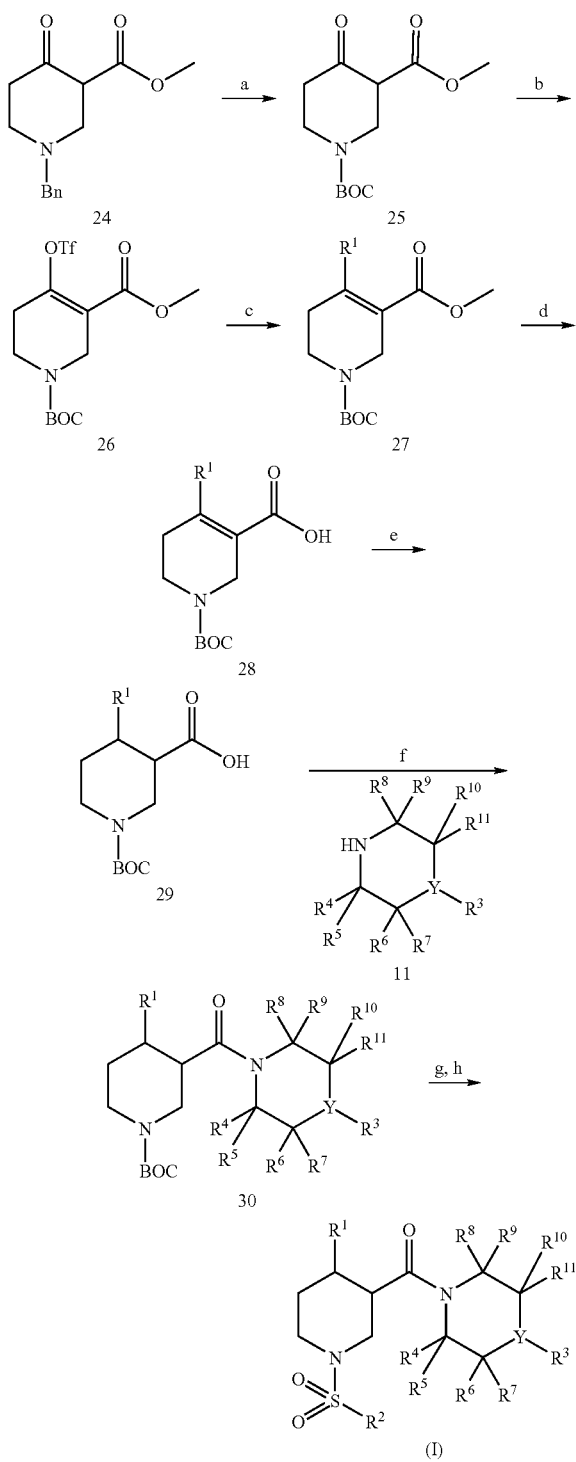

In scheme 4 the preparation of compounds of the formula (I) with X═C is described. Starting from commercially available 24, cleavage of the benzyl residue by hydrogenation in methanol or ethanol with Pd/C as catalyst in the presence of di-tert-butyl dicarbonate and an amine such as triethyl amine of diisopropylethyl amine yields the compound 25 (step a). The enol triflate 26 can be prepared from 25 by treatment with N-phenyltrifluoromethanesulfonimide in the presence of bases such as NaH, KH or NaN(TMS)$_2$ in solvents such as ether, THF or DMF (step b). Palladium catalyzed cross-coupling of enol triflate 26 with organic zinc halides $R^1$ZnBr or $R^1$ZnCl in THF, DMF or mixtures thereof at 65° C. in the presence of bis(dibenzylideneacetone)palladium(0) [Pd(dba)$_2$] and bis(diphenylphosphino)ferrocene (dppf) gives compound 27. Alternatively, $R^1$ boronic acids in the presence of LiCl, bases such as Na$_2$CO$_3$, K$_2$CO$_3$, and catalysts such as tris(dibenzylideneacetone)dipalladium(0) or tetrakis(triphenylphosphine)palladium(0) in 1,2-dimethoxyethane, 1,2-diethoxyethane toluene, or THF, or $R^1$ stannes in the presence of tris(dibenzylideneacetone)dipalladium(0) or tetrakis(triphenylphosphine)palladium(0) in solvents such as THF, ether or toluene can be used (step c). Saponification of the ester 27 by treatment with sodium hydroxide or lithium hydroxide in a solvent such as water, methanol, ethanol, tetrahydrofuran or mixtures thereof at temperatures between 0° C. and 60° C. yields acid 28 (step d). Hydrogenation of acid 28 with Pd/C as catalyst in solvents such as methanol, ethanol, ethyl acetate or THF gives access to the desired intermediate 29 (step e), which may be separated into the cis and trans products. Further separation into the enantiomers can be achieved by chiral HPLC or by crystallization of diastereomeric salts derived from the acids 29 with chiral bases. Enantiomerically enriched or pure cis piperidines ($R^1$=aryl,heteroaryl) may be prepared by enantioselective hydrogenation using a ruthenium catalyst such as [Ru(OAc)$_2$ ((R)-2-furyl)-MeOBIPHEP)], with an additive, for example triethylamine and a solvent, such as methanol for about 42 h at 20-80° C. under 40 bar of hydrogen. The corresponding trans piperidines may be prepared from the cis compounds via selective epimerization of the chiral center a to the carboxyl group using a three step procedure: ester formation under Mitsunobu conditions using an alcohol, triphenylphosphine and diethyl azodicarboxylate (DEAD) or diisopropyl azodicarboxylate (DIAD) in THF, epimerization with sodium alcoholate in toluene under reflux, followed by saponification of the ester under basic conditions by treatment with sodium hydroxide or lithium hydroxide in a solvent such as water, methanol, ethanol, tetrahydrofuran or mixtures thereof.

Preparation of the amide 30 can be achieved by condensation of the acid 29 with compound 11 as described for compound 10 by using coupling reagents such as N-(3-dimethylaminopropyl)-N'-ethyl-carbodiimide-hydrochloride (EDCI), 2-(benzotriazol-1-yl)-N,N,N',N'-tetramethyl-uronium hexafluoro phosphate (HBTU), O-(1,2-dihydro-2-oxo-1-pyridyl)-N,N,N,N-tetra-methyluronium-tetra-fluorborate (TPTU), O-(7-azabenzotriazol-1-yl)-1,1,3,3-tetramethyluronium hexafluoro-phosphate (HATU) or benzotriazol-1-yloxytris(dimethylamino)phosphonium hexafluoro-phosphate (BOP) in the presence of a base such as ethyldiisopropyl-amine, triethylamine, N-methylmorpholine optionally in the presence of 4-dimethylamino-pyridine or 1-hydroxybenzo-triazole (HOBt) in solvents such as dichloromethane, dimethylformamide, dimethylacetamide or dioxane at temperatures between 0° C. and ambient temperature (step f). Cleavage of the protecting group (PG) can be achieved using acidic conditions such as TFA in CH$_2$Cl$_2$ or HCl in dioxane for BOC-groups (step g). Sulfonylation of the unprotected piperidine with sulfonyl chlorides in solvents such as dichloromethane, THF, DMF or dioxane with bases such as N-ethyl-diisopropylamine or triethylamine optionally in the presence of DMAP at 0° C. to room temperature yields the compounds of formula (I) (step h).

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. One method to form such a salt is e.g. by addition of 1/n equivalents of the acid, wherein n=number of acidic protons on the acid, to a solution of the compound in a suitable solvent (e.g. ethanol, ethanol-water mixture, tetrahydrofurane-water mixture) and removal of the solvent by evaporation or lyophilisation.

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment of infectious diseases such as HIV as well as cancer and for prophylaxis of age-related and inherited (e.g. Stargardt's disease) forms of macular degeneration.

The invention therefore also relates to pharmaceutical compositions comprising a compound as defined above and a pharmaceutically acceptable carrier and/or adjuvant. The invention likewise embraces compounds as described above for use as therapeutically active substances, especially as therapeutically active substances for the treatment and/or prophylaxis of diseases which are modulated by LXR alpha and/or LXR beta agonists, particularly as therapeutically active substances for the treatment and/or prophylaxis of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease.

In another preferred embodiment, the invention relates to a method for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease, which method comprises administering a compound as defined above to a human being or animal.

The invention also embraces the use of compounds as defined above for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease.

The invention also relates to the use of compounds as described above for the preparation of medicaments for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease. Such medicaments comprise a compound as described above.

Prevention and/or treatment of increased lipid levels, increased cholesterol levels, atherosclerotic diseases, dyslipidemia, or diabetes is the preferred indication, particularly prevention and/or treatment of increased lipid levels, increased cholesterol levels, atherosclerotic diseases, or dyslipidemia, especially prevention and/or treatment of atherosclerotic diseases or dyslipidemia. Diabetes, particularly non-insulin dependent diabetes mellitus, is another preferred disease.

The following tests were carried out in order to determine the activity of the compounds of the present invention. Background information on the performed assays can be found in: Nichols J S et al. "Development of a scintillation proximity assay for peroxisome proliferator-activated receptor gamma ligand binding domain", Anal Biochem. 1998, 257: 112-119.

Mammalian expression vectors were constructed to express full-length human LXR alpha and LXR beta. Bacterial expression vectors were constructed to produce tagged versions of the ligand binding domains (LBD) of human LXR alpha (aa 164 to 447) and human LXR beta (aa 155 to 460). To accomplish this, the portions of the sequences encoding the LBDs were amplified from the full-length clones by PCR and then subcloned into the plasmid vectors. Final clones were verified by DNA sequence analysis (Willy et al., Genes Dev. 1995, 9:1033-45; Song et al., Proc Natl Acad Sci USA. 1994, 91:10809-13).

Induction, expression, and purification of LBD proteins were performed in *E. coli* strain BL21 (pLysS) cells by standard methods (Ref: Current Protocols in Molecular Biology, Wiley Press, edited by Ausubel et al).

Radioligand Binding Assay

LXR alpha and LXR beta receptor binding were assayed in buffer consisting of 50 mM HEPES, pH 7.4, 10 mM NaCl, 5 mM $MgCl_2$. For each 96-well reaction, 500 ng of LXRα-

LBD or 700 ng of LXR beta-LBD proteins were bound to 80 µg or 40 µg SPA beads respectively, in a final volume of 50 µl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 µl of buffer. Radioligand (eg. 100,000 dpm of (N-(2,2,2-trifluoroethyl)-N-[4-(2,2,2-trifluoro-1-hydroxy-1-trifluoromethylethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using OptiPlates (Packard). Dose response curves were measured within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6-well plate at a density of $10^5$ Cells/well and then batch-transfected with either the full-length-LXRα or full-length-LXRβ expression plasmids plus a reporter plasmid expressing luciferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 µl of phenol red-free medium containing the test substances or control ligands (final DMSO concentration: 0.1%). Following incubation of the cells for 24 hours with substances, 50 µl of the supernatant was discarded and then 50 µl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50 or IC50) of 1 nM to 100 µM, preferably 1 nM to 10 µM, more preferably 1 nM to 1 µM.

For example, the following compounds showed the following IC50 values in the binding assay:

| Example | LXRalpha Binding $IC_{50}$ [µmol/l] | LXRbeta Binding $IC_{50}$ [µmol/l] |
|---|---|---|
| 4 | 18.0 | 0.72 |
| 8 | 4.1 | 0.77 |
| 87 | 15.6 | 2.8 |

These results have been obtained by using the foregoing test.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following examples serve to illustrate the present invention in more detail. They are, however, not intended to limit its scope in any manner.

EXAMPLES

Abbreviations

BOC=t-butyloxycarbonyl, DEAD=diethyl azodicarboxylate, DMF=dimethylformamide, HBTU=2-(benzotriazol-1-yl)-N,N,N',N'-tetramethyl-uronium hexafluoro phosphate, TBME=tert-butyl-methyl ether, THF tetrahydrofuran, TFA=trifluoroacetic acid.

| Ligands: | |
|---|---|
| MeOBIPHEP[1] | (6,6'-Dimethoxy[1,1'-biphenyl]-2,2'-diyl)bis[bis(3,5-di-tert-butyl-4-methoxyphenyl)phosphine) |
| 2-Furyl-MeOBIPHEP[1] | (6,6'-Dimethoxybiphenyl-2,2'-diyl)bis(di-2-furylphosphine) |
| BITIANP[2] | 3,3'-bis-diphenylphosphanyl-1H,1'H-[4,4']-biisothiochromenyl |
| 3,5-Xyl,4-MeO-MeOBIPHEP[1] | (6,6'-Dimethoxy[1,1'-biphenyl]-2,2'-diyl)bis[bis(3,5-di-tert-butyl-4-methoxyphenyl)phosphine) |

[1]Ligands are known in the art and/or can be prepared according to the examples or methods as described in EP 0 398 132, WO 92/16535, EP 0 104 375 or EP 0 580 331.
[2]Benincori, T.; Brenna, E.; Sannicolo, F.; Trimarco, L.; Antognazza, P.; Cesarotti, E.; Demartin, F.; Pilati, T. *J. Org. Chem.* 1996, 61, 6244.

Example 1

[4-(2,5-Dimethyl-phenyl)-piperazin-1-yl]-[1-(4-fluoro-2-methyl-phenyl)-4-(3-methoxy-benzene-sulfonyl)-piperazin-2-yl]-methanone

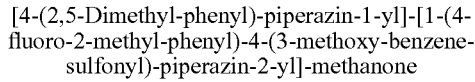

Step 1: 4-(4-fluoro-2-methyl-phenyl)-piperazine-1,3-dicarboxylic acid 1-tert-butyl ester (CAS Reg. No.: [499780-10-8]) (100 mg) in DMF (2.5 mL) was treated with 1-(2,5-dimethylphenyl)piperazine (62 mg), 2-(benzotriazol-1-yl)-N,N,N',N'-tetramethyl-uronium hexafluoro phosphate (HBTU) (123 mg) and triethylamine (124 µL) at ambient temperature for 5 h. Water was added, the phases were separated and the inorganic phase was extracted with tert-butyl-methyl ether (TBME). The combined organic phases were washed with water and brine, dried (Na$_2$SO$_4$), filtered and evaporated. Purification by chromatography (SiO$_2$, n-heptane/ethyl acetate 2:1) gave 3-[4-(2,5-dimethyl-phenyl)-piperazine-1-carbonyl]-4-(4-fluoro-2-methyl-phenyl)-piperazine-1-carboxylic acid tert-butyl ester as a white solid (143 mg), MS: 511.5 ([M+H]$^+$).

Step 2: To a solution of 3-[4-(2,5-dimethyl-phenyl)-piperazine-1-carbonyl]-4-(4-fluoro-2-methyl-phenyl)-piperazine-1-carboxylic acid tert-butyl ester (133 mg) in ethanol (5 mL) was added a saturated solution of hydrogen chloride in ethanol (1 mL). The mixture was stirred at room temperature for 2 h, and was concentrated to give [4-(2,5-dimethyl-phenyl)-piperazin-1-yl]-[1-(4-fluoro-2-methyl-phenyl)-piperazin-2-yl]-methanone hydrochloride as crude white solid, MS: 411.5 ([M+H]$^+$).

Step 3: To a solution of [4-(2,5-dimethyl-phenyl)-piperazin-1-yl]-[1-(4-fluoro-2-methyl-phenyl)-piperazin-2-yl]-methanone hydrochloride (42 mg) in DMF (1 mL) was added 3-methoxybenzene sulfonyl chloride (21.4 mg) and triethyl amine (40 µL). The reaction mixture was stirred at ambient temperature for 2 h, was diluted with ethyl acetate and washed with a saturated aqueous solution of NaHCO$_3$. The combined organic phases were washed with water and brine, dried (Na$_2$SO$_4$), filtered and evaporated. The crude product was purified by column chromatography (SiO$_2$, n-heptane/ethyl acetate 2:1) to give [4-(2,5-dimethyl-phenyl)-piperazin-1-yl]-[1-(4-fluoro-2-methyl-phenyl)-4-(3-methoxy-benzene-sulfonyl)-piperazin-2-yl]-methanone (42 mg) as white solid, MS: 581.3 ([M+H]$^+$).

Example 2

[4-(3-Chloro-benzenesulfonyl)-1-(4-fluoro-2-methyl-phenyl)-piperazin-2-yl]-[4-(2,5-dimethyl-phenyl)-piperazin-1-yl]-methanone

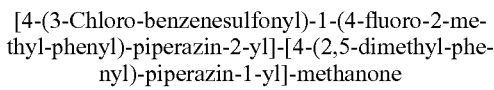

Step 1: To a solution of benzylamine (60.3 mL) and triethylamine (96.3 mL) in THF (800 mL) was added chloroacetyl chloride (45.8 mL) at 0° C. The reaction mixture was allowed to warm to room temperature over night. Additional chloroacetyl chloride (4.6 mL) was added and stirring was continued until no starting material could be detected. The reaction mixture was filtered, washed with ethyl acetate and concentrated. The crude product was crystallized from dichloromethane to yield N-benzyl-2-chloro-acetamide (71.6 g) as off-white solid.

Step 2: To a solution of N-benzyl-2-chloro-acetamide (20 g) in DMF (200 mL) were added 4-fluoro-2-methylaniline (13.3 mL) and N,N-diisopropylethylamine (22.2 mL). The reaction mixture was heated to 100° C. over night, cooled to room temperature, and the mixture was diluted with ethyl acetate and washed with water. The combined inorganic phases were extracted with ethyl acetate and the combined organic phases were dried (Na$_2$SO$_4$), filtered and evaporated. The crude product was purified by chromatography (SiO$_2$, n-heptane/ethyl acetate 1:2) to give N-benzyl-2-(4-fluoro-2-methyl-phenylamino)-acetamide (20 g) as grey solid, MS: 273.0 ([M+H]$^+$).

Step 3: To a solution of N-benzyl-2-(4-fluoro-2-methyl-phenylamino)-acetamide (17 g) in THF (500 mL) was added a solution of borane tetrahydrofuran complex (499.4 mL, 1M in THF). The solution was heated to reflux for 4 h, was concentrated and redissolved in a mixture of 2M HCl and TBME. The inorganic phase was extracted with TBME, the organic phases washed with 2M HCl. The pH of the combined inorganic phases was adjusted to pH 11 by the addition of concentrated NaOH, and the solution was extracted with TBME. The combined organic phases were dried (Na$_2$SO$_4$), filtered and evaporated to yield N-benzyl-N'-(4-fluoro-2-methyl-phenyl)-ethane-1,2-diamine (15.1 g) as a crude product, MS: 259.3 ([M+H]$^+$).

Step 4: To N-benzyl-N'-(4-fluoro-2-methyl-phenyl)-ethane-1,2-diamine (15.1 g) in toluene (150 mL) was added N,N-diisopropylethylamine (33.8 mL) and 2,3-dibromopropionic acid ethyl ester (25.61 mL) in toluene (350 mL). The reaction mixture was heated to 135° C. for 18 h, cooled to room temperature, and the precipitated solid was removed by filtration. The solution was concentrated, and the crude material was redissolved in TBME and washed with an aqueous 2M solution of Na$_2$CO$_3$ and brine, dried (Na$_2$SO$_4$), filtered and evaporated. Chromatography (SiO$_2$, n-heptane/ethyl acetate 97:3) gave 4-benzyl-1-(4-fluoro-2-methyl-phenyl)-piperazine-2-carboxylic acid ethyl ester (5.5 g) as yellow oil, MS: 357.3 ([M+H]$^+$) and 1-benzyl-4-(4-fluoro-2-methyl-phenyl)-piperazine-2-carboxylic acid ethyl ester (3.3 g) as yellow oil, MS: 357.1 ([M+H]$^+$).

Step 5: 4-Benzyl-1-(4-fluoro-2-methyl-phenyl)-piperazine-2-carboxylic acid ethyl ester (1 g) in ethyl acetate (10 mL) was hydrogenated in the presence of 10% Pd/C (149 mg) and acetic acid (1 mL). After removal of the catalyst and evaporation of the solvent, the residue was dissolved in DMF (8 mL) and was treated with 3-chlorobenzenesulfonyl chloride (280 µL) and triethylamine (1.96 mL) at ambient temperature until no starting material could be detected by TLC. The mixture was diluted with ethyl acetate and washed with an aqueous solution of NaHCO$_3$, dried (Na$_2$SO$_4$), filtered and evaporated. Purification by chromatography (SiO$_2$, n-heptane/ethyl acetate 2:1) yielded 4-(3-chloro-benzenesulfonyl)-1-(4-fluoro-2-methyl-phenyl)-piperazine-2-carboxylic acid ethyl ester as a white solid (750 mg), MS: 441.3 ([M+H, 1Cl]$^+$).

Step 6: To a solution of 4-(3-chloro-benzenesulfonyl)-1-(4-fluoro-2-methyl-phenyl)-piperazine-2-carboxylic acid ethyl ester (730 mg) in tetrahydrofuran (20 mL) was added 1 M aqueous LiOH solution (16.6 mL) and methanol until a clear solution was obtained. The mixture was stirred at reflux for 1 h, 1M KHSO$_4$ (20 mL) was added and the inorganic phase was extracted with ethyl acetate. The combined organic phases were dried (Na$_2$SO$_4$), filtered and evaporated to yield 4-(3-chloro-benzenesulfonyl)-1-(4-fluoro-2-methyl-phenyl)-piperazine-2-carboxylic acid as a light yellow solid, MS: 411.0 ([M−H, 1Cl]$^-$).

Step 7: In analogy to example 1, step 1, from 4-(3-chloro-benzenesulfonyl)-1-(4-fluoro-2-methyl-phenyl)-piperazine-2-carboxylic acid, 1-(2,5-dimethylphenyl)-piperazine, HBTU and triethylamine in DMF was prepared [4-(3-chloro-benzenesulfonyl)-1-(4-fluoro-2-methyl-phenyl)-piperazin-2-yl]-[4-(2,5-dimethyl-phenyl)-piperazin-1-yl]-methanone as a white solid, MS: 584.7 ([M+H, 1Cl]$^+$).

Example 3

[4-(3-Chloro-benzenesulfonyl)-1-(4-fluoro-2-methyl-phenyl)-piperazin-2-yl]-[4-(5-chloro-2-methyl-phenyl)-piperazin-1-yl]-methanone In analogy to example 1, step 1, from 4-(3-chloro-benzenesulfonyl)-1-(4-fluoro-2-methyl-phenyl)-piperazine-2-carboxylic acid and 1-(5-chloro-ortho-tolyl)-piperazine was prepared [4-(3-chloro-benzenesulfonyl)-1-(4-fluoro-2-methyl-phenyl)-piperazin-2-yl]-[4-(5-chloro-2-methyl-phenyl)-piperazin-1-yl]-methanone as a white solid, MS: 604.8 ([M+H, 1Cl]$^+$).

Example 4

[4-(3-Chloro-benzenesulfonyl)-1-(4-fluoro-2-methyl-phenyl)-piperazin-2-yl]-[4-(2,5-dichloro-phenyl)-piperazin-1-yl]-methanone In analogy to example 1, step 1, from 4-(3-chloro-benzenesulfonyl)-1-(4-fluoro-2-methyl-phenyl)-piperazine-2-carboxylic acid and 1-(2,5-dichlorophenyl)-piperazine dihydrochloride was prepared [4-(3-chloro-benzenesulfonyl)-1-(4-fluoro-2-methyl-phenyl)-piperazin-2-yl]-[4-(2,5-dichloro-phenyl)-piperazin-1-yl]-methanone as a white solid, MS: 624.5 ([M+H, 1Cl]$^+$).

Example 5

(−)-[4-(3-Chloro-benzenesulfonyl)-1-(4-fluoro-2-methyl-phenyl)-piperazin-2-yl]-[4-(2,5-dichloro-phenyl)-piperazin-1-yl]-methanone

[4-(3-Chloro-benzenesulfonyl)-1-(4-fluoro-2-methyl-phenyl)-piperazin-2-yl]-[4-(2,5-dichloro-phenyl)-piperazin-1-yl]-methanone (example 4) was separated into the enantiomers by chiral HPLC on Chiralpak AD using n-heptane/30% ethanol as the mobile phase to give (+)-[4-(3-chloro-benzenesulfonyl)-1-(4-fluoro-2-methyl-phenyl)-piperazin-2-yl]-[4-(2,5-dichloro-phenyl)-piperazin-1-yl]-methanone as an off-white solid, MS: 624.5 ([M+H, 1Cl]$^+$) and (−)-[4-(3-chloro-benzenesulfonyl)-1-(4-fluoro-2-methyl-phenyl)-piperazin-2-yl]-[4-(2,5-dichloro-phenyl)-piperazin-1-yl]-methanone as an off-white solid, MS: 624.5 ([M+H, 1Cl]$^+$).

Example 6

[4-(3-Chloro-benzenesulfonyl)-1-(4-fluoro-2-methyl-phenyl)-piperazin-2-yl]-(4-o-tolyl-piperazin-1-yl)-methanone In analogy to example 1, step 1, from 4-(3-chloro-benzenesulfonyl)-1-(4-fluoro-2-methyl-phenyl)-piperazine-2-carboxylic acid and 1-(2-methylphenyl)piperazine was prepared [4-(3-chloro-benzenesulfonyl)-1-(4-fluoro-2-methyl-phenyl)-piperazin-2-yl]-(4-o-tolyl-piperazin-1-yl)-methanone as a light yellow foam, MS: 571.2 ([M+H, 1Cl]$^+$).

Example 7

[4-(2,5-Dichloro-phenyl)-piperazin-1-yl]-[4-(3-methoxy-benzenesulfonyl)-1-phenyl-piperazin-2-yl]-methanone Steps 1-4: In analogy to example 2, steps 1-4, from benzylamine, chloroacetyl chloride, aniline and 2,3-dibromopropionic acid ethyl ester was prepared 4-benzyl-1-phenyl-piperazine-2-carboxylic acid ethyl ester as a light yellow oil, MS: 325.5 ([M+H]$^+$).

Step 5: In analogy to example 2, step 5, from 4-benzyl-1-phenyl-piperazine-2-carboxylic acid ethyl ester and 3-methoxy-benzenesulfonyl chloride was prepared 4-(3-methoxy-benzenesulfonyl)-1-phenyl-piperazine-2-carboxylic acid ethyl ester as a light yellow oil, MS: 405.3 ([M+H]$^+$).

Step 6: In analogy to example 2, step 6, from 4-(3-methoxy-benzenesulfonyl)-1-phenyl-piperazine-2-carboxylic acid ethyl ester was prepared 4-(3-methoxy-benzenesulfonyl)-1-phenyl-piperazine-2-carboxylic acid as an off white solid, MS: 375.5 ([M+H]$^+$).

Step 7: In analogy to example 1, step 1, from 4-(3-methoxy-benzenesulfonyl)-1-phenyl-piperazine-2-carboxylic acid and 1-(2,5-dichlorophenyl)piperazine dihydrochloride was prepared [4-(2,5-dichloro-phenyl)-piperazin-1-yl]-[4-(3-methoxy-benzenesulfonyl)-1-phenyl-piperazin-2-yl]-methanone as a white solid, MS: 589.0 ([M+H, 1Cl]$^+$).

Example 8

[4-(2,5-Dimethyl-phenyl)-piperazin-1-yl]-[4-(3-methoxy-benzenesulfonyl)-1-phenyl-piperazin-2-yl]-methanone In analogy to example 1, step 1, from 4-(3-methoxy-benzenesulfonyl)-1-phenyl-piperazine-2-carboxylic acid and 1-(2,5-dimethylphenyl)piperazine was prepared [4-(2,5-dimethyl-phenyl)-piperazin-1-yl]-[4-(3-methoxy-benzenesulfonyl)-1-phenyl-piperazin-2-yl]-methanone as a white solid, MS: 548.8 ([M+H]$^+$).

Example 9

[4-(5-Chloro-2-methyl-phenyl)-piperazin-1-yl]-[4-(3-methoxy-benzenesulfonyl)-1-phenyl-piperazin-2-yl]-methanone In analogy to example 1, step 1, from 4-(3-methoxy-benzenesulfonyl)-1-phenyl-piperazine-2-carboxylic acid and 1-(5-chloro-2-methylphenyl)-piperazine was prepared [4-(5-chloro-2-methyl-phenyl)-piperazin-1-yl]-[4-(3-methoxy-benzenesulfonyl)-1-phenyl-piperazin-2-yl]-methanone as a white solid, MS: 568.8 ([M+H, 1Cl]$^+$).

Example 10

[4-(3-Chloro-benzenesulfonyl)-1-o-tolyl-piperazin-2-yl]-[4-(2,5-dichloro-phenyl)-piperazin-1-yl]-methanone Steps 1-4: In analogy to example 2, steps 1-4, from benzylamine, chloroacetyl chloride, o-toluidine and 2,3-dibromopropionic acid ethyl ester was prepared 4-benzyl-1-o-tolyl-piperazine-2-carboxylic acid ethyl ester as an orange oil, MS: 339.4 ([M+H]$^+$).

Step 5: In analogy to example 2, step 5, from 4-benzyl-1-o-tolyl-piperazine-2-carboxylic acid ethyl ester and 3-chlorobenzenesulfonyl chloride was prepared 4-(3-chloro-benzenesulfonyl)-1-o-tolyl-piperazine-2-carboxylic acid ethyl ester as a white solid, MS: 422.9 ([M+H, 1Cl]$^+$).

Step 6: In analogy to example 2, step 6, from 4-(3-chloro-benzenesulfonyl)-1-o-tolyl-piperazine-2-carboxylic acid ethyl ester was prepared 4-(3-chloro-benzenesulfonyl)-1-o-tolyl-piperazine-2-carboxylic acid as a light yellow solid, MS: 393.3 ([M−H, 1Cl]$^−$).

Step 7: In analogy to example 1, step 1, from 4-(3-chloro-benzenesulfonyl)-1-o-tolyl-piperazine-2-carboxylic acid and 1-(2,5-dichlorophenyl)-piperazine dihydrochloride was prepared [4-(3-chloro-benzenesulfonyl)-1-o-tolyl-piperazin-2-yl]-[4-(2,5-dichloro-phenyl)-piperazin-1-yl]-methanone as a white solid, MS: 606.6 ([M+H, 1Cl]$^+$).

Example 11

[4-(3-Chloro-benzenesulfonyl)-1-o-tolyl-piperazin-2-yl]-[4-(5-chloro-2-methyl-phenyl)-piperazin-1-yl]-methanone In analogy to example 1, step 1, from 4-(3-chloro-benzenesulfonyl)-1-o-tolyl-piperazine-2-carboxylic acid and 1-(5-chloro-ortho-tolyl)-piperazine was prepared [4-(3-chloro-benzenesulfonyl)-1-o-tolyl-piperazin-2-yl]-[4-(5-chloro-2-methyl-phenyl)-piperazin-1-yl]-methanone as a light yellow solid, MS: 586.8 ([M+H, 1Cl]$^+$).

Example 12

[4-(3-Chloro-benzenesulfonyl)-1-o-tolyl-piperazin-2-yl]-[4-(2,5-dimethyl-phenyl)-piperazin-1-yl]-methanone In analogy to example 1, step 1, from 4-(3-chloro-benzenesulfonyl)-1-o-tolyl-piperazine-2-carboxylic acid and 1-(2,5-dimethylphenyl)-piperazine was prepared [4-(3-chloro-benzenesulfonyl)-1-o-tolyl-piperazin-2-yl]-[4-(2,5-dimethyl-phenyl)-piperazin-1-yl]-methanone as a light yellow solid, MS: 567.3 ([M+H, 1 Cl]$^+$).

Example 13

[1-Benzyl-4-(3-methoxy-benzenesulfonyl)-piperazin-2-yl]-[4-(2,5-dimethyl-phenyl)-piperazin-1-yl]-methanone Step 1: Under argon at 0° C., to a solution of ethyl 1,4-dibenzylpiperazine-2-carboxylate (10 g) in dichloroethane (40 mL) a solution of 1-chloroethyl chloroformate (4.73 mL) in dichloroethane (14 mL) was added dropwise over a period of 10 min. The reaction mixture was stirred for 15 minutes at 0° C., and then heated to reflux overnight. The solvent was evaporated and the crude material was dissolved in ethanol and heated at reflux overnight. The solvent was evaporated and the residue was dissolved in water and extracted with diethyl ether (×2) and CH$_2$Cl$_2$ (×2). A saturated solution of NaHCO$_3$ was then added to the water phase, and the inorganic phase was extracted with CH$_2$Cl$_2$ (×2). The organic layers were then combined, washed with brine, dried (Na$_2$SO$_4$), filtered and concentrated to give 1-benzyl-piperazine-2-carboxylic acid ethyl ester as crude product, MS: 248.9 ([M+H]$^+$).

Step 2: A solution of 1-benzyl-piperazine-2-carboxylic acid ethyl ester (300 mg) in DMF (13 mL) was treated with triethylamine (0.5 mL) and 3-methoxybenzene sulfonyl chloride (274.6 mg) at RT for 2 hours. Water was added, and the inorganic layer was extracted with ethyl acetate (×3). The combined organic layers were dried (Na$_2$SO$_4$), filtered and evaporated to yield 1-benzyl-4-(3-methoxy-benzenesulfonyl)-piperazine-2-carboxylic acid ethyl ester as a colorless oil (417 mg), MS: 419.3 ([M+H]$^+$).

Step 3: In analogy to example 2, step 6, from 1-benzyl-4-(3-methoxy-benzenesulfonyl)-piperazine-2-carboxylic acid ethyl ester was prepared 1-benzyl-4-(3-methoxy-benzenesulfonyl)-piperazine-2-carboxylic acid, which was subjected to the next reaction without further purification. MS: 389.5 ([M−H]$^−$).

Step 4: In analogy to example 1, step 1, from 1-benzyl-4-(3-methoxy-benzenesulfonyl)-piperazine-2-carboxylic acid and 1-(2,5-dimethylphenyl)piperazine was prepared [1-benzyl-4-(3-methoxy-benzenesulfonyl)-piperazin-2-yl]-[4-(2,5-dimethyl-phenyl)-piperazin-1-yl]-methanone as a white foam, MS: 563.5 ([M+H]$^+$).

Example 14

(−)-[1-Benzyl-4-(3-methoxy-benzenesulfonyl)-piperazin-2-yl]-[4-(2,5-dimethyl-phenyl)-piperazin-1-yl]-methanone 1-Benzyl-4-(3-methoxy-benzenesulfonyl)-piperazin-2-yl]-[4-(2,5-dimethyl-phenyl)-piperazin-1-yl]-methanone was separated into the enantiomers by chiral HPLC on Chiralpak AD using n-heptane/25% isopropanol as the mobile phase to give (+)-[1-benzyl-4-(3-methoxy-benzenesulfonyl)-piperazin-2-yl]-[4-(2,5-dimethyl-phenyl)-piperazin-1-yl]-methanone as a colorless oil, MS: 563.3 ([M+H]$^+$ and (−)-[1-benzyl-4-(3-methoxy-benzenesulfonyl)-piperazin-2-yl]-[4-(2,5-dimethyl-phenyl)-piperazin-1-yl]-methanone as a colorless oil, MS: 563.3 ([M+H]$^+$).

Example 15

[1-Benzyl-4-(3-chloro-benzenesulfonyl)-piperazin-2-yl]-[4-(2,5-dimethyl-phenyl)-piperazin-1-yl]-methanone Step 1: In analogy to example 1, step 1, from 1,4-dibenzylpiperazine-2-carboxylic acid (CAS Reg. No.: [215597-67-4]) and 1-(2,5-dimethylphenyl)piperazine was prepared (1,4-dibenzyl-piperazin-2-yl)-[4-(2,5-dimethyl-phenyl)-piperazin-1-yl]-methanone as a white foam, MS: 483.3 ([M+H]$^+$).

Step 2: In analogy to example 13, steps 1-2, from (1,4-dibenzyl-piperazin-2-yl)-[4-(2,5-dimethyl-phenyl)-piperazin-1-yl]-methanone and 3-chlorobenzene sulfonyl chloride was prepared [1-benzyl-4-(3-chloro-benzenesulfonyl)-piperazin-2-yl]-[4-(2,5-dimethyl-phenyl)-piperazin-1-yl]-methanone as a white foam, MS: 567.3 ([M+H, 1Cl]$^+$).

Example 16

[1-Benzyl-4-(3,5-dimethyl-isoxazole-4-sulfonyl)-piperazin-2-yl]-[4-(2,5-dimethyl-phenyl)-piperazin-1-yl]-methanone In analogy to example 13 steps 1-2, from (1,4-dibenzyl-piperazin-2-yl)-[4-(2,5-dimethyl-phenyl)-piperazin-1-yl]- methanone and 3,5-dimethylisoxazole-4-sulfonyl chloride was prepared [1-benzyl-4-(3,5-dimethyl-isoxazole-4-sulfonyl)-piperazin-2-yl]-[4-(2,5-dimethyl-phenyl)-piperazin-1-yl]-methanone as a white foam, MS: 552.3 ([M+H]$^+$).

Example 17

[4-(3-Chloro-benzenesulfonyl)-1-propyl-piperazin-2-yl]-[4-(2,5-dimethyl-phenyl)-piperazin-1-yl]-methanone Step 1: To a solution of N-1-Boc-2-piperazinecarboxylic acid methyl ester (CAS Reg. No: [129799-15-1]) (1 g) in DMF (5 mL) was added 3-chlorobenzenesulfonyl chloride (0.95 g) and triethylamine (1.71 mL). The reaction mixture was stirred at RT overnight. Water was added and the mixture was extracted with ethyl acetate (×2). The combined organic layers were washed with water (×2) and brine, were dried (Na$_2$SO$_4$), filtered and evaporated. Purification by chromatography (SiO$_2$, n-heptane/ethyl acetate 3:1) yielded 4-(3-chloro-benzenesulfonyl)-piperazine-1,2-dicarboxylic acid 1-tert-butyl ester 2-methyl ester as white foam (1.66 g), MS: 436.3 ([M+NH$_4$, 1Cl]$^+$).

Step 2: In analogy to example 2, step 6 (ambient temperature), from 4-(3-chloro-benzenesulfonyl)-piperazine-1,2-dicarboxylic acid 1-tert-butyl ester 2-methyl ester was prepared 4-(3-chloro-benzenesulfonyl)-piperazine-1,2-dicarboxylic acid 1-tert-butyl ester as a white foam, MS: 403.2 ([M−H, 1Cl]$^−$).

Step 3: In analogy to example 1, step 1, from 4-(3-chloro-benzenesulfonyl)-piperazine-1,2-dicarboxylic acid 1-tert-butyl ester and 1-(2,5-dimethylphenyl)-piperazine was prepared 4-(3-chloro-benzenesulfonyl)-2-[4-(2,5-dimethyl-phenyl)-piperazine-1-carbonyl]-piperazine-1-carboxylic acid tert-butyl ester as a white foam, MS: 577.4 ([M+H, 1Cl]$^+$).

Step 4: To a solution of 4-(3-chloro-benzenesulfonyl)-2-[4-(2,5-dimethyl-phenyl)-piperazine-1-carbonyl]-piperazine-1-carboxylic acid tert-butyl ester (2.18 g) in ethanol (21.8 mL) was added a saturated solution of HCl in ethanol (21.8 mL) at 0° C. The reaction mixture was stirred at ambient temperature overnight, the solution was concentrated and the residue dissolved in a mixture of NaHCO$_3$ solution and ethyl acetate. The inorganic phase was extracted with ethyl acetate (×3) and the combined organic layers were washed with brine, dried (Na$_2$SO$_4$), filtered and evaporated to yield [4-(3-chloro-benzenesulfonyl)-piperazin-2-yl]-[4-(2,5-dimethyl-phenyl)-piperazin-1-yl]-methanone as crude product (1.79 g), MS: 477.0 ([M+H, 1Cl]$^+$).

Step 5: To a solution of [4-(3-chloro-benzenesulfonyl)-piperazin-2-yl]-[4-(2,5-dimethyl-phenyl)-piperazin-1-yl]-methanone (100 mg) in acetone (4 mL) was added cesium carbonate (82 mg), followed by 1-bromopropane (21 µL). The reaction mixture was stirred at reflux overnight. Water was added and the reaction mixture was extracted with ethyl acetate (×2). The combined organic layers were washed with brine, dried (Na$_2$SO$_4$), filtered and evaporated. Purification by chromatography (SiO$_2$, n-heptane/ethyl acetate 3:1) yielded [4-(3-chloro-benzenesulfonyl)-1-propyl-piperazin-2-yl]-[4-(2,5-dimethyl-phenyl)-piperazin-1-yl]-methanone as a white foam (75 mg), MS: 519.3 ([M+H, 1Cl]$^+$).

Example 18

[1-Butyl-4-(3-chloro-benzenesulfonyl)-piperazin-2-yl]-[4-(2,5-dimethyl-phenyl)-piperazin-1-yl]-methanone In analogy to example 17, step 5, from [4-(3-chloro-benzenesulfonyl)-piperazin-2-yl]-[4-(2,5-dimethyl-phenyl)-piperazin-1-yl]-methanone and 1-bromobutane was prepared [1-butyl-4-(3-chloro-benzenesulfonyl)-piperazin-2-yl]-[4-(2,5-dimethyl-phenyl)-piperazin-1-yl]-methanone as a white foam, MS: 533.4 ([M+H, 1Cl]$^+$).

Example 19

[4-(3-Chloro-benzenesulfonyl)-1-pentyl-piperazin-2-yl]-[4-(2,5-dimethyl-phenyl)-piperazin-1-yl]-methanone In analogy to example 17, step 5, from [4-(3-chloro-benzenesulfonyl)-piperazin-2-yl]-[4-(2,5-dimethyl-phenyl)-piperazin-1-yl]-methanone and 1-bromopentane was prepared [4-(3-chloro-benzenesulfonyl)-1-pentyl-piperazin-2-yl]-[4-(2,5-dimethyl-phenyl)-piperazin-1-yl]-methanone as a white foam, MS: 547.3 ([M+H, 1Cl]$^+$).

Example 20

[4-(3-Chloro-benzenesulfonyl)-1-isobutyl-piperazin-2-yl]-[4-(2,5-dimethyl-phenyl)-piperazin-1-yl]-methanone In analogy to example 17, step 5, from [4-(3-chloro-benzenesulfonyl)-piperazin-2-yl]-[4-(2,5-dimethyl-phenyl)-piperazin-1-yl]-methanone and 1-bromo-2-methylpropane was prepared [4-(3-chloro-benzenesulfonyl)-1-isobutyl-piperazin-2-yl]-[4-(2,5-dimethyl-phenyl)-piperazin-1-yl]-methanone as a white foam, MS: 533.2 ([M+H, 1Cl]$^+$).

Example 21

[4-(3-Chloro-benzenesulfonyl)-1-phenethyl-piperazin-2-yl]-[4-(2,5-dimethyl-phenyl)-piperazin-1-yl]-methanone In analogy to example 17, step 5, from [4-(3-chloro-benzenesulfonyl)-piperazin-2-yl]-[4-(2,5-dimethyl-phenyl)-piperazin-1-yl]-methanone and (2-bromoethyl)-benzene was prepared [4-(3-chloro-benzenesulfonyl)-1-phenethyl-piperazin-2-yl]-[4-(2,5-dimethyl-phenyl)-piperazin-1-yl]-methanone as a colorless oil, MS: 581.3 ([M+H, 1Cl]$^+$).

Example 22

[4-(4-Chloro-benzenesulfonyl)-1-pentyl-piperazin-2-yl]-[4-(2,5-dimethyl-phenyl)-piperazin-1-yl]-methanone Steps 1-3: In analogy to example 17, steps 1-3, from N-1-Boc-2-piperazinecarboxylic acid methyl ester (CAS Reg. No: [129799-15-1]), 4-chlorobenzenesulfonyl chloride and 1-(2,5-dimethylphenyl)-piperazine was prepared 4-(4-chloro-benzenesulfonyl)-2-[4-(2,5-dimethyl-phenyl)-piperazine-1-carbonyl]-piperazine-1-carboxylic acid tert-butyl ester as a light yellow foam, MS: 577.4 ([M+H, 1Cl]$^+$).

Step 4: To a solution of 4-(4-chloro-benzenesulfonyl)-2-[4-(2,5-dimethyl-phenyl)-piperazine-1-carbonyl]-piperazine-1-carboxylic acid tert-butyl ester (1.64 g) in ethanol (16.4 mL) was added a saturated solution of HCl in ethanol (16.4 mL) at 0° C. The reaction mixture was stirred at ambient temperature for 2 h and concentrated to give [4-(4-chloro-benzenesulfonyl)-piperazin-2-yl]-[4-(2,5-dimethyl-phenyl)-piperazin-1-yl]-methanone hydrochloride, MS: 477.0 ([M+H, 1Cl]$^+$).

Step 5: To a solution of [4-(4-chloro-benzenesulfonyl)-piperazin-2-yl]-[4-(2,5-dimethyl-phenyl)-piperazin-1-yl]-methanone hydrochloride (100 mg) in acetone (4 mL) was added cesium carbonate (254 mg), followed by 1-bromopentane (27 µL). The reaction mixture was stirred at ambient temperature for 1 h. Additional cesium carbonate (127 mg) and 1-bromopentane (14 µL) were added and stirring was continued at reflux over night. Water was added and the reaction mixture was extracted with ethyl acetate (×2). The combined organic layers were washed with brine, dried ($Na_2SO_4$), filtered and evaporated. Purification by chromatography ($SiO_2$, n-heptane/ethyl acetate 3:1) yielded [4-(4-chloro-benzenesulfonyl)-1-pentyl-piperazin-2-yl]-[4-(2,5-dimethyl-phenyl)-piperazin-1-yl]-methanone as a white foam, MS: 547.3 ([M+H, 1Cl]$^+$).

Example 23

[1-Butyl-4-(4-chloro-benzenesulfonyl)-piperazin-2-yl]-[4-(2,5-dimethyl-phenyl)-piperazin-1-yl]-methanone In analogy to example 20, step 5, from [4-(4-chloro-benzenesulfonyl)-piperazin-2-yl]-[4-(2,5-dimethyl-phenyl)-piperazin-1-yl]-methanone hydrochloride and 1-bromobutane was prepared [1-butyl-4-(4-chloro-benzenesulfonyl)-piperazin-2-yl]-[4-(2,5-dimethyl-phenyl)-piperazin-1-yl]-methanone as a white foam, MS: 533.3 ([M+H, 1Cl]$^+$).

Example 24

[4-(4-Chloro-benzenesulfonyl)-1-phenyl-piperazin-2-yl]-[4-(2,5-dimethyl-phenyl)-piperazin-1-yl]-methanone Under argon an oven-dried flask was charged with tris(dibenzylideneacetone)dipalladium (9.6 mg), sodium tert butylate (40 mg) and 2(di-tert-butylphosphino)biphenyl (6.3 mg). Then [4-(4-chloro-benzenesulfonyl)-piperazin-2-yl]-[4-(2,5-dimethyl-phenyl)-piperazin-1-yl]-methanone (100 mg), previously prepared from [4-(4-chloro-benzenesulfonyl)-piperazin-2-yl]-[4-(2,5-dimethyl-phenyl)-piperazin-1-yl]-methanone hydrochloride by extraction under basic conditions, in toluene (5 mL) was added, followed by a solution of bromobenzene (55 µL) in toluene (3 mL). The reaction mixture was stirred at 80° C. overnight. The mixture was cooled to room temperature, an aqueous solution of $NaHCO_3$ was added, the phases were separated, and the inorganic one was extracted with ethyl acetate (×3). The combined organic layers were dried ($Na_2SO_4$), filtered and evaporated. Purification by chromatography ($SiO_2$, n-heptane/ethyl acetate 3:1; ISOLUTE Flash $NH_2$, n-heptane/ethyl acetate) and trituration with n-heptane gave [4-(4-chloro-benzenesulfonyl)-1-phenyl-piperazin-2-yl]-[4-(2,5-dimethyl-phenyl)-piperazin-1-yl]-methanone as a white solid, MS: 553.3 ([M+H, 1Cl]$^+$).

Example 25

[4-(2-Chloro-benzenesulfonyl)-1-(4-fluoro-2-methyl-phenyl)-piperazin-2-yl]-[4-(2,5-dichloro-phenyl)-piperazin-1-yl]-methanone Step 1: In analogy to example 2, step 5, from 4-benzyl-1-(4-fluoro-2-methyl-phenyl)-piperazine-2-carboxylic acid ethyl ester and 2-chlorobenzenesulfonyl chloride was prepared 4-(2-chloro-benzenesulfonyl)-1-(4-fluoro-2-methyl-phenyl)-piperazine-2-carboxylic acid ethyl ester as a yellow oil, MS: 441.1 ([M+H, 1Cl]$^+$).

Step 2: In analogy to example 2, step 6, from 4-(2-chloro-benzenesulfonyl)-1-(4-fluoro-2-methyl-phenyl)-piperazine-2-carboxylic acid ethyl ester was prepared 4-(2-chloro-benzenesulfonyl)-1-(4-fluoro-2-methyl-phenyl)-piperazine-2-carboxylic acid as a white solid, MS: 410.9 ([M–H, 1Cl]$^-$).

Step 3: In analogy to example 1, step 1, from 4-(2-chloro-benzenesulfonyl)-1-(4-fluoro-2-methyl-phenyl)-piperazine-2-carboxylic acid and 1-(2,5-dichlorophenyl)-piperazine dihydrochloride was prepared [4-(2-chloro-benzenesulfonyl)-1-(4-fluoro-2-methyl-phenyl)-piperazin-2-yl]-[4-(2,5-dichloro-phenyl)-piperazin-1-yl]-methanone as a white solid, MS: 626.8 ([M+H, 1Cl]$^+$).

Example 26

[4-(2-Chloro-benzenesulfonyl)-1-(4-fluoro-2-methyl-phenyl)-piperazin-2-yl]-[4-(5-chloro-2-methyl-phenyl)-piperazin-1-yl]-methanone In analogy to example 1, step 1, from 4-(2-chloro-benzenesulfonyl)-1-(4-fluoro-2-methyl-phenyl)-piperazine-2-carboxylic acid (example 25, step 2) and 1-(5-chloro-ortho-tolyl)-piperazine, was prepared [4-(2-chloro-benzenesulfonyl)-1-(4-fluoro-2-methyl-phenyl)-piperazin-2-yl]-[4-(5-chloro-2-methyl-phenyl)-piperazin-1-yl]-methanone as a white solid, MS: 604.8 ([M+H, 1Cl]$^+$).

Example 27

[4-(2-Chloro-benzenesulfonyl)-1-(4-fluoro-2-methyl-phenyl)-piperazin-2-yl]-[4-(2,5-dimethyl-phenyl)-piperazin-1-yl]-methanone In analogy to example 1, step 1, from 4-(2-chloro-benzenesulfonyl)-1-(4-fluoro-2-methyl-phenyl)-piperazine-2-carboxylic acid (example 25, step 2) and 1-(2,5-dimethylphenyl)-piperazine was prepared [4-(2-chloro-benzenesulfonyl)-1-(4-fluoro-2-methyl-phenyl)-piperazin-2-yl]-[4-(2,5-dimethyl-phenyl)-piperazin-1-yl]-methanone as a white solid, MS: 584.8 ([M+H, 1Cl]$^+$).

Example 28

[4-(2,5-Dichloro-phenyl)-piperazin-1-yl]-[1-(4-fluoro-2-methyl-phenyl)-4-(naphthalene-1-sulfonyl)-piperazin-2-yl]-methanone Step 1: In analogy to example 2, step 5, from 4-benzyl-1-(4-fluoro-2-methyl-phenyl)-piperazine-2-carboxylic acid ethyl ester and 1-naphthalenesulfonyl chloride was prepared 1-(4-fluoro-2-methyl-phenyl)-4-(naphthalene-1-sulfonyl)-piperazine-2-carboxylic acid ethyl ester as a white solid, MS: 457.3 ([M+H]$^+$).

Step 2: In analogy to example 2, step 6, from 1-(4-fluoro-2-methyl-phenyl)-4-(naphthalene-1-sulfonyl)-piperazine-2-carboxylic acid ethyl ester was prepared 1-(4-fluoro-2-methyl-phenyl)-4-(naphthalene-1-sulfonyl)-piperazine-2-carboxylic acid as a white solid, MS: 427.0 ([M–H]$^-$).

Step 3: In analogy to example 1, step 1, from 1-(4-fluoro-2-methyl-phenyl)-4-(naphthalene-1-sulfonyl)-piperazine-2-carboxylic acid and 1-(2,5-dichlorophenyl)-piperazine dihydrochloride was prepared [4-(2,5-dichloro-phenyl)-piperazin-1-yl]-[1-(4-fluoro-2-methyl-phenyl)-4-

Example 29

[4-(5-Chloro-2-methyl-phenyl)-piperazin-1-yl]-[1-(4-fluoro-2-methyl-phenyl)-4-(naphthalene-1-sulfonyl)-piperazin-2-yl]-methanone In analogy to example 1, step 1, from 1-(4-fluoro-2-methyl-phenyl)-4-(naphthalene-1-sulfonyl)-piperazine-2-carboxylic acid and 1-(5-chloro-ortho-tolyl)-piperazine was prepared [4-(5-chloro-2-methyl-phenyl)-piperazin-1-yl]-[1-(4-fluoro-2-methyl-phenyl)-4-(naphthalene-1-sulfonyl)-piperazin-2-yl]-methanone as a white solid, MS: 621.0 ([M+H, 1Cl]$^+$).

Example 30

[4-(2,5-Dimethyl-phenyl)-piperazin-1-yl]-[1-(4-fluoro-2-methyl-phenyl)-4-(naphthalene-1-sulfonyl)-piperazin-2-yl]-methanone In analogy to example 1, step 1, from 1-(4-fluoro-2-methyl-phenyl)-4-(naphthalene-1-sulfonyl)-piperazine-2-carboxylic acid and 1-(2,5-dimethylphenyl)-piperazine was prepared [4-(2,5-dimethyl-phenyl)-piperazin-1-yl]-[1-(4-fluoro-2-methyl-phenyl)-4-(naphthalene-1-sulfonyl)-piperazin-2-yl]-methanone as a white solid, MS: 601.0 ([M+H]$^+$).

Example 31

[1-(4-Fluoro-2-methyl-phenyl)-4-(naphthalene-1-sulfonyl)-piperazin-2-yl]-[4-(3-trifluoromethyl-pyridin-2-yl)-piperazin-1-yl]-methanone In analogy to example 1, step 1, from 1-(4-fluoro-2-methyl-phenyl)-4-(naphthalene-1-sulfonyl)-piperazine-2-carboxylic acid and 1-(3-trifluoromethyl-pyridin-2-yl)-piperazine (CAS Reg. No.: [87394-63-6]) was prepared [1-(4-fluoro-2-methyl-phenyl)-4-(naphthalene-1-sulfonyl)-piperazin-2-yl]-[4-(3-trifluoromethyl-pyridin-2-yl)-piperazin-1-yl]-methanone as a white solid, MS: 642.3 ([M+H]$^+$).

Example 32

[4-(2,5-Dichloro-phenyl)-piperazin-1-yl]-[1-(4-fluoro-2-methyl-phenyl)-4-(quinoline-8-sulfonyl)-piperazin-2-yl]-methanone Step 1: In analogy to example 2, step 5, from 4-benzyl-1-(4-fluoro-2-methyl-phenyl)-piperazine-2-carboxylic acid ethyl ester and 8-quinolinesulfonyl chloride was prepared 1-(4-fluoro-2-methyl-phenyl)-4-(quinoline-8-sulfonyl)-piperazine-2-carboxylic acid ethyl ester as a white solid, MS: 458.3 ([M+H]$^+$).

Step 2: In analogy to example 2, step 6, from 1-(4-fluoro-2-methyl-phenyl)-4-(quinoline-8-sulfonyl)-piperazine-2-carboxylic acid ethyl ester was prepared 1-(4-fluoro-2-methyl-phenyl)-4-(quinoline-8-sulfonyl)-piperazine-2-carboxylic acid as a white solid, MS: 428.4 ([M–H]$^-$).

Step 3: In analogy to example 1, step 1, from 1-(4-fluoro-2-methyl-phenyl)-4-(quinoline-8-sulfonyl)-piperazine-2-carboxylic acid and 1-(2,5-dichlorophenyl)-piperazine dihydro-chloride was prepared [4-(2,5-dichloro-phenyl)-piperazin-1-yl]-[1-(4-fluoro-2-methyl-phenyl)-4-(quinoline-8-sulfonyl)-piperazin-2-yl]-methanone as a white solid, MS: 642.0 ([M+H, 1Cl]$^+$).

Example 33

[4-(5-Chloro-2-methyl-phenyl)-piperazin-1-yl]-[1-(4-fluoro-2-methyl-phenyl)-4-(quinoline-8-sulfonyl)-piperazin-2-yl]-methanone In analogy to example 1, step 1, from 1-(4-fluoro-2-methyl-phenyl)-4-(quinoline-8-sulfonyl)-piperazine-2-carboxylic acid and 1-(5-chloro-ortho-tolyl)-piperazine was prepared [4-(5-chloro-2-methyl-phenyl)-piperazin-1-yl]-[1-(4-fluoro-2-methyl-phenyl)-4-(quinoline-8-sulfonyl)-piperazin-2-yl]-methanone as a white solid, MS: 621.8 ([M+H, 1Cl]$^+$).

Example 34

[4-(2,5-Dimethyl-phenyl)-piperazin-1-yl]-[1-(4-fluoro-2-methyl-phenyl)-4-(quinoline-8-sulfonyl)-piperazin-2-yl]-methanone In analogy to example 1, step 1, from 1-(4-fluoro-2-methyl-phenyl)-4-(quinoline-8-sulfonyl)-piperazine-2-carboxylic acid and 1-(2,5-dimethylphenyl)-piperazine was prepared [4-(2,5-dimethyl-phenyl)-piperazin-1-yl]-[1-(4-fluoro-2-methyl-phenyl)-4-(quinoline-8-sulfonyl)-piperazin-2-yl]-methanone as a white solid, MS: 602.0 ([M+H]$^+$).

Example 35

[4-(2,5-Dichloro-phenyl)-piperazin-1-yl]-[4-(propane-2-sulfonyl)-1-o-tolyl-piperazin-2-yl]-methanone Step 1: In analogy to example 2, step 6, from 4-benzyl-1-o-tolyl-piperazine-2-carboxylic acid ethyl ester (example 10, steps 1-4) was prepared 4-benzyl-1-o-tolyl-piperazine-2-carboxylic acid as a white solid, MS: 309.3 ([M–H]$^-$).

Step 2: In analogy to example 1, step 1, from 4-benzyl-1-o-tolyl-piperazine-2-carboxylic acid and 1-(2,5-dichlorophenyl)piperazine dihydrochloride was prepared (4-benzyl-1-o-tolyl-piperazin-2-yl)-[4-(2,5-dichloro-phenyl)-piperazin-1-yl]-methanone as a white solid, MS: 522.8 ([M+H, 1Cl]$^+$).

Step 3: In analogy to example 2, step 5 from (4-benzyl-1-o-tolyl-piperazin-2-yl)-[4-(2,5-dichloro-phenyl)-piperazin-1-yl]-methanone and iso-propylsulfonyl chloride was prepared [4-(2,5-dichloro-phenyl)-piperazin-1-yl]-[4-(propane-2-sulfonyl)-1-o-tolyl-piperazin-2-yl]-methanone as a white foam, MS: 539.3 ([M+H, 1Cl]$^+$).

Example 36

[4-(Biphenyl-4-sulfonyl)-1-o-tolyl-piperazin-2-yl]-[4-(2,5-dichloro-phenyl)-piperazin-1-yl]-methanone In analogy to example 35, step 3, from (4-benzyl-1-o-tolyl-piperazin-2-yl)-[4-(2,5-dichloro-phenyl)-piperazin-1-yl]-methanone and 4-biphenylsulfonyl chloride was prepared [4-(biphenyl-4-sulfonyl)-1-o-tolyl-piperazin-2-yl]-[4-(2,5-dichloro-phenyl)-piperazin-1-yl]-methanone as a white foam, MS: 649.3 ([M+H, 1Cl]$^+$).

Example 37

3-{3-[4-(2,5-Dichloro-phenyl)-piperazine-1-carbonyl]-4-o-tolyl-piperazine-1-sulfonyl}-thiophene-2-carboxylic acid methyl ester In analogy to example 35, step 3, from 4-benzyl-1-o-tolyl-piperazin-2-yl)-[4-(2,5-dichloro-phenyl)-piperazin-1-yl]-methanone and 2-(methoxycarbonyl)thiophene-3-sulfonyl chloride was prepared 3-{3-[4-(2,5-dichloro-phenyl)-piperazine-1-carbonyl]-4-o-tolyl-piperazine-1-sulfonyl}-thiophene-2-carboxylic acid methyl ester as a white foam, MS: 637.0 ([M+H]$^+$).

Example 38

[4-(3-Chloro-benzenesulfonyl)-1-(4-fluoro-2-methyl-phenyl)-piperazin-2-yl]-(3',6'-dimethyl-2,3,5,6-tetrahydro-[1,2']bipyrazinyl-4-yl)-methanone Step 1: In analogy to example 1, step 1, from 4-(3-chloro-benzenesulfonyl)-1-(4-fluoro-2-methyl-phenyl)-piperazine-2-carboxylic acid (example 2, step 5) and N-Boc piperazine was prepared 4-[4-(3-chloro-benzenesulfonyl)-1-(4-fluoro-2-methyl-phenyl)-piperazine-2-carbonyl]-piperazine-1-carboxylic acid tert-butyl ester as a white solid, MS: 580.8 ([M+H, 1Cl]$^+$).

Step 2: In analogy to example 17, step 4, from 4-[4-(3-chloro-benzenesulfonyl)-1-(4-fluoro-2-methyl-phenyl)-piperazine-2-carbonyl]-piperazine-1-carboxylic acid tert-butyl ester was prepared [4-(3-chloro-benzenesulfonyl)-1-(4-fluoro-2-methyl-phenyl)-piperazin-2-yl]-piperazin-1-yl-methanone as a white solid, MS: 481.0 ([M+H, 1Cl]$^+$).

Step 3: [4-(3-Chloro-benzenesulfonyl)-1-(4-fluoro-2-methyl-phenyl)-piperazin-2-yl]-piperazin-1-yl-methanone (60 mg), 3-chloro-2,5-dimethylpyrazine (18.1 μL) and triethylamine (20.8 μL) in acetonitrile (1 mL) were heated to 170° C. in the microwave. Water was added and the reaction mixture was extracted with ethyl acetate. The combined organic phases were washed with brine, dried (Na$_2$SO$_4$), filtered and evaporated. Purification by chromatography (SiO$_2$, n-heptane/ethyl acetate 1:2) gave [4-(3-chloro-benzenesulfonyl)-1-(4-fluoro-2-methyl-phenyl)-piperazin-2-yl]-(3',6'-dimethyl-2,3,5,6-tetrahydro-[1,2']bipyrazinyl-4-yl)-methanone as a yellow oil, MS: 587.3 ([M+H, 1Cl]$^+$).

Example 39

[1-Benzyl-4-(3-chloro-benzenesulfonyl)-piperazin-2-yl]-(3',6'-dimethyl-2,3,5,6-tetrahydro-[1,2']bipyrazinyl-4-yl)-methanone Step 1: In analogy to example 13, step 2, from 1-benzyl-piperazine-2-carboxylic acid ethyl ester and 3-chlorobenzenesulfonyl chloride was prepared 1-benzyl-4-(3-chloro-benzenesulfonyl)-piperazine-2-carboxylic acid ethyl ester as a yellow oil, MS: 423.1 ([M+H, 1Cl]$^+$).

Step 2: In analogy to example 2, Step 6, from 1-benzyl-4-(3-chloro-benzenesulfonyl)-piperazine-2-carboxylic acid ethyl ester was prepared 1-benzyl-4-(3-chloro-benzenesulfonyl)-piperazine-2-carboxylic acid as an off-white solid, MS: 593.0 ([M–H, 1Cl]$^-$).

Step 3: In analogy to example 1, step 1, from 1-benzyl-4-(3-chloro-benzenesulfonyl)-piperazine-2-carboxylic acid and 1-Boc-piperazine was prepared 4-[1-benzyl-4-(3-chloro-benzenesulfonyl)-piperazine-2-carbonyl]-piperazine-1-carboxylic acid tert-butyl ester as a white foam, MS: 562.8 ([M+H, 1Cl]$^+$).

Step 4: In analogy to example 38, step 2, from 4-[1-benzyl-4-(3-chloro-benzenesulfonyl)-piperazine-2-carbonyl]-piperazine-1-carboxylic acid tert-butyl ester was prepared [1-benzyl-4-(3-chloro-benzenesulfonyl)-piperazin-2-yl]-piperazin-1-yl-methanone as a white foam, MS: 463 ([M+H, 1Cl]$^+$).

Step 5: In analogy to example 38, step 3, from [1-benzyl-4-(3-chloro-benzenesulfonyl)-piperazin-2-yl]-piperazin-1-yl-methanone and 3-chloro-2,5-dimethylpyrazine was prepared [1-benzyl-4-(3-chloro-benzenesulfonyl)-piperazin-2-yl]-(3',6'-dimethyl-2,3,5,6-tetrahydro-[1,2']bipyrazinyl-4-yl)-methanone as a yellow oil, MS: 569.3 ([M+H, 1Cl]$^+$).

Example 40

[4-(3-Chloro-phenyl)-piperidin-1-yl]-[1-(4-fluoro-2-methyl-phenyl)-4-(propane-2-sulfonyl)-piperazin-2-yl]-methanone Step 1: In analogy to example 2, step 5, from 4-benzyl-1-(4-fluoro-2-methyl-phenyl)-piperazine-2-carboxylic acid ethyl ester and iso-propylsulfonyl chloride was prepared 1-(4-fluoro-2-methyl-phenyl)-4-(propane-2-sulfonyl)-piperazine-2-carboxylic acid ester as a colorless oil, MS: 373.1 ([M+H, 1Cl]$^+$).

Step 2: In analogy to example 2, step 6, from 1-(4-fluoro-2-methyl-phenyl)-4-(propane-2-sulfonyl)-piperazine-2-carboxylic acid ester was prepared 1-(4-fluoro-2-methyl-phenyl)-4-(propane-2-sulfonyl)-piperazine-2-carboxylic acid as a yellow solid, MS: 343.1 ([M–H, 1Cl]$^-$).

Step 3: In analogy to example 1, step 1, from 1-(4-fluoro-2-methyl-phenyl)-4-(propane-2-sulfonyl)-piperazine-2-carboxylic acid and 4-(3-chlorophenyl)-piperidine was prepared [4-(3-chloro-phenyl)-piperidin-1-yl]-[1-(4-fluoro-2-methyl-phenyl)-4-(propane-2-sulfonyl)-piperazin-2-yl]-methanone as a white solid, MS: 522.2 ([M+H, 1Cl]$^+$).

Example 41

[4-(3-Chloro-benzenesulfonyl)-1-o-tolyl-piperazin-2-yl]-(3',6'-dimethyl-2,3,5,6-tetrahydro-[1,2']bipyrazinyl-4-yl)-methanone In analogy to example 1, step 1, from 4-(3-chloro-benzenesulfonyl)-1-o-tolyl-piperazine-2-carboxylic acid and 3',6'-dimethyl-3,4,5,6-tetrahydro-2H-[1,2']bipyrazinyl (CAS Reg. No.: [59215-42-8]) was prepared [4-(3-chloro-benzenesulfonyl)-1-o-tolyl-piperazin-2-yl]-(3',6'-dimethyl-2,3,5,6-tetrahydro-[1,2']bipyrazinyl-4-yl)-methanone as a white solid, MS: 569.3 ([M+H, 1Cl]$^+$).

Example 42

Cis-[4-(2,5-Dimethyl-phenyl)-piperazin-1-yl]-[-1-(3-methoxy-benzenesulfonyl)-4-phenyl-piperidin-3-yl]-methanone Step 1: Cis-4-phenylnipecotic acid hydrochloride (CAS Reg. No. [858430-42-9]) (195 mg) (three times suspended in toluene and evaporated under reduced pressure to remove water) was suspended in hexamethyldisilazane (4 mL) and refluxed for 3 h. The solution was evaporated under reduced pressure and dissolved in THF (4 mL). 3-Methoxybenzene sulfonyl chloride (0.13 mL) was added and the solution was stirred for 16 h at ambient temperature. H$_2$O was added and after 1 h the solvents were evaporated. The residue was partitioned between water/ethyl acetate (3×), the organic phases were washed with brine, dried (Na$_2$SO$_4$), filtered and evaporated. Purification by chromatography (SiO$_2$, n-heptane/ethyl acetate 1:1) gave cis-1-(3-methoxy-benzenesulfonyl)-4-phenyl-piperidine-3-carboxylic acid as a white solid, MS: 374.3 (M−H])−. Step 2: In analogy to example 1, step 1, from cis-1-(3-methoxy-benzenesulfonyl)-4-phenyl-piperidine-3-carboxylic acid and 1-(2,5-dimethylphenyl)piperazine was prepared cis-[4-(2,5-dimethyl-phenyl)-piperazin-1-yl]-[-1-(3-methoxy-benzenesulfonyl)-4-phenyl-piperidin-3-yl]-methanone as a white solid (mp 192° C.), MS: 548.4 ([M+H])+.

Example 43

[4-(2,5-Dimethyl-phenyl)-piperazin-1-yl]-[(3S,4S)-1-(3-methoxy-benzenesulfonyl)-4-phenyl-piperidin-3-yl]-methanone Cis-[4-(2,5-dimethyl-phenyl)-piperazin-1-yl]-[-1-(3-methoxy-benzenesulfonyl)-4-phenyl-piperidin-3-yl]-methanone was separated into the enantiomers by chiral HPLC on Chiralpak AD using n-heptane/25% isopropanol as the mobile phase to give [4-(2,5-dimethyl-phenyl)-piperazin-1-yl]-[(3S,4S)-1-(3-methoxy-benzenesulfonyl)-4-phenyl-piperidin-3-yl]-methanone as a white foam, MS: 548.3 ([M+H])+ and [4-(2,5-dimethyl-phenyl)-piperazin-1-yl]-[(3R,4R)-1-(3-methoxy-benzenesulfonyl)-4-phenyl-piperidin-3-yl]-methanone as white foam, MS: 548.3 ([M+H])+.

Example 44

[Trans-1-(3-Chloro-benzenesulfonyl)-4-phenyl-piperidin-3-yl]-[4-(2,5-dimethyl-phenyl)-piperazin-1-yl]-methanone Step 1: In analogy to example 1, step 1, from trans-N-Boc-4-phenyl-nipecotic acid (CAS Reg. No.: [170838-49-0]) and 1-(2,5-dimethylphenyl)piperazine was prepared trans-3-[4-(2,5-dimethyl-phenyl)-piperazine-1-carbonyl]-4-phenyl-piperidine-1-carboxylic acid tert-butyl ester as a white foam, MS: 478.2 ([M+H])+.
Step 2: In analogy to example 22, step 4, from trans-3-[4-(2,5-dimethyl-phenyl)-piperazine-1-carbonyl]-4-phenyl-piperidine-1-carboxylic acid tert-butyl ester was prepared trans-[4-(2,5-dimethyl-phenyl)-piperazin-1-yl]-(-4-phenyl-piperidin-3-yl)-methanone hydrochloride as a white foam, MS: 378.4 ([M+H])+.
Step 3: In analogy to example 1, step 3, from trans-[4-(2,5-dimethyl-phenyl)-piperazin-1-yl]-(-4-phenyl-piperidin-3-yl)-methanone hydrochloride and 3-chlorobenzenesulfonyl chloride was prepared [trans-1-(3-chloro-benzenesulfonyl)-4-phenyl-piperidin-3-yl]-[4-(2,5-dimethyl-phenyl)-piperazin-1-yl]-methanone as a white foam, MS: 552.1 ([M+H, 1Cl])+.

Example 45

[Trans-1-(3,5-Dimethyl-isoxazole-4-sulfonyl)-4-phenyl-piperidin-3-yl]-[4-(2,5-dimethyl-phenyl)-piperazin-1-yl]-methanone In analogy to example 1, step 3, from trans-[4-(2,5-dimethyl-phenyl)-piperazin-1-yl]-(-4-phenyl-piperidin-3-yl)-methanone hydrochloride and 3,5-dimethylisoxazole-4-sulfonyl chloride (CAS Reg. No.: [80466-79-1]) was prepared [trans-1-(3,5-dimethyl-isoxazole-4-sulfonyl)-4-phenyl-piperidin-3-yl]-[4-(2,5-dimethyl-phenyl)-piperazin-1-yl]-methanone as a white foam, MS: 537.4 ([M+H])+.

Example 46

[4-(2,5-Dimethyl-phenyl)-piperazin-1-yl]-[(3S,4S)-1-(3-methoxy-benzenesulfonyl)-4-o-tolyl-piperidin-3-yl]-methanone Step 1: To a solution of 2-methylphenylzinc chloride ([84109-17-1], previously prepared from o-tolylmagnesium chloride (44.07 mL) and zinc chloride (8.81 g) in THF (200 mL)) a mixture of 4-trifluoromethanesulfonyloxy-5,6-dihydro-2H-pyridine-1,3-dicarboxylic acid 1-tert-butyl ester 3-methyl ester (CAS Reg. No. [161491-25-4]) (11.4 g) in THF (90 mL) followed by tetrakis(triphenylphosphine)palladium(0) (1.02 g) was added. The reaction mixture was stirred at room temperature over night and then was quenched with ice. The mixture was diluted with tert-butyl methyl ether and washed with 2 M aqueous sodium carbonate solution. The aqueous phases were extracted with tert-butyl methyl ether. The combined organic layers were washed with brine, dried (Na$_2$SO$_4$), filtered and evaporated. Purification by chromatography (SiO$_2$, n-heptane/ethyl acetate 5:1) gave 4-o-tolyl-5,6-dihydro-2H-pyridine-1,3-dicarboxylic acid 1-tert-butyl ester 3-methyl ester as light yellow oil, MS: 332.0 ([M+H])+.
Step 2: In analogy to example 2, step 6, from 4-o-tolyl-5,6-dihydro-2H-pyridine-1,3-dicarboxylic acid 1-tert-butyl ester 3-methyl ester was prepared 4-o-tolyl-5,6-dihydro-2H-pyridine-1,3-dicarboxylic acid 1-tert-butyl ester as a white solid, MS: 316.2 ([M−H])−.
Step 3: In a glove box an autoclave was charged with 4-o-tolyl-5,6-dihydro-2H-pyridine-1,3-dicarboxylic acid 1-tert-butyl ester (2.5 g), [Ru(OAc)$_2$ ((R)-(2-furyl)-MeOBIPHEP)] (24 mg), triethylamine (1.1 mL) and methanol (25 mL). The asymmetric hydrogenation was run for 60 h at 80° C. under 40 bar of hydrogen. After cooling to room temperature the pressure was released from the autoclave, the methanol solution was diluted with tert-butyl methyl ether (320 mL) and extracted with 1 M aqueous sodium hydroxide solution (2×, 320 mL). The aqueous layer was poured on ice, acidified with ice-cold 2 M aqueous hydrochloric acid solution to pH 1 and extracted with ethyl acetate (3×). The combined organic layers were dried (Na$_2$SO$_4$), filtered and concentrated in vacuo and triturated from n-heptane to give (3S,4S)-4-o-tolyl-piperidine-1,3-dicarboxylic acid 1-tert-butyl ester as a white solid, MS: 318.2.
Step 4: In analogy to example 1, step 1, from (3S,4S)-4-o-tolyl-piperidine-1,3-dicarboxylic acid 1-tert-butyl ester and 1-(2,5-dimethylphenyl)piperazine was prepared (3S,4S)-3-[4-(2,5-dimethyl-phenyl)-piperazine-1-carbonyl]-4-o-tolyl-piperidine-1-carboxylic acid tert-butyl ester as a white foam, MS: 492.3 ([M+H])+.
Step 5: In analogy to example 22, step 4, from (3S,4S)-3-[4-(2,5-dimethyl-phenyl)-piperazine-1-carbonyl]-4-o-tolyl-piperidine-1-carboxylic acid tert-butyl ester was prepared [4-(2,5-dimethyl-phenyl)-piperazin-1-yl]-((3S,4S)-4-o-tolyl-piperidin-3-yl)-methanone hydrochloride as colorless oil, MS: 392.4 ([M+H])+.
Step 6: In analogy to example 1, step 3, from [4-(2,5-dimethyl-phenyl)-piperazin-1-yl]-((3S,4S)-4-o-tolyl-piperidin-3-yl)-methanone hydrochloride and 3-methoxybenzenesulfonyl chloride was prepared [4-(2,5-dimethyl-phenyl)- piperazin-1-yl]-[(3S,4S)-1-(3-methoxy-benzenesulfonyl)-4-o-tolyl-piperidin-3-yl]-methanone as a white foam, MS: 562.5 ([M+H])+.

Example 47

[(3S,4S)-1-(3-Chloro-benzenesulfonyl)-4-o-tolyl-piperidin-3-yl]-[4-(2,5-dimethyl-phenyl-piperazin-1-yl]-methanone In analogy to example 1, step 3, from [4-(2,5-dimethyl-phenyl)-piperazin-1-yl]-((3S,4S)-4-o-tolyl-piperidin-3-yl)-methanone hydrochloride and 3-chlorobenzenesulfonyl chloride was prepared [(3S,4S)-1-(3-chloro-benzenesulfonyl)-4-o-tolyl-piperidin-3-yl]-[4-(2,5-dimethyl-phenyl)-piperazin-1-yl]-methanone as a white foam, MS: 566.4 ([M+H, 1Cl])+.

Example 48

[4-(2,5-Dimethyl-phenyl)-piperazin-1-yl]-((3S,4S)-1-methanesulfonyl-4-o-tolyl-piperidin-3-yl)-methanone In analogy to example 1, step 3, from [4-(2,5-dimethyl-phenyl)-piperazin-1-yl]-((3S,4S)-4-o-tolyl-piperidin-3-yl)-methanone hydrochloride and methanesulfonyl chloride was prepared [4-(2,5-dimethyl-phenyl)-piperazin-1-yl]-((3S,4S)-1-methanesulfonyl-4-o-tolyl-piperidin-3-yl)-methanone as a white foam, MS: 470.1 ([M+H])+.

Example 49

[(3S,4S)-1-(3-Chloro-benzenesulfonyl)-4-phenyl-piperidin-3-yl]-[4-(2,5-dimethyl-phenyl)-piperazin-1-yl]-methanone Step 1: In analogy to example 1, step 1, from (3S,4S)-4-phenyl-piperidine-1,3-dicarboxylic acid 1-tert-butyl ester (CAS Reg. No.: [197900-77-9]) and 1-(2,5-dimethylphenyl) piperazine was prepared (3S,4S)-3-[4-(2,5-dimethyl-phenyl)-piperazine-1-carbonyl]-4-phenyl-piperidine-1-carboxylic acid tert-butyl ester as a white foam, MS: 478.28 ([M+H])+.
Step 2: In analogy to example 22, step 4, from (3S,4S)-3-[4-(2,5-dimethyl-phenyl)-piperazine-1-carbonyl]-4-phenyl-piperidine-1-carboxylic acid tert-butyl ester was prepared [4-(2,5-dimethyl-phenyl)-piperazin-1-yl]-((3S,4S)-4-phenyl-piperidin-3-yl)-methanone hydrochloride as crude product, MS: 392.4 ([M+H])+.
Step 3: In analogy to example 1, step 3, from [4-(2,5-dimethyl-phenyl)-piperazin-1-yl]-((3S,4S)-4-phenyl-piperidin-3-yl)-methanone hydrochloride and 3-chlorobenzenesulfonyl chloride was prepared [(3S,4S)-1-(3-chloro-benzenesulfonyl)-4-phenyl-piperidin-3-yl]-[4-(2,5-dimethyl-phenyl)-piperazin-1-yl]-methanone as a white foam, MS: 552.2 ([M+H, 1Cl])+.

Example 50

[4-(2,5-Dimethyl-phenyl)-piperazin-1-yl]-((3S,4S)-1-methanesulfonyl-4-phenyl-piperidin-3-yl)-methanone In analogy to example 1, step 3, [4-(2,5-dimethyl-phenyl)-piperazin-1-yl]-((3S,4S)-4-phenyl-piperidin-3-yl)-methanone hydrochloride and methanesulfonyl chloride was prepared [4-(2,5-dimethyl-phenyl)-piperazin-1-yl]-((3S,4S)-1-methanesulfonyl-4-phenyl-piperidin-3-yl)-methanone as a white foam, MS: 456.3 ([M+H])+.

Example 51

[(3R,4R)-1-(3-Chloro-benzenesulfonyl)-4-phenyl-piperidin-3-yl]-[4-(2,5-dimethyl-phenyl)-piperazin-1-yl]-methanone Step 1: In analogy to example 1, step 1, from (3R,4R)-4-phenyl-piperidine-1,3-dicarboxylic acid 1-tert-butyl ester (CAS Reg. No.: [197900-84-8]) and 1-(2,5-dimethylphenyl) piperazine was prepared (3R,4R)-3-[4-(2,5-dimethyl-phenyl)-piperazine-1-carbonyl]-4-phenyl-piperidine-1-carboxylic acid tert-butyl ester as a white foam, MS: 478.27 ([M+H])+.
Step 2: In analogy to example 22, step 4, from (3R,4R)-3-[4-(2,5-dimethyl-phenyl)-1,3-piperazine-1-carbonyl]-4-phenyl-piperidine-1-carboxylic acid tert-butyl ester was prepared [4-(2,5-dimethyl-phenyl)-piperazin-1-yl]-((3R,4R)-4-phenyl-piperidin-3-yl)-methanone hydrochloride, which was directly subjected to the following reaction, MS: 378.4 ([M+H, 1Cl])+.
Step 3: In analogy to example 1, step 3, from [4-(2,5-dimethyl-phenyl)-piperazin-1-yl]-((3R,4R)-4-phenyl-piperidin-3-yl)-methanone hydrochloride and 3-chlorobenzenesulfonyl chloride was prepared [(3R,4R)-1-(3-chloro-benzenesulfonyl)-4-phenyl-piperidin-3-yl]-[4-dimethyl-phenyl)-piperazin-1-yl]-methanone as a white foam, MS: 552.2 ([M+H, 1Cl])+.

Example 52

[4-(2,5-Dimethyl-phenyl)-piperazin-1-yl]-[(3S,4R)-1-(3-methoxy-benzenesulfonyl)-4-o-tolyl-piperidin-3-yl]-methanone Step 1: In analogy to example 46, step 3, from 4-o-tolyl-5,6-dihydro-2H-pyridine-1,3-dicarboxylic acid 1-tert-butyl ester using Ru(OAc)$_2$((S)-BITIANP as catalyst for the enantioselective hydrogenation was prepared (3R,4R)-4-o-tolyl-piperidine-1,3-dicarboxylic acid 1-tert-butyl ester as a white solid, MS: 318.4 ([M−H])−.
Step 2: To a solution of triphenylphosphine (2.66 g) in THF (30 ml) was added diethyl azodicarboxylate (1.58 mL) at 0° C. After 30 minutes, methanol (1.58 mL) and a solution of (3R,4R)-4-o-tolyl-piperidine-1,3-dicarboxylic acid 1-tert-butyl ester in THF (30 mL) were added subsequently at 0-5° C. The reaction mixture was stirred for 3 h at room temperature. The reaction was quenched with a saturated aqueous solution of NH$_4$Cl, tert-butyl methyl ether was added, and the phases were separated. The inorganic one was extracted with tert-butyl methyl ether (3×100 ml). The combined organic layers were dried (Na$_2$SO$_4$), filtered and evaporated. Purification by chromatography (SiO$_2$, CH$_2$Cl$_2$ to CH$_2$Cl$_2$/MeOH 95:5) yielded (3R,4R)-4-o-tolyl-piperidine-1,3-dicarboxylic acid 1-tert-butyl ester 3-methyl ester as a colorless gum, MS: 334.1 ([M+H])+.
Step 3: A mixture of (3R,4R)-4-o-tolyl-piperidine-1,3-dicarboxylic acid 1-tert-butyl ester 3-methyl ester (200 mg) and sodium methoxide (65 mg) in anhydrous toluene (6 mL) was heated at reflux over night. After cooling to room temperature the reaction mixture was quenched with water and concentrated in vacuo. The residue was dissolved in a mixture of 1,4-dioxane (3 mL) and 2 M aqueous sodium hydroxide solution (3 mL). After stirring at RT for 5 h the mixture was diluted with water and washed with two portions of tert-butyl methyl ether. The aqueous layer was cooled to 0° C., acidified to pH 1-2 with ice-cold 1 M aqueous $KHSO_4$ solution and extracted with ethyl acetate. The combined organic layers were dried ($Na_2SO_4$), filtered and evaporated to give (3S,4R)-4-o-tolyl-piperidine-1,3-dicarboxylic acid 1-tert-butyl ester as a white solid, MS: 318.4 ([M–H])⁻.

Step 4: In analogy to example 1, step 1, from (3S,4R)-4-o-tolyl-piperidine-1,3-dicarboxylic acid 1-tert-butyl ester and 1-(2,5-dimethylphenyl)piperazine was prepared (3S,4R)-3-[4-(2,5-dimethyl-phenyl)-piperazine-1-carbonyl]-4-o-tolyl-piperidine-1-carboxylic acid tert-butyl ester as a white solid, MS: 492.1 ([M+H])⁺.

Step 5: In analogy to example 22, step 4, from (3S,4R)-3-[4-(2,5-dimethyl-phenyl)-piperazine-1-carbonyl]-4-o-tolyl-piperidine-1-carboxylic acid tert-butyl ester was prepared [4-(2,5-dimethyl-phenyl)-piperazin-1-yl]-((3S,4R)-4-o-tolyl-piperidin-3-yl)-methanone hydrochloride as a white solid, MS: 392.3 ([M+H])⁺.

Step 6: In analogy to example 1, step 3, from [4-(2,5-dimethyl-phenyl)-piperazin-1-yl]-((3S,4R)-4-o-tolyl-piperidin-3-yl)-methanone hydrochloride and 3-methoxybenzenesulfonylchloride was prepared [4-(2,5-dimethyl-phenyl)-piperazin-1-yl]-[(3S,4R)-1-(3-methoxy-benzenesulfonyl)-4-o-tolyl-piperidin-3-yl]-methanone as a white solid, MS: 562.3 ([M+H]⁺.

Example 53

[(3S,4S)-1-(3-Chloro-benzenesulfonyl)-4-(4-fluoro-phenyl)-piperidin-3-yl]-[4-(5-chloro-2-methyl-phenyl)-piperazin-1-yl]-methanone Step 1: In analogy to example 46, steps 1-2, from 4-trifluoromethanesulfonyloxy-5,6-dihydro-2H-pyridine-1,3-dicarboxylic acid 1-tert-butyl ester 3-methyl ester (CAS Reg. No. [161491-25-4]) and 4-fluorophenylzinc bromide was prepared 4-(4-fluoro-phenyl)-5,6-dihydro-2H-pyridine-1,3-dicarboxylic acid 1-tert-butyl ester as a white foam, MS: 320.5 ([M–H])⁻.

Step 2: In analogy to example 46, step 3, from 4-(4-fluoro-phenyl)-5,6-dihydro-2H-pyridine-1,3-dicarboxylic acid 1-tert-butyl ester using [Ru(OAc)₂((R)-MeOBIPHEP)] as catalyst for the enantioselective hydrogenation was prepared (−)-(3S,4S)-4-(4-fluoro-phenyl)-piperidine-1,3-dicarboxylic acid 1-tert-butyl ester as an off-white solid, MS: 322.5 ([M+H])⁺.

Step 3: In analogy to example 1, step 1, from (−)-(3S,4S)-4-(4-fluoro-phenyl)-piperidine-1,3-dicarboxylic acid 1-tert-butyl ester and 1-(5-chloro-2-methylphenyl)-piperazine was prepared (3S,4S)-3-[4-(5-chloro-2-methyl-phenyl)-piperazine-1-carbonyl]-4-(4-fluoro-phenyl)-piperidine-1-carboxylic acid tert-butyl ester as a white foam, MS: 516.3 ([M+H, 1Cl])⁺.

Step 4: In analogy to example 22, step 4, from (3S,4S)-3-[4-(5-chloro-2-methyl-phenyl)-piperazine-1-carbonyl]-4-(4-fluoro-phenyl)-piperidine-1-carboxylic acid tert-butyl ester was prepared [4-(5-chloro-2-methyl-phenyl)-piperazin-1-yl]-[(3S,4S)-4-(4-fluoro-phenyl)-piperidin-3-yl]-methanone hydrochloride as a white foam, MS: 416.4 ([M+H, 1Cl])⁺.

Step 5: In analogy to example 1, step 3, from [4-(5-chloro-2-methyl-phenyl)-piperazin-1-yl]-[(3S,4S)-4-(4-fluoro-phenyl)-piperidin-3-yl]-methanone hydrochloride and 3-chlorobenzenesulfonyl chloride was prepared [(3S,4S)-1-(3-chloro-benzenesulfonyl)-4-(4-fluoro-phenyl)-piperidin-3-yl]-[4-(5-chloro-2-methyl-phenyl)-piperazin-1-yl]-methanone as a white foam, MS: 590.3 ([M+H, 1Cl])⁺.

Example 54

[4-(5-Chloro-2-methyl-phenyl)-piperazin-1-yl]-[(3S,4S)-4-(4-fluoro-phenyl)-1-(2-trifluoromethyl-benzenesulfonyl)-piperidin-3-yl]-methanone In analogy to example 1, step 3, from [4-(5-chloro-2-methyl-phenyl)-piperazin-1-yl]-[(3S,4S)-4-(4-fluoro-phenyl)-piperidin-3-yl]-methanone hydrochloride and 2-(trifluoromethyl)benzenesulfonyl chloride was prepared [4-(5-chloro-2-methyl-phenyl)-piperazin-1-yl]-[(3S,4S)-4-(4-fluoro-phenyl)-1-(2-trifluoromethyl-benzenesulfonyl)-piperidin-3-yl]-methanone as a white foam, MS: 624.2 ([M+H, 1Cl])⁺.

Example 55

[(3S,4R)-1-(3-Chloro-benzenesulfonyl)-4-(4-fluoro-phenyl)-piperidin-3-yl]-[4-(5-chloro-2-methyl-phenyl)-piperazin-1-yl]-methanone Step 1: In analogy to example 46, step 3, from 4-(4-fluoro-phenyl)-5,6-dihydro-2H-pyridine-1,3-dicarboxylic acid 1-tert-butyl ester using [Ru(OAc)₂((S)-(3,5-Xyl,4-MeO-MeOBIPHEP))] as catalyst for the enantioselective hydrogenation was prepared (3R,4R)-4-(4-fluoro-phenyl)-piperidine-1,3-dicarboxylic acid 1-tert-butyl ester as white foam, MS: 322.5 ([M–H])⁻.

Step 2: In analogy to example 52, steps 2-3, from (3R,4R)-4-(4-fluoro-phenyl)-piperidine-1,3-dicarboxylic acid 1-tert-butyl ester was prepared (3S,4R)-4-(4-fluoro-phenyl)-piperidine-1,3-dicarboxylic acid 1-tert-butyl ester as off-white foam, MS: 322.5 ([M–H])⁻.

Step 3: In analogy to example 1, step 1, from (3S,4R)-4-(4-fluoro-phenyl)-piperidine-1,3-dicarboxylic acid 1-tert-butyl ester and 1-(5-chloro-2-methylphenyl)-piperazine was prepared (3S,4R)-3-[4-(5-chloro-2-methyl-phenyl)-piperazine-1-carbonyl]-4-(4-fluoro-phenyl)-piperidine-1-carboxylic acid tert-butyl ester as a light yellow foam, MS: 516.3 ([M+H, 1Cl])⁺.

Step 4: In analogy to example 22, step 4, from (3S,4R)-3-[4-(5-chloro-2-methyl-phenyl)-piperazine-1-carbonyl]-4-(4-fluoro-phenyl)-piperidine-1-carboxylic acid tert-butyl ester was prepared [4-(5-chloro-2-methyl-phenyl)-piperazin-1-yl]-[(3S,4R)-4-(4-fluoro-phenyl)-piperidin-3-yl]-methanone hydrochloride as a white foam, MS: 416.4 ([M+H, 1Cl])⁺.

Step 5: In analogy to example 1, step 3, from [4-(5-chloro-2-methyl-phenyl)-piperazin-1-yl]-[(3S,4R)-4-(4-fluoro-phenyl)-piperidin-3-yl]-methanone hydrochloride and 3-chlorobenzenesulfonyl chloride was prepared [(3S,4R)-1-(3-chloro-benzenesulfonyl)-4-(4-fluoro-phenyl)-piperidin-3-yl]-[4-(5-chloro-2-methyl-phenyl)-piperazin-1-yl]-methanone as a white foam, MS: 590.3 ([M+H, 1Cl])⁺.

Example 56

[(3S,4R)-1-(2-Chloro-benzenesulfonyl)-4-(4-fluoro-phenyl)-piperidin-3-yl]-[4-(5-chloro-2-methyl-phenyl)-piperazin-1-yl]-methanone In analogy to example 1, step 3, from [4-(5-chloro-2-methyl-phenyl)-piperazin-1-yl]-[(3S,4R)-4-(4-fluoro-phenyl)-piperidin-3-yl]-methanone hydrochloride and 2-chlorobenzenesulfonyl chloride was prepared [(3S,4R)-1-(2-chlorobenzenesulfonyl)-4-(4-fluoro-phenyl)-piperidin-3-yl]-[4-(5-chloro-2-methyl-phenyl)-piperazin-1-yl]-methanone as a white foam, MS: 590.3 ([M+H, 1Cl])$^+$.

Example 57

[4-(5-Chloro-2-methyl-phenyl)-piperazin-1-yl]-[(3S,4R)-4-(4-fluoro-phenyl)-1-(pyridine-3-sulfonyl)-piperidin-3-yl]-methanone In analogy to example 1, step 3, from [4-(5-chloro-2-methyl-phenyl)-piperazin-1-yl]-[(3S,4R)-4-(4-fluoro-phenyl)-piperidin-3-yl]-methanone hydrochloride and pyridine-3-sulfonyl chloride was prepared [4-(5-chloro-2-methyl-phenyl)-piperazin-1-yl]-[(3S,4R)-4-(4-fluoro-phenyl)-1-(pyridine-3-sulfonyl)-piperidin-3-yl]-methanone as a white foam, MS: 557.1 ([M+H, 1Cl])$^+$.

Example 58

[(3S,4S) or (3R,4R)-1-(3-Chloro-benzenesulfonyl)-4-(2-fluoro-4-methyl-phenyl)-piperidin-3-yl]-[4-(5-chloro-2-methyl-phenyl)-piperazin-1-yl]-methanone Step 1: In analogy to example 46, step 1, from 4-trifluoromethanesulfonyloxy-5,6-dihydro-2H-pyridine-1,3-dicarboxylic acid 1-tert-butyl ester 3-methyl ester (CAS Reg. No. [161491-25-4]) and 2-fluoro-4-methylphenylzinc bromide (CAS Reg. No. [737797-14-7]) was prepared 4-(2-fluoro-4-methyl-phenyl)-5,6-dihydro-2H-pyridine-1,3-dicarboxylic acid 1-tert-butyl ester 3-methyl ester as light yellow oil, MS: 350.4 ([M+H])$^+$.
Step 2: In analogy to example 46, step 2, 4-(2-fluoro-4-methyl-phenyl)-5,6-dihydro-2H-pyridine-1,3-dicarboxylic acid 1-tert-butyl ester 3-methyl ester was prepared 4-(2-fluoro-4-methyl-phenyl)-5,6-dihydro-2H-pyridine-1,3-dicarboxylic acid 1-tert-butyl ester as a white solid, MS: 334.2 (M-H)$^-$.
Step 3: In analogy to example 46, step 3 from 4-(2-fluoro-4-methyl-phenyl)-5,6-dihydro 2H-pyridine-1,3-dicarboxylic acid 1-tert-butyl ester using [Ru(OAc)$_2$((R)-(2-furyl)-MeO-BIPHEP)] as catalyst for the enantioselective hydrogenation was prepared (3S,4S) or (3R,4R)-4-(2-fluoro-4-methyl-phenyl)-piperidine-1,3-dicarboxylic acid 1-tert-butyl ester as a white foam, MS: 336.2 (M-H)$^-$; [α]$_D$=-62.82 (c=0.962 g/100 mL, CHCl$_3$).
Step 4: In analogy to example 1, step 1, from (3S,4S) or (3R,4R)-4-(2-fluoro-4-methyl-phenyl)-piperidine-1,3-dicarboxylic acid 1-tert-butyl ester and 1-(5-chloro-2-methylphenyl)-piperazine was prepared (3S,4S) or (3R,4R)-3-[4-(5-chloro-2-methyl-phenyl)-piperazine-1-carbonyl]-4-(2-fluoro-4-methyl-phenyl)-piperidine-1-carboxylic acid tert-butyl ester as a white foam, MS: 530.3 ([M+H, 1Cl])$^+$.
Step 5: In analogy to example 22, step 4, from (3S,4S) or (3R,4R)-3-[4-(5-chloro-2-methyl-phenyl)-piperazine-1-carbonyl]-4-(2-fluoro-4-methyl-phenyl)-piperidine-1-carboxylic acid tert-butyl ester was prepared (3S,4S) or (3R,4R)-[4-(5-chloro-2-methyl-phenyl)-piperazin-1-yl]-[4-(2-fluoro-4-methyl-phenyl)-piperidin-3-yl]-methanone hydrochloride as crude product, MS: 430.4 ([M+H, 1Cl])$^+$.
Step 6: In analogy to example 1, step 3, from (3S,4S) or (3R,4R)-[4-(5-chloro-2methyl-phenyl)-piperazin-1-yl]-[4-(2-fluoro-4-methyl-phenyl)-piperidin-3-yl]-methanone hydrochloride and 3-chlorobenzenesulfonyl chloride was prepared [(3S,4S) or (3R,4R)-1-(3-chloro-benzenesulfonyl)-4-(2-fluoro-4-methyl-phenyl)-piperidin-3-yl]-[4-(5-chloro-2-methyl-phenyl)-piperazin-1-yl]-methanone as a white foam, MS: 604.1 ([M+H, 1Cl])$^+$; [α]$_D$=+14.03 (c=0.442 g/100 mL, CHCl$_3$).

Example 59

[(3S,4S) or (3R,4R)-1-(2-Chloro-benzenesulfonyl)-4-(2-fluoro-4-methyl-phenyl)-piperidin-3-yl]-[4-(5-chloro-2-methyl-phenyl)-piperazin-1-yl]-methanone In analogy to example 1, step 3, from [4-(5-chloro-2-methyl-phenyl)-piperazin-1-yl]-[(3S,4S)-4-(2-fluoro-4-methyl-phenyl)-piperidin-3-yl]-methanone hydrochloride and 2-chlorobenzenesulfonyl chloride was prepared [(3S,4S) or (3R,4R)-1-(2-chloro-benzenesulfonyl)-4-(2-fluoro-4-methyl-phenyl)-piperidin-3-yl]-[4-(5-chloro-2-methyl-phenyl)-piperazin-1yl]-methanone as a white foam, MS: 604.1 ([M+H, 1Cl])$^+$; [α]$_D$=-8.8 (c=0.659 g/100 mL, CHCl$_3$).

Example 60

(3S,4S) or (3R,4R)-[4-(5-Chloro-2-methyl-phenyl)-piperazin-1-yl]-[4-(2-fluoro-4-methyl-phenyl)-1-(2-trifluoromethyl-benzenesulfonyl)-piperidin-3-yl]-methanone In analogy to example 1, step 3, from [4-(5-chloro-2-methyl-phenyl)-piperazin-1-yl]-[(3S,4S)-4-(2-fluoro-4-methyl-phenyl)-piperidin-3-yl]-methanone hydrochloride and 2-(trifluoromethyl)benzenesulfonyl chloride was prepared (3S,4S) or (3R,4R)-[4-(5-chloro-2-methyl-phenyl)-piperazin-1-yl]-[4-(2-fluoro-4-methyl-phenyl)-1-(2-trifluoromethyl-benzenesulfonyl)-piperidin-3-yl]-methanone as a white foam, MS: 638.3 ([M+H, 1Cl])$^+$; [α]$_D$=-13.63 (c=0.477 g/100 mL, CHCl$_3$).

Example 61

(3S,4S) or (3R,4R)-[4-(5-Chloro-2-methyl-phenyl)-piperazin-1-yl]-[4-(2-fluoro-4-methyl-phenyl)-1-(pyridine-3-sulfonyl)-piperidin-3-yl]-methanone In analogy to example 1, step 3, from [4-(5-chloro-2-methyl-phenyl)-piperazin-1-yl]-[(3S,4S)-4-(2-fluoro-4-methyl-phenyl)-piperidin-3-yl]-methanone hydrochloride and pyridine-3-sulfonyl chloride hydrochloride was prepared (3S,4S) or (3R,4R)-[4-(5-chloro-2-methyl-phenyl)-piperazin-1-yl]-[4-(2-fluoro-4-methyl-phenyl)-1-(pyridine-3-sulfonyl)-piperidin-3-yl]-methanone as a white foam, MS: 571.3 ([M+H, 1Cl])$^+$; [α]$_D$=+0.67 (c=0.446 g/100 mL, CHCl$_3$).

Example 62

(3S,4S) or (3R,4R)-[4-(5-Chloro-2-methyl-phenyl)-piperazin-1-yl]-[4-(2-fluoro-methyl-phenyl)-1-(propane-2-sulfonyl)-piperidin-3-yl]-methanone In analogy to example 1, step 3, from [4-(5-chloro-2-methyl-phenyl)-piperazin-1-yl]-[(3S,4S)-4-(2-fluoro-4-methyl-phenyl)-piperidin-3-yl]-methanone hydrochloride and 2-propanesulfonyl chloride was prepared (3S,4S) or (3R,4R)-[4-(5-chloro-2-methyl-phenyl)-piperazin-1-yl]-[4-(2-fluoro-4-methyl-phenyl)-1-(propane-2-sulfonyl)-piperidin-3-yl]-methanone as a white foam, MS: 536.4 ([M+H, 1Cl])$^+$; [α]$_D$=-16.22 (c=0.746 g/100 mL, CHCl$_3$).

Example 63

[(3S,4R)-1-(3-Chloro-benzenesulfonyl)-4-phenyl-piperidin-3-yl]-[4-(5-chloro-2-methyl-phenyl)-piperazin-1-yl]-methanone Step 1: In analogy to example 52, steps 2-3, from (3R,4R)-4-phenyl-piperidine-1,3-dicarboxylic acid 1-tert-butyl ester (CAS Reg. No.: [197900-84-8]) was prepared (3S,4S)-4-phenyl-piperidine-1,3-dicarboxylic acid 1-tert-butyl ester as an off-white solid, MS: 304.3 (M−H)⁻.

Step 2: In analogy to example 1, step 1, from 3S,4S)-4-phenyl-piperidine-1,3-dicarboxylic acid 1-tert-butyl ester and 1-(5-chloro-2-methylphenyl)-piperazine was prepared (3S,4R)-3-[4-(5-chloro-2-methyl-phenyl)-piperazine-1-carbonyl]-4-phenyl-piperidine-1-carboxylic acid tert-butyl ester (Cas Reg. No. [652971-20-5]) as a white foam, MS: 500.5 ([M+H, 1Cl])⁺.

Step 3: In analogy to example 22, step 4, from (3S,4R)-3-[4-(5-chloro-2-methyl-phenyl)-piperazine-1-carbonyl]-4-phenyl-piperidine-1-carboxylic acid tert-butyl ester and 1-(5-chloro-2-methylphenyl)-piperazine was prepared [4-(5-chloro-2-methyl-phenyl)-piperazin-1-yl]-((3S,4R)-4-phenyl-piperidin-3-yl)-methanone hydrochloride as a white foam, MS: 400.5 ([M+H, 1Cl])⁺.

Step 4: In analogy to example 1, step 3 using iPr₂NEt as base and CH₂Cl₂ as solvent, from [4-(5-chloro-2-methyl-phenyl)-piperazin-1-yl]-((3S,4R)-4-phenyl-piperidin-3-yl)-methanone hydrochloride and 3-chlorobenzene-sulfonyl chloride was prepared [(3S,4R)-1-(3-chloro-benzenesulfonyl)-4-phenyl-piperidin-3-yl]-[4-(5-chloro-2-methyl-phenyl)-piperazin-1-yl]-methanone as a white foam, MS: 572.15 ([M+H, 1Cl])⁺.

Example 64

[4-(5-Chloro-2-methyl-phenyl)-piperazin-1-yl]-[(3S,4R)-4-phenyl-1-(2-trifluoromethyl-benzenesulfonyl)-piperidin-3-yl]-methanone In analogy to example 63, step 4, from [4-(5-chloro-2-methyl-phenyl)-piperazin-1-yl]-((3S,4R)-4-phenyl-piperidin-3-yl)-methanone hydrochloride and 2-(trifluoromethyl)-benzenesulfonyl chloride was prepared [4-(5-chloro-2-methyl-phenyl)-piperazin-1-yl]-[(3S,4R)-4-phenyl-1-(2-trifluoromethyl-benzenesulfonyl)-piperidin-3-yl]-methanone as a white foam, MS: 606.2 ([M+H, 1Cl])⁺.

Example 65

[4-(5-Chloro-2-methyl-phenyl)-piperazin-1-yl]-[(3S,4R)-4-phenyl-1-(pyridine-3-sulfonyl)-piperidin-3-yl]-methanone In analogy to example 63, step 4, from [4-(5-chloro-2-methyl-phenyl)-piperazin-1-yl]-((3S,4R)-4-phenyl-piperidin-3-yl)-methanone hydrochloride and pyridine-3-sulfonyl chloride hydrochloride was prepared [4-(5-chloro-2-methyl-phenyl)-piperazin-1-yl]-[(3S,4R)-4-phenyl-1-(pyridine-3-sulfonyl)-piperidin-3-yl]-methanone as a white foam, MS: 539.3 ([M+H, 1Cl])⁺.

Example 66

[(3S,4R)-1-(3-Chloro-benzenesulfonyl)-4-o-tolyl-piperidin-3-yl]-[4-(5-chloro-2-methyl-phenyl)-piperazin-1-yl]-methanone Step 1: In analogy to example 46, step 1 from 4-o-tolyl-5,6-dihydro-2H-pyridine-1,3-dicarboxylic acid 1-tert-butyl ester using [Ru(OAc)₂((S)-(BITIANP))] as catalyst for the enantioselective hydrogenation was prepared (3R,4R)-4-o-tolyl-piperidine-1,3-dicarboxylic acid 1-tert-butyl ester as a white foam, MS: 318.2 ([M−H])⁻.

Step 2: In analogy to example 52, steps 2-3, from (3R,4R)-4-o-tolyl-piperidine-1,3-dicarboxylic acid 1-tert-butyl ester was prepared (3S,4R)-4-o-tolyl-piperidine-1,3-dicarboxylic acid 1-tert-butyl ester as a white solid, MS: 318.4 ([M−H])⁻.

Step 3: In analogy to example 1, step 1, from (3S,4R)-4-o-tolyl-piperidine-1,3-dicarboxylic acid 1-tert-butyl ester and 1-(5-chloro-2-methylphenyl)-piperazine was prepared (3S,4R)-3-[4-(5-chloro-2-methyl-phenyl)-piperazine-1-carbonyl]-4-o-tolyl-piperidine-1-carboxylic acid tert-butyl ester as a white foam, MS: 512.5 ([M+H])⁺.

Step 4: In analogy to 22 step 4, from (3S,4R)-3-[4-(5-chloro-2-methyl-phenyl)-piperazine-1-carbonyl]-4-o-tolyl-piperidine-1-carboxylic acid tert-butyl ester was prepared [4-(5-chloro-2-methyl-phenyl)-piperazin-1-yl]-((3S,4R)-4-o-tolyl-piperidin-3-yl)-methanone hydrochloride as crude product, MS: 512.5 ([M+H, 1Cl])⁺.

Step 5: In analogy to example 63, step 4, from 4-(5-chloro-2-methyl-phenyl)-piperazin-1-yl]-((3S,4R)-4-o-tolyl-piperidin-3-yl)-methanone hydrochloride and 3-chlorobenzene-sulfonyl chloride was prepared [(3S,4R)-1-(3-chloro-benzenesulfonyl)-4-o-tolyl-piperidin-3-yl]-[4-(5-chloro-2-methyl-phenyl)-piperazin-1-yl]-methanone as a white foam, MS: 586.1 ([M+H, 1Cl])⁺.

Example 67

[4-(5-Chloro-2-methyl-phenyl)-piperazin-1-yl]-[(3S,4R)-4-o-tolyl-1-(2-trifluoromethyl-benzenesulfonyl)-piperidin-3-yl]-methanone In analogy to example 63, step 4, from 4-(5-chloro-2-methyl-phenyl)-piperazin-1-yl]-((3S,4R)-4-o-tolyl-piperidin-3-yl)-methanone hydrochloride and 2-(trifluoromethyl)-benzenesulfonyl chloride was prepared [4-(5-chloro-2-methyl-phenyl)-piperazin-1-yl]-[(3S,4R)-4-o-tolyl-1-(2-trifluoromethyl-benzenesulfonyl)-piperidin-3-yl]-methanone as a white foam, MS: 620.3 ([M+H, 1Cl])⁺.

Example 68

[4-(5-Chloro-2-methyl-phenyl)-piperazin-1-yl]-[(3S,4R)-1-(pyridine-3-sulfonyl)-4-o-tolyl-piperidin-3-yl]-methanone In analogy to example 63, step 4, from 4-(5-chloro-2-methyl-phenyl)-piperazin-1-yl]-((3S,4R)-4-o-tolyl-piperidin-3-yl)-methanone hydrochloride and pyridine-3-sulfonyl chloride hydrochloride was prepared [4-(5-chloro-2-methyl-phenyl)-piperazin-1-yl]-[(3S,4R)-1-(pyridine-3-sulfonyl)-4-o-tolyl-piperidin-3-yl]-methanone as a white foam, MS: 553.2 ([M+H, 1Cl])⁺.

Example 69

[(3S,4R) or (3R,4S)-1-(3-Chloro-benzenesulfonyl)-4-(2,4-difluoro-phenyl)-piperidin-3-yl]-[4-(5-chloro-2-methyl-phenyl)-piperazin-1-yl]-methanone Step 1: In analogy to example 46, step 1 from 4-trifluoromethanesulfonyloxy-5,6-dihydro-2H-pyridine-1,3-dicarboxylic acid 1-tert-butyl ester 3-methyl ester (CAS Reg. No. [161491-25-4]) and 2,4-difluorophenylzinc bromide was prepared 4-(2,4-difluoro-phenyl)-5,6-dihydro-2H-pyridine-1,3-dicarboxylic acid 1-tert-butyl ester as a light yellow oil, MS: 354.2 (M+H)⁺.

Step 2: In analogy to example 46, step 2, from 4-(2,4-difluoro-phenyl)-5,6-dihydro-2H-pyridine-1,3-dicarboxylic acid 1-tert-butyl ester 3-methyl ester was prepared 4-(2,4-difluoro-phenyl)-5,6-dihydro-2H-pyridine-1,3-dicarboxylic acid 1-tert-butyl ester as a white solid, 338.1 (M−H)⁻.

Step 3: In analogy to example 46, step 3, from 4-(2,4-difluoro-phenyl)-5,6-dihydro-2H-pyridine-1,3-dicarboxylic acid 1-tert-butyl ester using [Ru(OAc)$_2$((S)-(BITIANP))] as catalyst for the enantioselective hydrogenation was prepared (3R,4R) or (3S,4S)-4-(2,4-difluoro-phenyl)-piperidine-1,3-dicarboxylic acid 1-tert-butyl ester as white solid, MS: 340.1 ([M−H])⁻; [α]$_D$=+61.90 (c=0.806 g/100 mL, CHCl$_3$).

Step 4: In analogy to example 52, steps 2-3, from (3R,4R) or (3S,4S)-4-(2,4-difluoro-phenyl)-piperidine-1,3-dicarboxylic acid 1-tert-butyl ester was prepared (3S,4R) or (3R,4S)-4-(2,4-difluoro-phenyl)-piperidine-1,3-dicarboxylic acid 1-tert-butyl ester as an off-white foam, MS: 340.4 ([M−H])⁻; [α]$_D$=−8.11 (c=0.271 g/100 mL, CHCl$_3$).

Step 5: In analogy to example 1, step 1, from (3S,4R) or (3R,4S)-4-(2,4-difluoro-phenyl)-piperidine-1,3-dicarboxylic acid 1-tert-butyl ester and 1-(5-chloro-2-methylphenyl)-piperazine was prepared (3S,4R) or (3R,4S)-3-[4-(5-chloro-2-methyl-phenyl)-piperazine-1-carbonyl]-4-(2,4-difluoro-phenyl)-piperidine-1-carboxylic acid tert-butyl ester as a white foam, MS: 534.2 ([M+H, 1Cl])⁺.

Step 6: In analogy to example 22, step 4, from (3S,4R) or (3R,4S)-3-[4-(5-chloro-2-methyl-phenyl)-piperazine-1-carbonyl]-4-(2,4-difluoro-phenyl)-piperidine-1-carboxylic acid tert-butyl ester was prepared (3S,4R) or (3R,4S)-[4-(5-chloro-2-methyl-phenyl)-piperazin-1-yl]-[4-(2,4-difluoro-phenyl)-piperidin-3-yl]-methanone hydrochloride as crude product, MS: 434.3 ([M+H, 1Cl])⁺.

Step 7: In analogy to example 63, step 4, from (3S,4R) or (3R,4S)-[4-(5-chloro-2-methyl-phenyl)-piperazin-1-yl]-[4-(2,4-difluoro-phenyl)-piperidin-3-yl]-methanone hydrochloride and 3-chlorobenzenesulfonyl chloride was prepared [(3S,4R) or (3R,4S)-1-(3-chloro-benzenesulfonyl)-4-(2,4-difluoro-phenyl)-piperidin-3-yl]-[4-(5-chloro-2-methyl-phenyl)-piperazin-1-yl]-methanone as a white foam, MS: 607.1 ([M+H, 1Cl])⁺; [α]$_D$=−66.8 (c=0.434 g/100 mL, CHCl$_3$).

Example 70

(3S,4R) or (3R,4S)-[4-(5-Chloro-2-methyl-phenyl)-piperazin-1-yl]-[4-(2,4-difluoro-phenyl)-1-(pyridine-3-sulfonyl)-piperidin-3-yl]-methanone In analogy to example 63, step 4, from (3S,4R) or (3R,4S)-[4-(5-chloro-2-methyl-phenyl)-piperazin-1-yl]-[4-(2,4-difluoro-phenyl)-piperidin-3-yl]-methanone hydrochloride and pyridine-3-sulfonyl chloride hydrochloride was prepared (3S,4R) or (3R,4S)-[4-(5-chloro-2-methyl-phenyl)-piperazin-1-yl]-[(3S,4R)-4-(2,4-difluoro-phenyl)-1-(pyridine-3-sulfonyl)-piperidin-3-yl]-methanone as a white foam, MS: 575.4 ([M+H, 1Cl])⁺; [α]$_D$=−66.76 (c=0.454 g/100 mL, CHCl$_3$).

Example 71

[(3S,4S)-1-(3-Chloro-benzenesulfonyl)-4-phenyl-piperidin-3-yl]-[4-(5-chloro-2-methyl-phenyl)-piperazin-1-yl]-methanone Step 1: In analogy to example 1, step 1, from (3S,4S)-4-phenyl-piperidine-1,3-dicarboxylic acid 1-tert-butyl ester (CAS Reg. No.: [197900-77-9]) and 1-(5-chloro-2-methylphenyl)-piperazine was prepared (3S,4S)-3-[4-(5-chloro-2-methyl-phenyl)-piperazine-1-carbonyl]-4-phenyl-piperidine-1-carboxylic acid tert-butyl ester as a white foam, MS: 498.5 ([M+H, 1Cl])⁺.

Step 2: In analogy to example 22, step 4, from (3S,4S)-3-[4-(5-chloro-2-methyl-phenyl-piperazine-1-carbonyl]-4-phenyl-piperidine-1-carboxylic acid tert-butyl ester was prepared [4-(5-chloro-2-methyl-phenyl)-piperazin-1-yl]-((3S,4S)-4-phenyl-piperidin-3-yl)-methanone hydrochloride as crude product, MS: 398.4 ([M+H, 1Cl])⁺.

Step 3: In analogy to example 63, step 4, from [4-(5-chloro-2-methyl-phenyl)-piperazin-1-yl]-((3S,4S)-4-phenyl-piperidin-3-yl)-methanone hydrochloride and 3-chlorobenzenesulfonyl chloride was prepared [(3S,4S)-1-(3-chloro-benzenesulfonyl)-4-phenyl-piperidin-3-yl]-[4-(5-chloro-2-methyl-phenyl)-piperazin-1-yl]-methanone as a white foam, MS: 572.2 ([M+H, 1Cl])⁺.

Example 72

[4-(5-Chloro-2-methyl-phenyl)-piperazin-1-yl]-[(3S,4S)-4-phenyl-1-(2-trifluoromethyl-benzenesulfonyl)-piperidin-3-yl]-methanone In analogy to example 63, step 4, from [4-(5-chloro-2-methyl-phenyl)-piperazin-1-yl]-((3S,4S)-4-phenyl-piperidin-3-yl)-methanone hydrochloride and 2-(trifluoromethyl)-benzenesulfonyl chloride was prepared [4-(5-chloro-2-methyl-phenyl)-piperazin-1-yl]-[(3S,4S)-4-phenyl-1-(2-trifluoromethyl-benzenesulfonyl)-piperidin-3-yl]-methanone as a white foam, MS: 606.0 ([M+H, 1Cl])⁺.

Example 73

[4-(5-Chloro-2-methyl-phenyl)-piperazin-1-yl]-[(3S,4S)-4-phenyl-1-(pyridine-3-sulfonyl)-piperidin-3-yl]-methanone In analogy to example 63, step 4, from [4-(5-chloro-2-methyl-phenyl)-piperazin-1-yl]-((3S,4S)-4-phenyl-piperidin-3-yl)-methanone hydrochloride and pyridine-3-sulfonyl chloride hydrochloride was prepared [4-(5-chloro-2-methyl-phenyl)-piperazin-1-yl]-[(3S,4S)-4-phenyl-1-(pyridine-3-sulfonyl)-piperidin-3-yl]-methanone as a white foam, MS: 539.2 ([M+H, 1Cl])⁺.

Example 74

[4-(5-Chloro-2-methyl-phenyl)-piperazin-1-yl]-[(3S,4S)-4-phenyl-1-(propane-2-sulfonyl)-piperidin-3-yl]-methanone In analogy to example 63, step 4, from [4-(5-chloro-2-methyl-phenyl)-piperazin-1-yl]-((3S,4S)-4-phenyl-piperidin-3-yl)-methanone hydrochloride and 2-propanesulfonyl chloride was prepared [4-(5-chloro-2-methyl-phenyl)-piperazin-1-yl]-[(3S,4S)-4-phenyl-1-(propane-2-sulfonyl)-piperidin-3-yl]-methanone as a white foam, MS: 504.1 ([M+H, 1Cl])⁺.

Example 75

[4-(5-Chloro-2-methyl-phenyl)-piperazin-1-yl]-((3S,4S)-1-methanesulfonyl-4-phenyl-piperidin-3-yl)-methanone In analogy to example 63, step 4, from [4-(5-chloro-2-methyl-phenyl)-piperazin-1-yl]-((3S,4S)-4-phenyl-piperidin-3-yl)-methanone hydrochloride and methanesulfonyl chloride was prepared [4-(5-chloro-2-methyl-phenyl)-piperazin-1-yl]-((3S,4S)-1-methanesulfonyl-4-phenyl-piperidin-3-yl)-methanone as a white foam, MS: 476.1 ([M+H, 1Cl])⁺.

Example 76

[(3S,4S)-1-(3-Chloro-benzenesulfonyl)-4-o-tolyl-piperidin-3-yl]-[4-(5-chloro-2-methyl-phenyl)-piperazin-1-yl]-methanone Step 1: In analogy to example 1, step 1, from (3S,4S)-4-o-tolyl-piperidine-1,3-dicarboxylic acid 1-tert-butyl ester (example 46, step 3) and 1-(5-chloro-2-methylphenyl)-piperazine was prepared (3S,4S)-3-[4-(5-chloro-2-methyl-phenyl)-piperazine-1-carbonyl]-4-o-tolyl-piperidine-1-carboxylic acid tert-butyl ester as a white foam, MS: 512.3 ([M+H, 1Cl])⁺.

Step 2: In analogy to example 22, step 4, from (3S,4S)-3-[4-(5-chloro-2-methyl-phenyl-piperazine-1-carbonyl]-4-o-tolyl-piperidine-1-carboxylic acid tert-butyl ester was prepared [4-(5-chloro-2-methyl-phenyl)-piperazin-1-yl]-((3S,4S)-4-o-tolyl-piperidin-3-yl)-methanone hydrochloride as crude product, MS: 412.5 ([M+H, 1Cl])⁺.

Step 3: In analogy to example 63, step 4, from [4-(5-chloro-2-methyl-phenyl)-piperazin-1-yl]-((3S,4S)-4-o-tolyl-piperidin-3-yl)-methanone hydrochloride and 3-chlorobenzenesulfonyl chloride was prepared [(3S,4S)-1-(3-chloro-benzenesulfonyl)-4-o-tolyl-piperidin-3-yl]-[4-(5-chloro-2-methyl-phenyl)-piperazin-1-yl]-methanone as a white foam, MS: 586.2 ([M+H, 1Cl])⁺.

Example 77

[4-(5-Chloro-2-methyl-phenyl)-piperazin-1-yl]-[(3S,4S)-4-o-tolyl-1-(2-trifluoromethyl-benzenesulfonyl)-piperidin-3-yl]-methanone In analogy to example 63, step 4, from [4-(5-chloro-2-methyl-phenyl)-piperazin-1-yl]-((3S,4S)-4-o-tolyl-piperidin-3-yl)-methanone hydrochloride and 2-(trifluoromethyl)-benzenesulfonyl chloride was prepared [4-(5-chloro-2-methyl-phenyl)-piperazin-1-yl]-[(3S,4S)-4-o-tolyl-1-(2-trifluoromethyl-benzenesulfonyl)-piperidin-3-yl]-methanone as a white foam, MS: 620.5 ([M+H, 1Cl])⁺.

Example 78

[4-(5-Chloro-2-methyl-phenyl)-piperazin-1-yl]-[(3S,4S)-1-(pyridine-3-sulfonyl)-4-o-tolyl-piperidin-3-yl]-methanone In analogy to example 63, step 4, from [4-(5-chloro-2-methyl-phenyl)-piperazin-1-yl]-((3S,4S)-4-o-tolyl-piperidin-3-yl)-methanone hydrochloride and pyridine-3-sulfonyl chloride hydrochloride was prepared [4-(5-chloro-2-methyl-phenyl)-piperazin-1-yl]-[(3S,4S)-1-(pyridine-3-sulfonyl)-4-o-tolyl-piperidin-3-yl]-methanone as a white foam, MS: 553.2 ([M+H, 1Cl])⁺.

Example 79

[4-(5-Chloro-2-methyl-phenyl)-piperazin-1-yl]-((3S,4S)-1-methanesulfonyl-4-o-tolyl-piperidin-3-yl)-methanone In analogy to example 63, step 4, from [4-(5-chloro-2-methyl-phenyl)-piperazin-1-yl]-((3S,4S)-4-o-tolyl-piperi-din-3-yl)-methanone hydrochloride and methanesulfonyl chloride was prepared [4-(5-chloro-2-methyl-phenyl)-piperazin-1-yl]-((3S,4S)-1-methanesulfonyl-4-o-tolyl-piperidin-3-yl)-methanone as a white foam, MS: 490.2 ([M+H, 1Cl])⁺.

Example 80

[(3S,4S) or (3R,4R)-1-(3-Chloro-benzenesulfonyl)-4-(4-fluoro-2-methyl-phenyl)-piperidin-3-yl]-[4-(5-chloro-2-methyl-phenyl)-piperazin-1-yl]-methanone Step 1: In analogy to example 46, steps 1-2, from 4-trifluoromethanesulfonyloxy-5,6-dihydro-2H-pyridine-1,3-dicarboxylic acid 1-tert-butyl ester 3-methyl ester (CAS Reg. No. [161491-25-4]) and 4-fluoro-6-methylphenylzinc bromide (previously prepared from 4-fluoro-6-methylphenyl-magnesium bromide and zinc chloride) was prepared 4-(4-fluoro-2-methyl-phenyl)-5,6-dihydro-2H-pyridine-1,3-dicarboxylic acid 1-tert-butyl ester as a white solid, MS: 334.3 (M−H)⁻.

Step 2: In analogy to example 46, step 3, from 4-(4-fluoro-2-methyl-phenyl)-5,6-dihydro-2H-pyridine-1,3-dicarboxylic acid 1-tert-butyl ester using [Ru(OAc)₂((R)-(2-furyl)-MeOBIPHEP)] as catalyst for the enantioselective hydrogenation was prepared (3S,4S) or (3R,4R)-4-(4-fluoro-2-methyl-phenyl)-piperidine-1,3-dicarboxylic acid 1-tert-butyl ester as a white foam, MS: 336.2 (M−H)⁻; [α]$_D$=−52.53 (c=0.643 g/100 mL, CHCl₃).

Step 3: In analogy to example 1, step 1, from (3S,4S) or (3R,4R)-4-(4-fluoro-2-phenyl)-piperidine-1,3-dicarboxylic acid 1-tert-butyl ester and 1-(5-chloro-2-methylphenyl)-piperazine was prepared (3S,4S) or (3R,4R)-3-[4-(5-chloro-2-methyl-phenyl)-piperazine-1-carbonyl]-4-(4-fluoro-2-methyl-phenyl)-piperidine-1-carboxylic acid tert-butyl ester as a white foam, MS: 530.2 ([M+H, 1Cl])⁺.

Step 4: In analogy to example 22, step 4, from (3S,4S) or (3R,4R)-3-[4-(5-chloro-2-methyl-phenyl)-piperazine-1-carbonyl]-4-(4-fluoro-2-methyl-phenyl)-piperidine-1-carboxylic acid tert-butyl ester was prepared [4-(5-chloro-2-methyl-phenyl)-piperazin-1-yl]-[(3S,4S) or (3R,4R)-4-(4-fluoro-2-methyl-phenyl)-piperidin-3-yl]-methanone hydrochloride as crude product, MS: 430.4 ([M+H, 1Cl])⁺.

Step 5: In analogy to example 63, step 4, from [4-(5-chloro-2-methyl-phenyl)-piperazin-1-yl]-[(3S,4S) or (3R,4R)-4-(4-fluoro-2-methyl-phenyl)-piperidin-3-yl]-methanone hydrochloride and 3-chlorobenzenesulfonyl chloride was prepared [(3S,4S) or (3R,4R)-1-(3-chloro-benzenesulfonyl)-4-(4-fluoro-2-methyl-phenyl)-piperidin-3-yl]-[4-(5-chloro-2-methyl-phenyl)-piperazin-1-yl]-methanone as a white foam, MS: 604.0 ([M+H, 1Cl])⁺; [α]$_D$=−32.13 (c=0.426 g/100 mL, CHCl₃).

Example 81

[4-(5-Chloro-2-methyl-phenyl)-piperazin-1-yl]-[(3S,4S) or (3R,4R)-4-(4-fluoro-2-methyl-phenyl)-1-(2-trifluoromethyl-benzenesulfonyl)-piperidin-3-yl]-methanone In analogy to example 63, step 4, from [4-(5-chloro-2-methyl-phenyl)-piperazin-1-yl]-[(3S,4S) or (3R,4R)-4-(4-fluoro-2-methyl-phenyl)-piperidin-3-yl]-methanone hydrochloride and 2-(trifluoromethyl)benzenesulfonyl chloride was prepared [4-(5-chloro-2-methyl-phenyl)-piperazin-1-yl]-[(3S,4S) or (3R,4R)-4-(4-fluoro-2-methyl-phenyl)-1-(2-trifluoromethyl-benzenesulfonyl)-piperidin-3-yl]-methanone as a white foam, MS: 638.2 ([M+H, 1Cl])⁺; [α]_D=−60.75 (c=0.423 g/100 mL, CHCl₃).

Example 82

[4-(5-Chloro-2-methyl-phenyl)-piperazin-1-yl]-[(3S,4S) or (3R,4R)-4-(4-fluoro-methyl-phenyl)-1-(pyridine-3-sulfonyl)-piperidin-3-yl]-methanone In analogy to example 63, step 4, from [4-(5-chloro-2-methyl-phenyl)-piperazin-1-yl]-[(3S,4S) or (3R,4R)-4-(4-fluoro-2-methyl-phenyl)-piperidin-3-yl]-methanone hydrochloride and pyridine-3-sulfonyl chloride hydrochloride was prepared [4-(5-chloro-2-methyl-phenyl)-piperazin-1-yl]-[(3S,4S) or (3R,4R)-4-(4-fluoro-2-methyl-phenyl)-1-(pyridine-3-sulfonyl)-piperidin-3-yl]-methanone as a white foam, MS: 571.2 ([M+H, 1Cl])⁺; [α]_D=−49.92 (c=0.535 g/100 mL, CHCl₃).

Example 83

[4-(5-Chloro-2-methyl-phenyl)-piperazin-1-yl]-[(3S,4S) or (3R,4R)-4-(4-fluoro-2-methyl-phenyl)-1-methanesulfonyl-piperidin-3-yl]-methanone In analogy to example 63, step 4, from [4-(5-chloro-2-methyl-phenyl)-piperazin-1-yl]-[(3S,4S) or (3R,4R)-4-(4-fluoro-2-methyl-phenyl)-piperidin-3-yl]-methanone hydrochloride and methanesulfonyl chloride was prepared [4-(5-chloro-2-methyl-phenyl)-piperazin-1-yl]-[(3S,4S) or (3R,4R)-4-(4-fluoro-2-methyl-phenyl)-1-methanesulfonyl-piperidin-3-yl]-methanone as a white foam, MS: 508.3 ([M+H, 1Cl])⁺; [α]_D=−77.86 (c=0.434 g/100 mL, CHCl₃).

Example 84

[(3S,4S) or (3R,4R)-1-(3-Chloro-benzenesulfonyl)-4-(2,4-difluoro-phenyl)-piperidin-3-yl]-[4-(5-chloro-2-methyl-phenyl)-piperazin-1-yl]-methanone Step 1: In analogy to example 46, step 1, from 4-trifluoromethanesulfonyloxy-5,6-dihydro-2H-pyridine-1,3-dicarboxylic acid 1-tert-butyl ester 3-methyl ester (CAS Reg. No. [161491-25-4]) and 2,4-difluorophenylzinc bromide was prepared 4-(2,4-difluoro-phenyl)-5,6-dihydro-2H-pyridine-1,3-dicarboxylic acid 1-tert-butyl ester 3-methyl ester as a light yellow oil, MS: 354.2 ([M+H])⁺.

Step 2: In analogy to example 46, step 2, from 4-(2,4-difluoro-phenyl)-5,6-dihydro-2H-pyridine-1,3-dicarboxylic acid 1-tert-butyl ester 3-methyl ester was prepared 4-(2,4-difluoro-phenyl)-5,6-dihydro-2H-pyridine-1,3-dicarboxylic acid 1-tert-butyl ester as a white solid, MS: 338.0 (M−H)⁻.

Step 3: In analogy to example 46, step 3, from 4-(2,4-difluoro-phenyl)-5,6-dihydro-2H-pyridine-1,3-dicarboxylic acid 1-tert-butyl ester using [Ru(OAc)₂((S)-(BITIANP))] as catalyst for the enantioselective hydrogenation was prepared (3S,4S) or (3R,4R)-4-(2,4-difluoro-phenyl)-piperidine-1,3-dicarboxylic acid 1-tert-butyl ester as a white a white solid, MS: 340.1 (M−H)⁻; [α]_D=−61.33 (c=0.473 g/100 mL, CHCl₃).

Step 4: In analogy to example 1, step 1, from (3S,4S) or (3R,4R)-4-(2,4-difluoro-phenyl)-piperidine-1,3-dicarboxylic acid 1-tert-butyl ester and 1-(5-chloro-2-methylphenyl)-piperazine was prepared (3S,4S) or (3R,4R)-3-[4-(5-chloro-2-methyl-phenyl)-piperazine-1-carbonyl]-4-(2,4-difluoro-phenyl)-piperidine-1-carboxylic acid tert-butyl ester as a white foam, MS: 534.2 ([M+H, 1Cl])⁺.

Step 5: In analogy to example 22, step 4, from (3S,4S) or (3R,4R)-3-[4-(5-chloro-2-methyl-phenyl)-piperazine-1-carbonyl]-4-(2,4-difluoro-phenyl)-piperidine-1-carboxylic acid tert-butyl ester was prepared [4-(5-chloro-2-methyl-phenyl)-piperazin-1-yl]-[(3S,4S) or (3R,4R)-4-(2,4-difluoro-phenyl)-piperidin-3-yl]-methanone hydrochloride as crude product, MS: 434.5 ([M+H, 1Cl])⁺.

Step 6: In analogy to example 63, step 4, from 4-(5-chloro-2-methyl-phenyl)-piperazin-1-yl]-[(3S,4S) or (3R,4R)-4-(2,4-difluoro-phenyl)-piperidin-3-yl]-methanone hydrochloride and 3-chlorobenzenesulfonyl chloride was prepared [(3S,4S) or (3R,4R)-1-(3-chloro-benzenesulfonyl)-4-(2,4-difluoro-phenyl)-piperidin-3-yl]-[4-(5-chloro-2-methyl-phenyl)-piperazin-1-yl]-methanone as a white foam, MS: 608.0 ([M+H, 1Cl])⁺; [α]_D=+10.71 (c=0.392 g/100 mL, CHCl₃).

Example 85

[4-(5-Chloro-2-methyl-phenyl)-piperazin-1-yl]-[(3S,4S) or (3R,4R)-4-(2,4-difluoro-phenyl)-1-(2-trifluoromethyl-benzenesulfonyl)-piperidin-3-yl]-methanone In analogy to example 63, step 4, from 4-(5-chloro-2-methyl-phenyl)-piperazin-1-yl]-[(3S,4S) or (3R,4R)-4-(2,4-difluoro-phenyl)-piperidin-3-yl]-methanone hydrochloride and 2-(trifluoromethyl)benzenesulfonyl chloride was prepared [4-(5-chloro-2-methyl-phenyl)-piperazin-1-yl]-[(3S,4S) or (3R,4R)-4-(2,4-difluoro-phenyl)-1-(2-trifluoromethyl-benzenesulfonyl)-piperidin-3-yl]-methanone as a white foam, MS: 642.3 ([M+H, 1Cl])⁺; [α]_D=−22.86 (c=0.442 g/100 mL, CHCl₃).

Example 86

[4-(5-Chloro-2-methyl-phenyl)-piperazin-1-yl]-[(3S,4S) or (3R,4R)-4-(2,4-difluoro-phenyl)-1-(pyridine-3-sulfonyl)-piperidin-3-yl]-methanone In analogy to example 63, step 4, from 4-(5-chloro-2-methyl-phenyl)-piperazin-1-yl]-[(3S,4S) or (3R,4R)-4-(2,4-difluoro-phenyl)-piperidin-3-yl]-methanone hydrochloride and pyridine-3-sulfonyl chloride hydrochloride was prepared [4-(5-chloro-2-methyl-phenyl)-piperazin-1-yl]-[(3S,4S) or (3R,4R)-4-(2,4-difluoro-phenyl)-1-(pyridine-3-sulfonyl)-piperidin-3-yl]-methanone as a white foam, MS: 575.3 ([M+H, 1Cl])⁺; [α]_D=−5.09 (c=0.746 g/100 mL, CHCl₃).

Example 87

[4-(5-Chloro-2-methyl-phenyl)-piperazin-1-yl]-[(3S,4S) or (3R,4R)-4-(2,4-difluoro-phenyl)-1-methanesulfonyl-piperidin-3-yl]-methanone In analogy to example 63, step 4, from 4-(5-chloro-2-methyl-phenyl)-piperazin-1-yl]-[(3S,4S) or (3R,4R)-4-(2,4-difluoro-phenyl)-piperidin-3-yl]-methanone hydrochloride and methanesulfonyl chloride was prepared [4-(5-chloro-2-methyl-phenyl)-piperazin-1-yl]-[(3S,4S) or (3R,4R)-4-(2,4-difluoro-phenyl)-1-methanesulfonyl-piperidin-3-yl]-methanone as a white foam, MS: 512.1 ([M+H, 1Cl])⁺; [α]_D=−44.38 (c=0.388 g/100 mL, CHCl₃).

Example 88

[4-(5-Chloro-2-methyl-phenyl)-piperazin-1-yl]-[(3S,4S) or (3R,4R)-4-(2,4-difluoro-phenyl)-1-(propane-2-sulfonyl)-piperidin-3-yl]-methanone In analogy to example 63, step 4, 4-(5-chloro-2-methyl-phenyl)-piperazin-1-yl]-[(3S,4S) or (3R,4R)-4-(2,4-difluoro-phenyl)-piperidin-3-yl]-methanone hydrochloride and 2-propane sulfonyl chloride was prepared [4-(5-chloro-2-methyl-phenyl)-piperazin-1-yl]-[(3S,4S) or (3R,4R)-4-(2,4-difluoro-phenyl)-1-(propane-2-sulfonyl)-piperidin-3-yl]-methanone as a white foam, MS: 540.3 ([M+H, 1Cl])$^+$; $[\alpha]_D=-36.27$ (c=0.623 g/100 mL, CHCl$_3$).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:
1. A compound of formula (I)

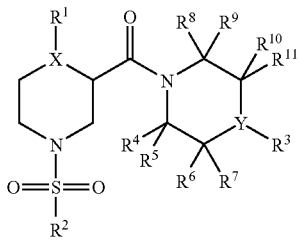

wherein
X is N or CH;
Y is N or CH;
R$^1$ is lower-alkyl of three to seven carbon atoms, aryl, or aryl-lower-alkyl;
R$^2$ is lower-alkyl, fluoro-lower-alkyl, lower-alkoxy-lower-alkyl, cycloalkyl, cycloalkyl-lower-alkyl, aryl, aryl-lower-alkyl, heterocyclyl, heterocyclyl-lower-alkyl, heteroaryl or heteroaryl-lower-alkyl, wherein a cycloalkyl, aryl, heterocyclyl or heteroaryl can optionally be substituted with 1 to 5 substituents independently selected from the group consisting of halogen, lower-alkyl, lower-alkoxy, fluoro-lower-alkyl, fluoro-lower-alkoxy, lower-alkoxy-carbonyl and phenyl;
R$^3$ is aryl or heteroaryl, which is substituted with 1 to 5 substituents independently selected from the group consisting of halogen, CN, lower-alkyl, fluoro-lower-alkyl, lower-alkoxy and fluoro-lower-alkoxy;
R$^4$, R$^5$, R$^6$, R$^7$, R$^8$, R$^9$, R$^{10}$ and R$^{11}$ independently from each other are hydrogen or lower-alkyl, or
R$^4$ and R$^5$ are bound together, or R$^6$ and R$^7$ are bound together, or R$^8$ and R$^9$ are bound together, or R$^{10}$ an R$^{11}$ are bound together, to form a ring together with the carbon atom to which they are attached, and —R$^4$-R$^5$—, —R$^6$-R$^7$—, —R$^8$-R$^9$— and/or —R$^{10}$-R$^{11}$— is —(CH$_2$)$_{2-6}$—,
or a pharmaceutically acceptable salts thereof.
2. A compound of claim 1, wherein X is N.
3. A compound of claim 1, wherein X is CH.
4. A compound of claim 1, wherein Y is N.
5. A compound of claim 1, wherein R$^1$ is aryl or aryl-lower-alkyl, wherein said aryl is optionally substituted with 1 to 3 substituents independently selected from the group consisting of halogen and lower-alkyl.
6. A compound of claim 1, wherein R$^1$ is phenyl optionally substituted with 1 to 2 substituents independently selected from the group consisting of halogen and lower-alkyl.
7. A compound of claim 1, wherein R$^1$ is n-butyl, phenyl, 4-fluoro-2-methyl-phenyl, 2-methyl-phenyl, 4-fluoro-phenyl, 2-fluoro-4-methyl-phenyl or 2,4-difluoro-phenyl.
8. A compound of claim 1, wherein R$^2$ is lower-alkyl, aryl or heteroaryl selected from the group consisting of isoxazolyl, quinolinyl, thiophenyl and pyridinyl, which aryl or heteroaryl is optionally substituted with 1 to 3 substituents independently selected from the group consisting of halogen, lower-alkyl, lower-alkoxy, fluoro-lower-alkyl, lower-alkoxy-carbonyl and phenyl.
9. A compound of claim 1, wherein R$^2$ is lower-alkyl, phenyl or heteroaryl selected from the group consisting of quinolinyl and pyridinyl, which phenyl or heteroaryl is optionally substituted with 1 to 2 substituents independently selected from the group consisting of halogen, lower-alkoxy and fluoro-lower-alkyl.
10. A compound of claim 1, wherein R$^2$ is methyl, isopropyl, 3-methoxy-phenyl, 3-chloro-phenyl, 2-trifluoromethyl-phenyl, quinoline-8-yl or pyridin-3-yl.
11. A compound of claim 1, wherein R$^3$ is pyridinyl or pyrazinyl which is substituted with 1 to 3 substituents independently selected from the group consisting of halogen, lower-alkyl and fluoro-lower-alkyl.
12. A compound of claim 1, wherein R$^3$ is phenyl or pyrazinyl which is substituted with 1 to 2 substituents independently selected from the group consisting of halogen and lower-alkyl.
13. A compound of claim 1, wherein R$^3$ is 2,5-dimethyl-phenyl, 2-methyl-5-chloro-phenyl, 2,5-dichloro-phenyl or 3,6-dimethyl-pyrazin-2-yl.
14. A compound of claim 1, wherein R$^4$, R$^5$, R$^6$, R$^7$, R$^8$, R$^9$, R$^{10}$ and R$^{11}$ are hydrogen.
15. A compound of claim 1, selected from the group consisting of
[4-(2,5-Dimethyl-phenyl)-piperazin-1-yl]-[1-(4-fluoro-2-methyl-phenyl)-4-(3-methoxy-benzenesulfonyl)-piperazin-2-yl]-methanone,
[4-(3-Chloro-benzenesulfonyl)-1-(4-fluoro-2-methyl-phenyl)-piperazin-2-yl]-[4-(2,5-dimethyl-phenyl)-piperazin-1-yl]-methanone,
[4-(3-Chloro-benzenesulfonyl)-1-(4-fluoro-2-methyl-phenyl)-piperazin-2-yl]-[4-(5-chloro-2-methyl-phenyl)-piperazin-1-yl]-methanone,
[4-(3-Chloro-benzenesulfonyl)-1-(4-fluoro-2-methyl-phenyl)-piperazin-2-yl]-[4-(2,5-dichloro-phenyl)-piperazin-1-yl]-methanone,
(−)-[4-(3-Chloro-benzenesulfonyl)-1-(4-fluoro-2-methyl-phenyl)-piperazin-2-yl]-[4-(2,5dichloro-phenyl)piperazin-1-yl]-methanone,
[4-(3-Chloro-benzenesulfonyl)-1-(4-fluoro-2-methyl-phenyl)-piperazin-2-yl]-(4-o-tolyl-piperazin-1-yl)-methanone,
[4-(2,5-Dichloro-phenyl)-piperazin-1-yl]-[4-(3-methoxy-benzenesulfonyl)-1-phenyl-piperazin-2-yl]-methanone,
[4-(2,5-Dimethyl-phenyl)-piperazin-1-yl]-[4-(3-methoxy-benzenesulfonyl)-1-phenyl-piperazin-2-yl]-methanone,
[4-(5-Chloro-2-methyl-phenyl)-piperazin-1-yl]-[4-(3-methoxy-benzenesulfonyl)-1-phenyl-piperazin-2-yl]-methanone,
[4-(3-Chloro-benzenesulfonyl)-1-o-tolyl-piperazin-2-yl]-[4-(2,5-dichloro-phenyl)-piperazin-1-yl]-methanone,
[4-(3-Chloro-benzenesulfonyl)-1-o-tolyl-piperazin-2-yl]-[4-(5-chloro-2-methyl-phenyl)-piperazin-1-yl]-methanone,
[4-(3-Chloro-benzenesulfonyl)-1-o-tolyl-piperazin-2-yl]-[4-(2,5-dimethyl-phenyl)-piperazin-1-yl]-methanone,
[1-Benzyl-4-(3-methoxy-benzenesulfonyl)-piperazin-2-yl]-[4-(2,5-dimethyl-phenyl)-piperazin-1-yl]-methanone,
(−)-[1-Benzyl-4-(3-methoxy-benzenesulfonyl)-piperazin-2-yl]-[4-(2,5-dimethyl-phenyl)-piperazin-1-yl]-methanone,
[1-Benzyl-4-(3-chloro-benzenesulfonyl)-piperazin-2-yl]-[4-(2,5-dimethyl-phenyl)-piperazin-1-yl]-methanone, and
[1-Benzyl-4-(3,5-dimethyl-isoxazole-4-sulfonyl)-piperazin-2-yl]-[4-(2,5-dimethyl-phenyl)-piperazin-1-yl]-methanone,
or a pharmaceutically acceptable salt thereof.

16. A compound of claim 1, selected from the group consisting of

[4-(3-Chloro-benzenesulfonyl)-1-propyl-piperazin-2-yl]-[4-(2,5-dimethyl-phenyl)-piperazin-1-yl]-methanone,
[1-Butyl-4-(3-chloro-benzenesulfonyl)-piperazin-2-yl]-[4-(2,5-dimethyl-phenyl)-piperazin-1-yl]-methanone,
[4-(3-Chloro-benzenesulfonyl)-1-pentyl-piperazin-2-yl]-[4-(2,5-dimethyl-phenyl)-piperazin-1-yl]-methanone,
[4-(3-Chloro-benzenesulfonyl)-1-isobutyl-piperazin-2-yl]-[4-(2,5-dimethyl-phenyl)-piperazin-1-yl]-methanone,
[4-(3-Chloro-benzenesulfonyl)-1-phenethyl-piperazin-2-yl]-[4-(2,5-dimethyl-phenyl)-piperazin-1-yl]-methanone,
[4-(4-Chloro-benzenesulfonyl)-1-pentyl-piperazin-2-yl]-[4-(2,5-dimethyl-phenyl)-piperazin-1-yl]-methanone,
[1-Butyl-4-(4-chloro-benzenesulfonyl)-piperazin-2-yl]-[4-(2,5-dimethyl-phenyl)-piperazin-1-yl]-methanone,
[4-(4-Chloro-benzenesulfonyl)-1-phenyl-piperazin-2-yl]-[4-(2,5-dimethyl-phenyl)-piperazin-1-yl]-methanone,
[4-(2-Chloro-benzenesulfonyl)-1-(4-fluoro-2-methyl-phenyl)-piperazin-2-yl]-[4-(2,5-dichloro-phenyl)-piperazin-1-yl]-methanone,
[4-(2-Chloro-benzenesulfonyl)-1-(4-fluoro-2-methyl-phenyl)-piperazin-2-yl]-[4-(5-chloro-2-methyl-phenyl)-piperazin-1-yl]-methanone,
[4-(2-Chloro-benzenesulfonyl)-1-(4-fluoro-2-methyl-phenyl)-piperazin-2-yl]-[4-(2,5-dimethyl-phenyl)-piperazin-1-yl]-methanone,
[4-(2,5-Dichloro-phenyl)-piperazin-1-yl]-[1-(4-fluoro-2-methyl-phenyl)-4-(naphthalene-1-sulfonyl)-piperazin-2-yl]-methanone,
[4-(5-Chloro-2-methyl-phenyl)-piperazin-1-yl]-[1-(4-fluoro-2-methyl-phenyl)-4-(naphthalene-1-sulfonyl)-piperazin-2-yl]-methanone,
[4-(2,5-Dimethyl-phenyl)-piperazin-1-yl]-[1-(4-fluoro-2-methyl-phenyl)-4-(naphthalene-1-sulfonyl)-piperazin-2-yl]-methanone, and
[1-(4-Fluoro-2-methyl-phenyl)-4-(naphthalene-1-sulfonyl)-piperazin-2-yl]-[4-(3-trifluoromethyl-pyridin-2-yl)-piperazin-1-yl]-methanone,
or a pharmaceutically acceptable salt thereof.

17. A compound of claim 1, selected from the group consisting of [4-(2,5-Dichloro-phenyl)-piperazin-1-yl]-[1-(4-fluoro-2-methyl-phenyl)-4-(quinoline-8-sulfonyl)-piperazin-2-yl]-methanone,

[4-(5-Chloro-2-methyl-phenyl)-piperazin-1-yl]-[1-(4-fluoro-2-methyl-phenyl)-4-(quinoline-8-sulfonyl)-piperazin-2-yl]-methanone,
[4-(2,5-Dimethyl-phenyl)-piperazin-1-yl]-[1-(4-fluoro-2-methyl-phenyl)-4-(quinoline-8-sulfonyl)-piperazin-2-yl]-methanone,
[4-(2,5-Dichloro-phenyl)-piperazin-1-yl]-[4-(propane-2-sulfonyl)-1-o-tolyl-piperazin-2-yl]-methanone,
[4-(Biphenyl-4-sulfonyl)-1-o-tolyl-piperazin-2-yl]-[4-(2,5-dichloro-phenyl)-piperazin-1-yl]-methanone,
3-{3-[4-(2,5-Dichloro-phenyl)-piperazine-1-carbonyl]-4-o-tolyl-piperazine-1-sulfonyl}-thiophene-2-carboxylic acid methyl ester,
[4-(3-Chloro-benzenesulfonyl)-1-(4-fluoro-2-methyl-phenyl)-piperazin-2-yl]-(3',6'-dimethyl-2,3,5,6-tetrahydro-[1,2']bipyrazinyl-4-yl)-methanone,
[1-Benzyl-4-(3-chloro-benzenesulfonyl)-piperazin-2-yl]-(3',6'-dimethyl-2,3,5,6-tetrahydro-[1,2']bipyrazinyl-4-yl)-methanone,
[4-(3-Chloro-phenyl)-piperidin-1-yl]-[1-(4-fluoro-2-methyl-phenyl)-4-(propane-2-sulfonyl)-piperazin-2-yl]-methanone,
[4-(3-Chloro-benzenesulfonyl)-1-o-tolyl-piperazin-2-yl]-(3',6'-dimethyl-2,3,5,6-tetrahydro-[1,2']bipyrazinyl-4-yl)-methanone,
Cis-[4-(2,5-Dimethyl-phenyl)-piperazin-1-yl]-[-1-(3-methoxy-benzenesulfonyl)-4-phenyl-piperidin-3-yl]-methanone,
[4-(2,5-Dimethyl-phenyl)-piperazin-1-yl]-[(3S,4S)-1-(3-methoxy-benzenesulfonyl)-4-phenyl-piperidin-3-yl]-methanone,
[Trans-1-(3-Chloro-benzenesulfonyl)-4-phenyl-piperidin-3-yl]-[4-(2,5-dimethyl-phenyl)-piperazin-1-yl]-methanone,
[Trans-1-(3,5-Dimethyl-isoxazole-4-sulfonyl)-4-phenyl-piperidin-3-yl]-[4-(2,5-dimethyl-phenyl)-piperazin-1-yl]-methanone, and
[4-(2,5-Dimethyl-phenyl)-piperazin-1-yl]-[(3S,4S)-1-(3-methoxy-benzenesulfonyl)-4-o-tolyl-piperidin-3-yl]-methanone,
or a pharmaceutically acceptable salt thereof.

18. A compound of claim 1, selected from the group consisting of

[(3S,4S)-1-(3-Chloro-benzenesulfonyl)-4-o-tolyl-piperidin-3-yl]-[4-(2,5-dimethyl-phenyl)-piperazin-1-yl]-methanone,
[4-(2,5-Dimethyl-phenyl)-piperazin-1-yl]-((3S,4S)-1-methanesulfonyl-4-o-tolyl-piperidin-3-yl)-methanone,
[(3S,4S)-1-(3-Chloro-benzenesulfonyl)-4-phenyl-piperidin-3-yl]-[4-(2,5-dimethyl-phenyl)-piperazin-1-yl]-methanone,
[4-(2,5-Dimethyl-phenyl)-piperazin-1-yl]-((3S,4S)-1-methanesulfonyl-4-phenyl-piperidin-3-yl)-methanone,
[(3R,4R)-1-(3-Chloro-benzenesulfonyl)-4-phenyl-piperidin-3-yl]-[4-(2,5-dimethyl-phenyl)-piperazin-1-yl]-methanone,
[4-(2,5-Dimethyl-phenyl)-piperazin-1-yl]-[(3S,4R)-1-(3-methoxy-benzenesulfonyl)-4-o-tolyl-piperidin-3-yl]-methanone,
[(3S,4S)-1-(3-Chloro-benzenesulfonyl)-4-(4-fluoro-phenyl)-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4S)-4-(4-fluoro-phenyl)-1-(2-trifluoromethyl-benzenesulfonyl)-piperidin-3-yl]-methanone,
[(3S,4R)-1-(3-Chloro-benzenesulfonyl)-4-(4-fluoro-phenyl)-piperidin-3-yl]-[4-(5-chloro-2-methyl-phenyl)-piperazin-1-yl]-methanone,
[(3S,4R)-1-(2-Chloro-benzenesulfonyl)-4-(4-fluoro-phenyl)-piperidin-3-yl]-[4-(5-chloro-2-methyl-phenyl)-piperazin-1-yl]-methanone,
[4-(5-Chloro-2-methyl-phenyl)-piperazin-1-yl]-[(3S,4R)-4-(4-fluoro-phenyl)-1-(pyridine-3-sulfonyl)-piperidin-3-yl]-methanone,
[(3S,4S) or (3R,4R)-1-(3-Chloro-benzenesulfonyl)-4-(2-fluoro-4-methyl-phenyl)-piperidin-3-yl]-[4-(5-chloro-2-methyl-phenyl)-piperazin-1-yl]-methanone,
[(3S,4S) or (3R,4R)-1-(2-Chloro-benzenesulfonyl)-4-(2-fluoro-4-methyl-phenyl)-piperidin-3-yl]-[4-(5-chloro-2-methyl-phenyl)-piperazin-1-yl]-methanone,
(3S,4S) or (3R,4R)-[4-(5-Chloro-2-methyl-phenyl)-piperazin-1-yl]-[4-(2-fluoro-4-methyl-phenyl)-1-(2-trifluoromethyl-benzenesulfonyl)-piperidin-3-yl]-methanone, and
(3S,4S) or (3R,4R)-[4-(5-Chloro-2-methyl-phenyl)-piperazin-1-yl]-[4-(2-fluoro-4-methyl-phenyl)-1-(pyridine-3-sulfonyl)-piperidin-3-yl]-methanone,
or a pharmaceutically acceptable salt thereof.

19. A compound of claim 1, selected from the group consisting of
- (3S,4S) or (3R,4R)-[4-(5-Chloro-2-methyl-phenyl)-piperazin-1-yl]-[4-(2-fluoro-4-methyl-phenyl)-1-(propane-2-sulfonyl)-piperidin-3-yl]-methanone,
- [(3S,4R)-1-(3-Chloro-benzenesulfonyl)-4-phenyl-piperidin-3-yl]-[4-(5-chloro-2-methyl-phenyl)-piperazin-1-yl]-methanone,
- [4-(5-Chloro-2-methyl-phenyl)-piperazin-1-yl]-[(3S,4R)-4-phenyl-1-(2-trifluoromethyl-benzenesulfonyl)-piperidin-3-yl]-methanone,
- [4-(5-Chloro-2-methyl-phenyl)-piperazin-1-yl]-[(3S,4R)-4-phenyl-1-(pyridine-3-sulfonyl)-piperidin-3-yl]-methanone,
- [(3S,4R)-1-(3-Chloro-benzenesulfonyl)-4-o-tolyl-piperidin-3-yl]-[4-(5-chloro-2-methyl-phenyl)-piperazin-1-yl]-methanone,
- [4-(5-Chloro-2-methyl-phenyl)-piperazin-1-yl]-[(3S,4R)-4-o-tolyl-1-(2-trifluoromethyl-benzenesulfonyl)-piperidin-3-yl]-methanone,
- [4-(5-Chloro-2-methyl-phenyl)-piperazin-1-yl]-[(3S,4R)-1-(pyridine-3-sulfonyl)-4-o-tolyl-piperidin-3-yl]-methanone,
- [(3S,4R) or (3R,4S)-1-(3-Chloro-benzenesulfonyl)-4-(2,4-difluoro-phenyl)-piperidin-3-yl]-[4-(5-chloro-2-methyl-phenyl)-piperazin-1-yl]-methanone,
- (3S,4R) or (3R,4S)-[4-(5-Chloro-2-methyl-phenyl)-piperazin-1-yl]-[4-(2,4-difluoro-phenyl)-1-(pyridine-3-sulfonyl)-piperidin-3-yl]-methanone,
- [(3S,4S)-1-(3-Chloro-benzenesulfonyl)-4-phenyl-piperidin-3-yl]-[4-(5-chloro-2-methyl-phenyl)-piperazin-1-yl]-methanone,
- [4-(5-Chloro-2-methyl-phenyl)-piperazin-1-yl]-[(3S,4S)-4-phenyl-1-(2-trifluoromethyl-benzenesulfonyl)-piperidin-3-yl]-methanone,
- [4-(5-Chloro-2-methyl-phenyl)-piperazin-1-yl]-[(3S,4S)-4-phenyl-1-(pyridine-3-sulfonyl)-piperidin-3-yl]-methanone,
- [4-(5-Chloro-2-methyl-phenyl)-piperazin-1-yl]-[(3S,4S)-4-phenyl-1-(propane-2-sulfonyl)-piperidin-3-yl]-methanone,
- [4-(5-Chloro-2-methyl-phenyl)-piperazin-1-yl]-((3S,4S)-1-methanesulfonyl-4-phenyl-piperidin-3-yl)-methanone, and
- [(3S,4S)-1-(3-Chloro-benzenesulfonyl)-4-o-tolyl-piperidin-3-yl]-[4-(5-chloro-2-methyl-phenyl)-piperazin-1-yl]-methanone, or a pharmaceutically acceptable salt thereof.

20. A compound of claim 1, selected from the group consisting of
- [4-(5-Chloro-2-methyl-phenyl)-piperazin-1-yl]-[(3S,4S)-4-o-tolyl-1-(2-trifluoromethyl-benzenesulfonyl)-piperidin-3-yl]-methanone,
- [4-(5-Chloro-2-methyl-phenyl)-piperazin-1-yl]-[(3S,4S)-1-(pyridine-3-sulfonyl)-4-o-tolyl-piperidin-3-yl]-methanone,
- [4-(5-Chloro-2-methyl-phenyl)-piperazin-1-yl]-((3S,4S)-1-methanesulfonyl-4-o-tolyl-piperidin-3-yl)-methanone,
- [(3S,4S) or (3R,4R)-1-(3-Chloro-benzenesulfonyl)-4-(4-fluoro-2-methyl-phenyl)-piperidin-3-yl]-[4-(5-chloro-2-methyl-phenyl)-piperazin-1-yl]-methanone,
- [4-(5-Chloro-2-methyl-phenyl)piperazin-1-yl]-[(3S,4S) or (3R,4R)-4-(4-fluoro-2-methyl-phenyl)-1-(2-trifluoromethyl-benzenesulfonyl)-piperidin-3-yl]-methanone,
- [4-(5-Chloro-2-methyl-phenyl)piperazin-1-yl]-[(3S,4S) or (3R,4R)-4-(4-fluoro-2-methyl-phenyl)-1-(pyridine-3-sulfonyl)-piperidin-3-yl]-methanone,
- [4-(5-Chloro-2-methyl-phenyl)piperazin-1-yl]-[(3S,4S) or (3R,4R)-4-(4-fluoro-2-methyl-phenyl)-1-methanesulfonyl-piperidin-3-yl]-methanone,
- [(3S,4S) or (3R,4R)-1-(3-Chloro-benzenesulfonyl)-4-(2,4-difluoro-phenyl)-piperidin-3-yl]-[4-(5-chloro-2-methyl-phenyl)-piperazin-1-yl]-methanone,
- [4-(5-Chloro-2-methyl-phenyl)piperazin-1-yl]-[(3S,4S) or (3R,4R)-4-(2,4-difluoro-phenyl)-1-(2-trifluoromethyl-benzenesulfonyl)-piperidin-3-yl]-methanone,
- [4-(5-Chloro-2-methyl-phenyl)piperazin-1-yl]-[(3S,4S) or (3R,4R)-4-(2,4-difluoro-phenyl)-1-(pyridine-3-sulfonyl)-piperidin-3-yl]-methanone,
- [4-(5-Chloro-2-methyl-phenyl)piperazin-1-yl]-[(3S,4S) or (3R,4R)-4-(2,4-difluoro-phenyl)-1-methanesulfonyl-piperidin-3-yl]-methanone, and
- [4-(5-Chloro-2-methyl-phenyl)piperazin-1-yl]-[(3S,4S) or (3R,4R)-4-(2,4-difluoro-phenyl)-1-(propane-2-sulfonyl)-piperidin-3-yl]-methanone, or a pharmaceutically acceptable salt thereof.

21. A compound of claim 1, selected from the group consisting of
- [4-(2,5-Dimethyl-phenyl)-piperazin-1-yl]-[1-(4-fluoro-2-methyl-phenyl)-4-(3-methoxy-benzenesulfonyl)-piperazin-2-yl]-methanone,
- [4-(3-Chloro-benzenesulfonyl)-1-(4-fluoro-2-methyl-phenyl)-piperazin-2-yl]-[4-(2,5-dichloro-phenyl)-piperazin-1-yl]-methanone,
- [4-(2,5-Dimethyl-phenyl)-piperazin-1-yl]-[4-(3-methoxy-benzenesulfonyl)-1-phenyl-piperazin-2-yl]-methanone,
- [4-(3-Chloro-benzenesulfonyl)-1-o-tolyl-piperazin-2-yl]-[4-(2,5-dimethyl-phenyl)-piperazin-1-yl]-methanone,
- [1-Butyl-4-(3-chloro-benzenesulfonyl)-piperazin-2-yl]-[4-(2,5-dimethyl-phenyl)-piperazin-1-yl]-methanone,
- [4-(2,5-Dimethyl-phenyl)-piperazin-1-yl]-[1-(4-fluoro-2-methyl-phenyl)-4-(quinoline-8-sulfonyl)-piperazin-2-yl]-methanone,
- [4-(2,5-Dichloro-phenyl)-piperazin-1-yl]-[4-(propane-2-sulfonyl)-1-o-tolyl-piperazin-2-yl]-methanone,
- [4-(3-Chloro-benzenesulfonyl)-1-(4-fluoro-2-methyl-phenyl)-piperazin-2-yl]-(3',6'-dimethyl-2,3,5,6-tetrahydro-[1,2']bipyrazinyl-4-yl)-methanone,
- [4-(3-Chloro-benzenesulfonyl)-1-o-tolyl-piperazin-2-yl]-(3',6'-dimethyl-2,3,5,6-tetrahydro-[1,2']bipyrazinyl-4-yl)-methanone,
- [4-(2,5-Dimethyl-phenyl)-piperazin-1-yl]-[(3S,4R)-1-(3-methoxy-benzenesulfonyl)-4-o-tolyl-piperidin-3-yl]-methanone,
- [4-(5-Chloro-2-methyl-phenyl)-piperazin-1-yl]-[(3S,4R)-4-(4-fluoro-phenyl)-1-(pyridine-3-sulfonyl)-piperidin-3-yl]-methanone,
- (3S,4S) or (3R,4R)-[4-(5-Chloro-2-methyl-phenyl)-piperazin-1-yl]-[4-(2-fluoro-4-methyl-phenyl)-1-(2-trifluoromethyl-benzenesulfonyl)-piperidin-3-yl]-methanone,
- [(3S,4R)-1-(3-Chloro-benzenesulfonyl)-4-o-tolyl-piperidin-3-yl]-[4-(5-chloro-2-methyl-phenyl)-piperazin-1-yl]-methanone,
- (3S,4R) or (3R,4S)-[4-(5-Chloro-2-methyl-phenyl)-piperazin-1-yl]-[4-(2,4-difluoro-phenyl)-1-(pyridine-3-sulfonyl)-piperidin-3-yl]-methanone, and
- [4-(5-Chloro-2-methyl-phenyl)piperazin-1-yl]-[(3S,4S) or (3R,4R)-4-(2,4-difluoro-phenyl)-1-methanesulfonyl-piperidin-3-yl]-methanone, or a pharmaceutically acceptable salt thereof.

22. A pharmaceutical composition comprising a compound of claim 1 and a pharmaceutically acceptable carrier and/or adjuvant.

* * * * *